(12) United States Patent
Xu et al.

(10) Patent No.: US 9,056,141 B2
(45) Date of Patent: Jun. 16, 2015

(54) THIOL-ENE CLICK CHEMISTRY FOR DRUG CONJUGATES

(71) Applicant: SYNCHEM, INC., Elk Grove Village, IL (US)

(72) Inventors: Ze-Qi Xu, Woodridge, IL (US); Qianli Wang, Chicago, IL (US); Augustine Rudolph Joseph, Des Plaines, IL (US); Zhiqiang Fang, Hawthorn Woods, IL (US)

(73) Assignee: SynChem, Inc., Elk Grove Village, IL (US)

( * ) Notice: Subject to any disclaimer, the term of this patent is extended or adjusted under 35 U.S.C. 154(b) by 0 days.

(21) Appl. No.: 13/907,427

(22) Filed: May 31, 2013

(65) Prior Publication Data

US 2013/0323169 A1   Dec. 5, 2013

Related U.S. Application Data

(60) Provisional application No. 61/653,823, filed on May 31, 2012.

(51) Int. Cl.
  *A61K 47/48* (2006.01)
  *A61K 51/10* (2006.01)
(52) U.S. Cl.
  CPC ....... *A61K 47/48715* (2013.01); *A61K 51/1096* (2013.01); *A61K 47/48384* (2013.01); *A61K 47/48569* (2013.01); *A61K 51/1045* (2013.01)
(58) Field of Classification Search
  USPC ............ 424/1.53, 178.1, 179.1, 181.1, 184.1; 530/322, 323, 391.7, 391.9, 395, 351
  See application file for complete search history.

(56) References Cited

U.S. PATENT DOCUMENTS

2003/0130189 A1 * 7/2003 Senter et al. ................ 514/12

FOREIGN PATENT DOCUMENTS

WO      2011/090428 A1     7/2011

OTHER PUBLICATIONS

Berge, S.M., et al., "Pharmaceutical Salts," J. Pharm. Sci., Jan. 1977, vol. 66(1), pp. 1-19.
Dubowchik, G.M., et al., "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity," Bioconjugate Chem., Jun. 18, 2002, vol. 13(4), pp. 855-869.
Glaser, M., et al., "Radiosynthesis and Biodistribution of Cyclic RGD Peptides Conjugated with Novel [18F] Fluorinated Aldehyde-Containing Prosthetic Groups," Bioconjugate Chem., Mar. 15, 2008, vol. 19(4), pp. 951-957.
Hoyle, et al., "Thiol-Ene Click Chemistry," Angew. Chem. Int. Ed., Feb. 22, 2010, vol. 49(9), pp. 1540-1573.
Katz, et al., "Brentuximab Vedotin (SGN-35)," Clin. Cancer Res., Oct. 15, 2011, vol. 17, pp. 6428-6436.

(Continued)

*Primary Examiner* — Michael G Hartley
*Assistant Examiner* — Jagadishwar Samala
(74) *Attorney, Agent, or Firm* — McDonnell Boehnen Hulbert & Berghoff LLP

(57) ABSTRACT

The present invention relates to linker molecules that readily conjugate cellular recognition ligand at one end and drug payload at the other, and are useful in treating or preventing cancer, an autoimmune disease, an inflammatory condition, a central nervous system disorder or an infection. The linker inker molecules of the invention are represented by Formula I, II and III; Linker-Drug compounds represented by Formula IV, V and VI; and Ligand-Linker-Drug conjugates represented by Formula VII, VIII and IX:

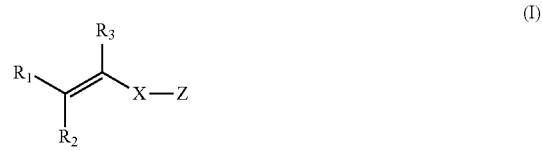

(I)

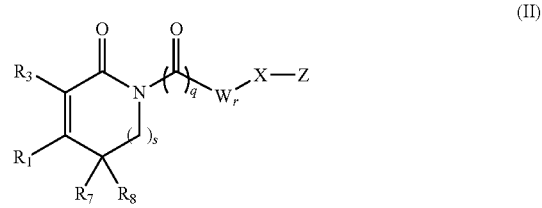

(II)

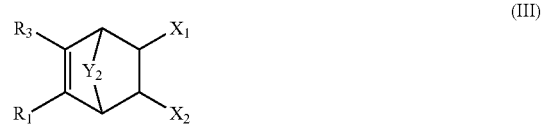

(III)

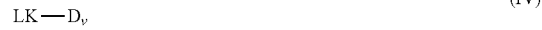

(IV)

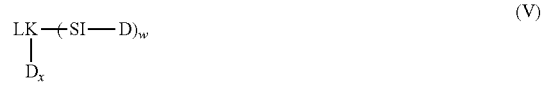

(V)

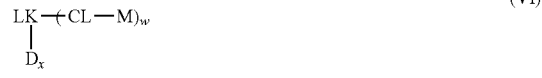

(VI)

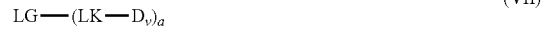

(VII)

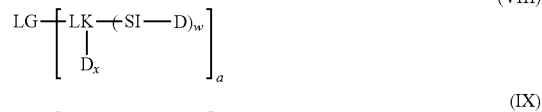

(VIII)

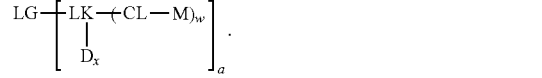

(IX)

5 Claims, No Drawings

(56) References Cited

OTHER PUBLICATIONS

Northrop, B.H., Coffey, R.N., "Thiol-Ene Click Chemistry: Computational and Kinetic Analysis of the Influence of Alkene Functionality," J. Am. Chem. Soc., Aug. 1, 2012, vol. 134(33), pp. 13804-13817.

Palmer, B.D., et al., "DNA-Directed Alkylating Agents. 2. Synthesis and Biological Activity of Platinum Complexes Linked to 9-Anilinoacridine," J. Med. Chem., 1990, vol. 33, pp. 3008-3014.

Petit, G.R., et al., "Antineoplastic agents 365. Dolastatin 10 SAR probes," Anti-Cancer Drug Design, Jun. 1, 1998, vol. 13(4), pp. 243-277.

Ricart, A.D., "Antibody-Drug Conjugates of Calicheamicin Derivative: Gemtuzumab Ozogamicin and Inotuzumab Ozogamicin," Clin. Cancer Res., Oct. 15, 2011, vol. 17, pp. 6417-6427.

Rosillo, M., et al., "Combination of RCM and the Pauson-Khand Reaction: One-Step Synthesis of Tricyclic Structures," Eur. J. Org. Chem., Aug. 2008, vol. 2008(23), pp. 3917-3927.

Seitz, O., et al., "A Novel Allylic Anchor for Solid-Phase Synthesis-Synthesis of Protected and Unprotected O-Glycosylated Mucin-Type Glycopeptides," Angew. Chem. Int. Ed. Engl., 1995, vol. 34(7), pp. 803-805.

Shen, B-Q., et al., "Conjugation site modulates the in vivo stability and therapeutic activity of antibody-drug conjugates," Nat. Biotechnol., Jan. 22, 2012, vol. 30, doi:10.1038/nbt.2108.

Teicher, B.A., "Antibody-Drug Conjugate Targets," Current Cancer Drug Targets, Dec. 2009, vol. 9(8), pp. 982-1004.

Ting, C.M., et al., "Distinct Chemoselectivities in the Platinum-Catalyzed 1,2-Carboalkoxylations of 5-Alkoxypent-1-yn-3-ol Derivatives," Org. Lett., Mar. 4, 2011, vol. 13(7), pp. 1702-1705.

\* cited by examiner

THIOL-ENE CLICK CHEMISTRY FOR DRUG CONJUGATES

CROSS-REFERENCE TO OTHER APPLICATIONS

This application claims the benefit of U.S. Provisional Application No. 61/653,823 filed May 31, 2012, which is incorporated by reference in its entirety.

FIELD OF THE INVENTION

The present invention relates to linker molecules that readily conjugate cellular recognition ligand at one end and drug payload at the other. In particular, the present invention is directed to Linker molecules, Linker-Drug compounds, Ligand-Linker-Drug conjugates, to compositions including the same, and to methods for using the same to treat, prevent or diagnose cancer, an autoimmune disease, an inflammatory condition, a central nervous system disorder or an infection. The present invention is also directed to Antibody-Drug Conjugates, to compositions including the same, and to methods for using the same to treat, prevent or diagnose cancer, an autoimmune disease, an inflammatory condition, a central nervous system disorder or an infection.

BACKGROUND OF INVENTION

Monoclonal antibodies (mAbs) play an important role in cancer chemotherapy. However, their activity is often not sufficient to produce a lasting benefit. Recent advances in antibody-drug conjugates (ADCs) allow to harness mAb specificity and target the delivery of a cytotoxic agent to the tumor with specific antigen expressed on the surface of a malignant cell, resulting in significant enhancement of both mAb and drug efficacies (Teicher B A. *Current Cancer Drug Targets,* 2009, 9, 982-1004). In an ADC, the highly potent cytotoxic agent is covalently linked to an antibody or antibody fragment. To achieve the effective therapeutic effects, all three components—antibody, linker and payload—play critical roles in defining target specificity, the degree of stability and mechanism of action and demanding criteria must be satisfied. Indeed, the in vivo stability and efficacy of ADCs can be improved by optimizing the linker and by selecting the appropriate antibody and payload.

Gemtuzumab ozogamicin (Mylotarg) was the first ADC approved in 2000 for the treatment of acute myelogenous leukemia (AML) but was then withdrawn from the market in 2010 because the post-marketing clinical trials failed to meet the prospective efficacy endpoint (Ricart A D. *Clin Cancer Res.* 2011, 17, 6417-6427). The second ADC, brentuximab vedotin (SGN-35, Adcetris), was approved on Aug. 19, 2011 under the accelerated conditions for the treatment of Hodgkin lymphoma and systemic anaplastic large cell lymphoma (ALCL) (Katz et al. *Clin Cancer Res.* 2011, 17, 6428-6436). However, significant side effects have been reported in patients receiving Adcetris treatment, with 31% of patients in clinical trials experiencing serious adverse events and 21% discontinuing the treatment due to adverse events. FDA added a black-boxed warning to Adcetris drug label that progressive multifocal leukoencephalopathy (PML) has been reported in Adcetris-treated patients. Other important warnings and precautions associated with Adcetris treatment include peripheral neuropathy, neutropenia, Stevens-Johnson syndrome and tumor lysis syndrome.

Thiol-maleimide chemistry is a commonly used method, whereby a cysteine residue, either native or engineered, for conjugation of mAb with cytotoxic agent. However, the thiol-succinimide adduct is known to undergo alkaline hydrolysis and retro-Michael addition. Particularly, the thiol-succinimide moiety in ADCs, when situated in the highly solvent-accessible sites, is susceptible to the exchange process with albumin, cysteine or glutathione as well as succinimide ring hydrolysis both in vitro and in vivo (Shen et al. *Nat. Biotechonol.* 2012, doi:10.1038/nbt.2108). The rapid dissociation of cytotoxic drug from the mAb, due to the maleimide exchange process, showed reduced target specific activity and increased liver toxicity in animal model. The instability of thiol-succinimide structure may have been the contributing factor in the serious adverse events associated with ADC treatment.

SUMMARY OF INVENTION

In one aspect, the present invention provides linker (LK) compounds that would readily allow conjugation of cellular recognition ligands to target antigens or receptors, such as antibodies, antibody fragments, proteins, peptides, polypeptides, growth factors, lectins, steroidal estrogens, vitamins and nutrient-transport molecules, with drug payload molecules including but not limiting to cytotoxic agents, target chemotherapeutic agents, radionuclides, immunomodulating agents. The linker compound has a double bond as the thiol acceptor and a functional group, and is represented by the general formulae:

(I)

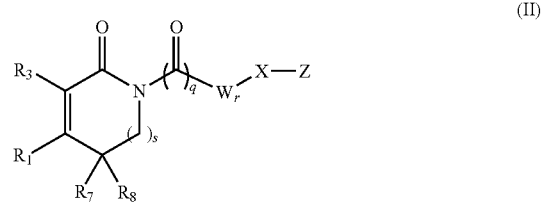

(II)

(III)

In another aspect, the present invention provides Linker-Drug molecules or a pharmaceutically acceptable salt or solvate thereof, represented by the general formulae:

(IV)

(V)

(VI)

wherein
LK is a linker moiety selected from Formula I, II and III;
D is a drug moiety;

SI is a self-immolative moiety;
CL is a metal chelating agent;
M is a radionuclide In still another aspect, the present invention provides Ligand-Linker-Drug conjugates or a pharmaceutically acceptable salt or solvate thereof, represented by the general formulae:

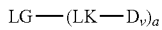  (VII)

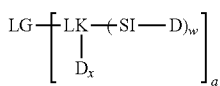  (VIII)

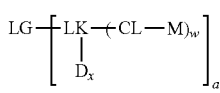  (IX)

wherein
D, SI, CI and M are defined as above;
LG is a ligand moiety;
LK is a linker moiety selected from Formula I, II or III and covalently attached to a ligand (LG) through a thioether bond formed between a sulfhydryl or thiol group (—SH) on the LG with the double bond of the LK.

The disclosure also provides methods of preparing a Ligand-Linker-Drug conjugate compound, the method comprising:
(a) coupling a linker (LK) compound selected from Formula I, II or III

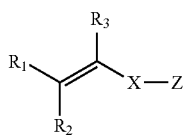  (I)

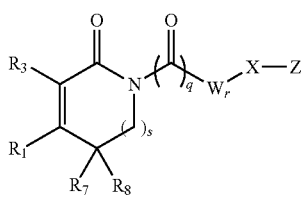  (II)

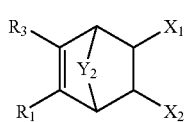  (III)

wherein
$R_1$, $R_2$ and $R_3$ are independently selected from H, deuterium, halogen, CN, $NO_2$, HC(O), $CO_2H$, $C(O)NH_2$, $S(O)_2OH$, $S(O)_2NH_2$, a straight or branched $C_{1-8}$ alkyl, aryl-$C_{1-8}$ alkyl, heterocycle-$C_{1-8}$ alkyl, cyclo($C_{3-9}$)alkyl, aryl, heterocycle, $R_4C(O)$, $R_4O$, $R_4S$, $R_4S(O)$, $R_4S(O)_2$, $R_4NH$, $R_4R_5N$, $C(Y)OR_4$, $C(Y)SR_4$, $C(Y)NHR_4$, $C(Y)NR_4R_5$, $R_4OC(Y)$, $R_4SC(Y)$, $R_4NHC(Y)$, $R_4R_5NC(Y)$, $R_4OS(O)_2$, H—Y—$(CH_2CH_2O)_m$, $R_4$—Y—$(CH_2CH_2O)_m$, $R_4C(Y)$—O—$(CH_2CH_2O)_m$, $R_4C(Y)$—S—$(CH_2CH_2O)_m$, $R_4C(Y)$—NH—$(CH_2CH_2O)_m$, $R_4C(Y)$—N($R_5$)—$(CH_2CH_2O)_m$, or —X—Z, wherein the aryl comprises phenyl or naphthyl;
the heterocycle comprises
a 5 or 6 membered aromatic heterocycle selected from the group consisting of pyridyl, diazinyl, pyrimidinyl, 5-methoxy pyrimidinyl, (1,2,4)triazine-3,5-dione-6-yl, 6-mercaptopyrimidine-4-yl, pyrrolyl, pyrazolyl, imidazolyl, oxazolyl, isoxazolyl, thiazolyl, isothiazolyl, furanyl, and thienyl;
a 3 to 9 membered non-aromatic heterocycle selected from the group consisting of piperazinyl, 4-methyl piperazinyl, pyrrolidinyl, imidazolidinyl, imidazolinyl, thiazolidinyl, thiazolinyl, isothiazolidinyl, isothiazolinyl, pyranyl, and morpholinyl; or
a polycyclic heterocycle selected from the group consisting of indolyl, benzthienyl, benzofuranyl, isoindolyl, isobenzothienyl, and isobenzofuranyl;

wherein each alkyl, cycloalkyl, aryl, and heterocycle are each optionally substituted with one or more groups (e.g., 1, 2, or 3 group) which are each independently halogen, CN, $N_3$, $NO_2$, OH, SH, $NH_2$, HONH, HON═, $CO_2H$, $C(O)NH_2$, $S(O)_2OH$, $S(O)_2NH_2$, $C_{1-8}$ alkyl, $R_4O$, $R_4S$, $R_4S(O)$, $R_4S(O)_2$, $R_4NH$, $R_4R_5N$, $R_4ONH$, $R_4ON$═, $R_4C(O)$, $R_4C(Y)O$, $R_4C(Y)S$, $R_4C(Y)NH$, $R_4C(Y)N(R_5)$, $C(Y)OR_4$, $C(Y)SR_4$, $C(Y)NHR_4$, $C(Y)NR_4R_5$, $R_4OC(Y)O$, $R_4OC(Y)S$, $R_4OC(Y)NH$, $R_4OC(Y)NR_5$, $R_4SC(Y)O$, $R_4SC(Y)S$, $R_4SC(Y)NH$, $R_4SC(Y)NR_5$, $R_4NHC(Y)O$, $R_4NHC(Y)S$, $R_4NHC(Y)NH$, $R_4NHC(Y)NR_5$, $R_4R_5NC(Y)O$, $R_4R_5NC(Y)S$, $R_4R_5NC(Y)NH$, $R_4R_5NC(Y)NR_4$, $S(O)_2OR_4$, $S(O)_2SR_4$, $S(O)_2NHR_4$, $S(O)_2NR_4R_5$, H—Y—$(CH_2CH_2O)_m$, $R_4$—Y—$(CH_2CH_2O)_m$, $R_4C(Y)$—O—$(CH_2CH_2O)_m$, $R_4C(Y)$—S—$(CH_2CH_2O)_m$, $R_4C(Y)$—NH—$(CH_2CH_2O)_m$, $R_4C(Y)$—N($R_5$)—$(CH_2CH_2O)_m$, X—$(CH_2CH_2O)_m$, —X—Z, or $R_1$ and $R_2$, $R_1$ and $R_3$ taken together with the carbon atoms to which they are attached form a cyclo($C_{3-9}$)alkyl, aryl, or heterocycle, wherein each alkyl, cycloalkyl, aryl, and heterocycle are each optionally substituted with one or more groups as previously defined;

$R_4$ and $R_5$ above are independently selected from a straight or branched $C_{1-8}$ alkyl, aryl-$C_{1-8}$ alkyl, heterocycle-$C_{1-8}$ alkyl, cyclo($C_{3-9}$)alkyl, aryl, heterocycle, or $R_4$ and $R_5$ taken together with the nitrogen atom to which they are attached form a cyclo($C_{3-9}$)alkyl, aryl, or heterocycle, wherein each alkyl, cycloalkyl, aryl, and heterocycle are each optionally substituted with one or more groups as previously defined;

each Y is independently selected from O, S, NH, $NR_4$, wherein $R_4$ is defined as above;

each Z is selected from OH, SH, NCS, NCO, $NHR_6$, $CONR_4R_5$, $CONHR_6$, $CO_2R_6$, $C(O)SR_6$, $C(O)R_6$, where $R_4$ and $R_5$ are defined as above; $R_6$ is H, $C_{1-8}$ alkyl, cyclo($C_{3-9}$)alkyl, aryl, or heterocycle, wherein each alkyl, cycloalkyl, aryl, and heterocycle are each optionally substituted with one or more groups as previously defined;

$R_7$, $R_8$ are independently selected from H, deuterium, and F; or $R_7$ and $R_8$ can be taken together to form ═O and ═S;

$Y_2$ is independently selected from $CH_2$, O, S, NH, and $NR_4$; wherein $R_4$ is defined as above;

each X is a spacer independently selected from:
$[C(O)]_n$—$W_o$—$[C(O)]_p$—$\{Y_1$—$[C(O)]_q$—$W_r\}_s$—$[C(O)]_q$-$(AA)_t$-,
$[C(O)]_n$—$W_o$—$[C(O)]_p$—$[Y_1$—$(CH_2CH_2O)_m]_u$—$W_r$—$[C(O)]_q$-$(AA)_t$-,
$[C(O)]_n$—$W_o$—$[C(O)]_p$—$[Y_1$—$(CH_2CH_2O)_m]_u$—$[C(O)]_q$—$W_r$-$(AA)_t$-,
$[C(O)]_n$—$W_o$—$[C(O)]_p$—$[Y_1$—$(CH_2CH_2O)_m]_u$—$C(O)$—$Y_1$—$W_r$-$(AA)_t$-,
$[C(O)]_n$—$W_o$—$[C(O)]_p$—$[Y_1$—$(CH_2CH_2O)_m]_u$—$W_r$—$C(O)$—$Y_1$—$W_r$-$(AA)_t$-, $[C(O)]_n-W_o-[C(O)]_p-[Y_1-(CH_2CH_2O)_m]_u-W_r-Y_1-[C(O)]_q-W_r-(AA)_t-,$ $[C(O)]_n-W_o-[C(O)]_p-[Y_1-(CH_2CH_2O)_m]_u-W_r-Y_1-C(O)-Y_1-W_r-(AA)_t-,$ $[C(O)]_n-W_o-[C(O)]_p-[Y_1-(CH_2CH_2O)_m]_u-(AA)_t-[Y_1-(CH_2CH_2O)_m]_u-W_r-,$ $[C(O)]_n-W_o-[C(O)]_p-\{Y_1-[C(O)]_q-W_r\}_s-(AA)-\{Y_1-[C(O)]_q-W_r\}_s-[Y_1-(CH_2CH_2O)_m]_u-[C(O)]_q-W_r-(AA)_t-,$ $[C(O)]_n-W_o-[C(O)]_p-\{Y_1-[C(O)]_q-W_r\}_s-(AA)-C(O)-\{Y_1-[C(O)]_q-W_r\}_s-[Y_1-(CH_2CH_2O)_m]_u-[C(O)]_q-W_r-(AA)_t-,$ $[C(O)]_n-W_o-[C(O)]_p-\{Y_1-[C(O)]_q-W_r\}_s-(AA)-\{Y_1-[C(O)]_q-W_r\}_s-C(O)-[Y_1-(CH_2CH_2O)_m]_u-[C(O)]_q-W_r-(AA)_t-,$ wherein each W is selected from a straight or branched $C_{1-8}$ alkyl, aryl-$C_{1-8}$ alkyl, heterocycle-$C_{1-8}$ alkyl, cyclo($C_{3-9}$)alkyl, aryl, or heterocycle, wherein each alkyl, cycloalkyl, aryl, and heterocycle are each optionally substituted with one or more groups as previously defined;

each AA is an amino acid residue sequence independently selected from the group, consisting of alanine, glycine, isoleucine, leucine, methionine, phenylalanine, proline, tryptophan, valine, lysine, lysine protected with acetyl or formyl, arginine, arginine protected with tosyl or nitro groups, histidine, ornithine, ornithine protected with acetyl or formyl, citrulline, and combinations thereof;

each m is an integer independently selected from 1 to 20;

each n, o, p, q, r and t is an integer independently selected from 0 and 1; when o is 0, n and p cannot be 1;

each s is an integer selected from 0 to 8;

each u is an integer selected from 1 to 8;

$X_1$ and $X_2$ are independently selected from H, deuterium, —X—Z, wherein X and Z are defined as above, or $X_1$ and $X_2$ taken together can form a cyclic ring;

each $Y_1$ is selected from O, S, NH, $NR_4$, N—$[C(O)]_q$—$W_r$—X—Z, wherein $R_4$, W, X, Z, r and q are defined as above;

with a proviso that, when $R_1$ and $R_3$ are both H and s is 0, $R_7$ and $R_8$ together cannot be =O in Formula II;

with a drug (D) payload via group Z of the LK and a functional group of D to form a Linker-Drug conjugate compound selected from the formulae

  (IV)

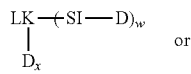  (V)

or

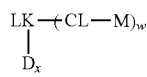  (VI)

wherein

LK is a linker moiety selected from Formula I, II or III;

D is a drug moiety independently selected from the group selected from doxorubicin, vincristine, monomethyl auristatin E, monomethyl auristatin F, monomethyl dolastatin 10, maytansinoids, and calicheamicin;

M is a radioisotope selected from $^{211}$At, $^{225}$Ac, $^{213}$Bi, $^{60}$Co, $^{125}$I, $^{131}$I, $^{111}$In, $^{177}$Lu, $^{32}$P, $^{223}$Ra, $^{186}$Re, $^{188}$Re, $^{153}$Sm, $^{227}$Th and $^{90}$Y;

SI is a tethering group or self-immolative moiety that, upon a single activation event when internalized by the target cell or on the target cell surface, leads to a spontaneous and rapid release of the fully active drug;

CL is a metal chelating moiety that is able to chelate and hold the radioisotope and prevent it from premature release and off-target cell destruction;

a is an integer selected from 1 to 10;

v and w are integers independently selected from 1 to 10;

x is an integer selected from 0 to 9; provided that the sum of w and x does not exceed 10; and (b) reacting a sulfhydryl or thiol group (—SH) on the ligand (LG) moiety with the double bond on the Linker-Drug conjugate compound selected from Formula IV, V or VI to form a Ligand-Linker-Drug conjugate compound selected from the formulae

  (VII)

  (VIII)

or

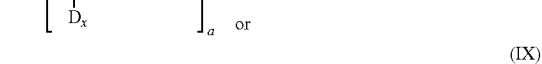  (IX)

wherein

D, SI, CL M, a, v, w and x are defined above;

LK is a linker moiety selected from Formula I, II or III and covalently attached to a ligand (LG) through a thioether bond formed between a sulfhydryl or thiol group (—SH) on the LG with the double bond of the LK; and LG is selected from abciximab, adalimumab, alemtuzumab, basiliximab, belimumab, bevacizumab, brentuximab, canakinumab, certolizumab, cetuximab, daclizumab, denosumab, eculizumab, efalizumab, gemtuzumab, golimumab, ibritumomab, infliximab, ipilimumab, motavizumab, muronomab-CD3, natalizumab, ofatumumab, omalizumab, palivizumab, panitumumab, raxibacumab, ranibizumab, rituximab, tocilizumab, tositumomab, trastuzumab, ustekinumab, anti-CD30 antibody cAC10, RGD-peptide homing ligands, 2-[3(1,3-dicarboxypropyl)-ureido]pentanedioic acid (DUPA) targeting prostate specific membrane antigen (PSMA), epidermal growth factor, vascular endothelial growth factor, steroidal estrogens, somatostatin, bombesin, polyunsaturated fatty acids, lectins, folate, biotin, riboflavin, hyaluronic acid, and transferrin. In a particular embodiment of this aspect, each X is a spacer. In another embodiment of this aspect, each X is non-cleavable spacer when the conjugates contain radioisotopes.

In certain embodiments of this aspect, in step (a), wherein the said Linker-Drug conjugate compound of Formula IV, V or VI is formed between the functional group Z present in a linker compound of Formula I, II or III and a functional group, either natively present or chemically introduced, in the drug moiety selected from primary or secondary amine, hydroxyl, sulfhydryl, carboxyl, aldehyde or ketone via a covalent bond by esterification, amidation, reductive amination or aldol reaction.

In other certain embodiments of this aspect, in step (b) proceeds either under UV irradiation at wavelength of 254 or 365 nm, or via thermal reaction, in the presence of initiator selected from the group consisting of diphenyl 2,4,6-trimethylbenzoyl phosphine oxide, 2,2-dimethoxy-2-phenylacetophenone, benzophenone, DL-Camphorquinone, dimethyl phenyl phosphine,

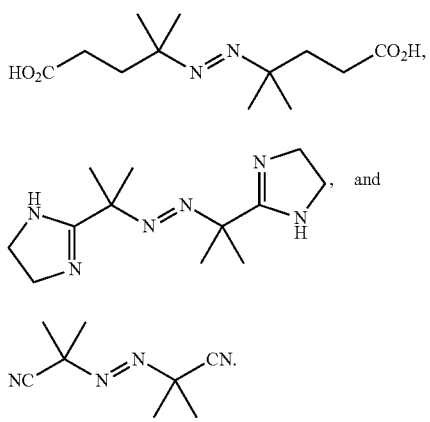

(ACVA)

(VA-044), and (AIBN)

Another aspect of the disclosure provides Ligand-Linker-Drug conjugate compound of the formulae

  (VII)

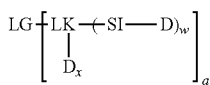  (VIII)

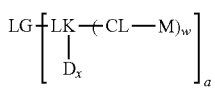  (IX)

or a pharmaceutically acceptable salt thereof, wherein

LG is selected from the group consisting of abciximab, adalimumab, alemtuzumab, basiliximab, belimumab, bevacizumab, brentuximab, canakinumab, certolizumab, cetuximab, daclizumab, denosumab, eculizumab, efalizumab, gemtuzumab, golimumab, ibritumomab, infliximab, ipilimumab, motavizumab, muronomab-CD3, natalizumab, ofatumumab, omalizumab, palivizumab, panitumumab, raxibacumab, ranibizumab, rituximab, tocilizumab, tositumomab, trastuzumab, ustekinumab, anti-CD30 antibody cAC10, RGD-peptide homing ligands, 2-[3(1,3-dicarboxypropyl)-ureido]pentanedioic acid (DUPA) targeting prostate specific membrane antigen (PSMA), epidermal growth factor, vascular endothelial growth factor, steroidal estrogens, somatostatin, bombesin, polyunsaturated fatty acids, lectins, folate, biotin, riboflavin, hyaluronic acid, and transferrin;

LK is a linker moiety selected from Formula I, II or III and covalently attached to a ligand (LG) moiety through a thioether bond formed between a sulfhydryl or thiol group (—SH) on the LG moiety with the double bond on the LK:

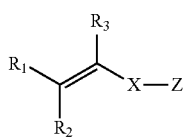  (I)

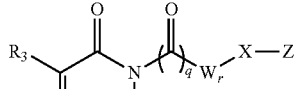  (II)

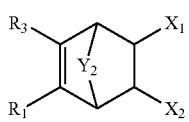  (III)

wherein $R_1$, $R_2$ and $R_3$ are independently selected from H, deuterium, halogen, CN, $NO_2$, HC(O), $CO_2H$, $C(O)NH_2$, $S(O)_2OH$, $S(O)_2NH_2$, a straight or branched $C_{1-8}$ alkyl, aryl-$C_{1-8}$ alkyl, heterocycle-$C_{1-8}$ alkyl, cyclo($C_{3-9}$)alkyl, aryl, heterocycle, $R_4C(O)$, $R_4O$, $R_4S$, $R_4S(O)$, $R_4S(O)_2$, $R_4NH$, $R_4R_5N$, $C(Y)OR_4$, $C(Y)SR_4$, $C(Y)NHR_4$, $C(Y)NR_4R_5$, $R_4OC(Y)$, $R_4SC(Y)$, $R_4NHC(Y)$, $R_4R_5NC(Y)$, $R_4OS(O)_2$, H—Y—$(CH_2CH_2O)_m$, $R_4$—Y—$(CH_2CH_2O)_m$, $R_4C(Y)$—O—$(CH_2CH_2O)_m$, $R_4C(Y)$—S—$(CH_2CH_2O)_m$, $R_4C(Y)$—NH—$(CH_2CH_2O)_m$, $R_4C(Y)$—N($R_5$)—$(CH_2CH_2O)_m$, or —X—Z, wherein the aryl comprises phenyl or naphthyl;

the heterocycle comprises a 5 or 6 membered aromatic heterocycle selected from the group consisting of pyridyl, diazinyl, pyrimidinyl, 5-methoxy pyrimidinyl, (1,2,4)triazine-3,5-dione-6-yl, 6-mercaptopyrimidine-4-yl, pyrrolyl, pyrazolyl, imidazolyl, oxazolyl, isoxazolyl, thiazolyl, isothiazolyl, furanyl, and thienyl;

a 3 to 9 membered non-aromatic heterocycle selected from the group consisting of piperazinyl, 4-methyl piperazinyl, pyrrolidinyl, imidazolidinyl, imidazolinyl, thiazolidinyl, thiazolinyl, isothiazolidinyl, isothiazolinyl, pyranyl, and morpholinyl; or a polycyclic heterocycle selected from the group consisting of indolyl, benzthienyl, benzofuranyl, isoindolyl, isobenzothienyl, and isobenzofuranyl;

wherein each alkyl, cycloalkyl, aryl, and heterocycle are each optionally substituted with one or more groups (e.g., 1, 2, or 3 group) which are each independently halogen, CN, $N_3$, $NO_2$, OH, SH, $NH_2$, HONH, HON=, $CO_2H$, $C(O)NH_2$, $S(O)_2OH$, $S(O)_2NH_2$, $C_{1-8}$ alkyl, $R_4O$, $R_4S$, $R_4S(O)$, $R_4S(O)_2$, $R_4NH$, $R_4R_5N$, $R_4ONH$, $R_4ON=$, $R_4C(O)$, $R_4C(Y)O$, $R_4C(Y)S$, $R_4C(Y)NH$, $R_4C(Y)N(R_5)$, $C(Y)OR_4$, $C(Y)SR_4$, $C(Y)NHR_4$, $C(Y)NR_4R_5$, $R_4OC(Y)O$, $R_4OC(Y)S$, $R_4OC(Y)NH$, $R_4OC(Y)NR_5$, $R_4SC(Y)O$, $R_4SC(Y)S$, $R_4SC(Y)NH$, $R_4SC(Y)NR_5$, $R_4NHC(Y)O$, $R_4NHC(Y)S$, $R_4NHC(Y)NH$, $R_4NHC(Y)NR_5$, $R_4R_5NC(Y)O$, $R_4R_5NC(Y)S$, $R_4R_5NC(Y)NH$, $R_4R_5NC(Y)NR_4$, $S(O)_2OR_4$, $S(O)_2SR_4$, $S(O)_2NHR_4$, $S(O)_2NR_4R_5$, H—Y—$(CH_2CH_2O)_m$, $R_4$—Y—$(CH_2CH_2O)_m$, $R_4C(Y)$—O—$(CH_2CH_2O)_m$, $R_4C(Y)$—S—$(CH_2CH_2O)_m$, $R_4C(Y)$—NH—$(CH_2CH_2O)_m$, $R_4C(Y)$—N($R_5$)—$(CH_2CH_2O)_m$, X—$(CH_2CH_2O)_m$, —X—Z, or $R_1$ and $R_2$, $R_1$ and $R_3$ taken together with the carbon atoms to which they are attached form a cyclo($C_{3-9}$)alkyl, aryl, or heterocycle, wherein each alkyl, cycloalkyl, aryl, and heterocycle are each optionally substituted with one or more groups as previously defined;

$R_4$ and $R_5$ above are independently selected from a straight or branched $C_{1-8}$ alkyl, aryl-$C_{1-8}$ alkyl, heterocycle-$C_{1-8}$ alkyl, cyclo($C_{3-9}$)alkyl, aryl, heterocycle, or $R_4$ and $R_5$ taken together with the nitrogen atom to which they are attached form a cyclo($C_{3-9}$)alkyl, aryl, or heterocycle, wherein each alkyl, cycloalkyl, aryl, and heterocycle are each optionally substituted with one or more groups as previously defined;

each Y is independently selected from O, S, NH, $NR_4$, wherein $R_4$ is defined as above;

each Z is selected from OH, SH, NCS, NCO, $NHR_6$, $CONR_4R_5$, $CONHR_6$, $CO_2R_6$, $C(O)SR_6$, $C(O)R_6$, where $R_4$ and $R_5$ are defined as above; $R_6$ is H, $C_{1-8}$ alkyl, cyclo($C_{3-9}$) alkyl, aryl, or heterocycle, wherein each alkyl, cycloalkyl, aryl, and heterocycle are each optionally substituted with one or more groups as previously defined;

$R_7$, $R_8$ are independently selected from H, deuterium, and F; or $R_7$ and $R_8$ can be taken together to form $=O$ and $=S$;

$Y_2$ is independently selected from $CH_2$, O, S, NH, and $NR_4$; wherein $R_4$ is defined as above;

each X is a spacer independently selected from:

$[C(O)]_n-W_o-[C(O)]_p-\{Y_1-[C(O)]_q-W_r\}_s-[C(O)]_q-(AA)_t-$, $[C(O)]_n-W_o-[C(O)]_p-[Y_1-(CH_2CH_2O)_m]_u-W_r-[C(O)]_q-(AA)_t-$, $[C(O)]_n-W_o-[C(O)]_p-[Y_1-(CH_2CH_2O)_m]_u-[C(O)]_q-W_r-(AA)_t-$, $[C(O)]_n-W_o-[C(O)]_p-[Y_1-(CH_2CH_2O)_m]_u-C(O)-Y_1-W_r-(AA)_t-$, $[C(O)]_n-W_o-[C(O)]_p-[Y_1-(CH_2CH_2O)_m]_u-W_r-C(O)-Y_1-W_r-(AA)_t-$, $[C(O)]_n-W_o-[C(O)]_p-[Y_1-(CH_2CH_2O)_m]_u-W_r-Y_1-[C(O)]_q-W_r-(AA)_t-$, $[C(O)]_n-W_o-[C(O)]_p-[Y_1-(CH_2CH_2O)_m]_u-W_r-Y_1-C(O)-Y_1-W_r-(AA)_t-$, $[C(O)]_n-W_o-[C(O)]_p-[Y_1-(CH_2CH_2O)_m]_u-(AA)_t-[Y_1-(CH_2CH_2O)_m]_u-W_r-$, $[C(O)]_n-W_o-[C(O)]_p-\{Y_1-[C(O)]_q-W_r\}_s-(AA)-\{Y_1-[C(O)]_q-W_r\}_s-[Y_1-(CH_2CH_2O)_m]_u-[C(O)]_q-W_r-(AA)_t-$, $[C(O)]_n-W_o-[C(O)]_p-\{Y_1-[C(O)]_q-W_r\}_s-(AA)-C(O)-\{Y_1-[C(O)]_q-W_r\}_s-[Y_1-(CH_2CH_2O)_m]_u-[C(O)]_q-W_r-(AA)_t-$, $[C(O)]_n-W_o-[C(O)]_p-\{Y_1-[C(O)]_q-W_r\}_s-(AA)-\{Y_1-[C(O)]_q-W_r\}_s-C(O)-[Y_1-(CH_2CH_2O)_m]_u-[C(O)]_q-W_r-(AA)_t-$, wherein each W is selected from a straight or branched $C_{1-8}$ alkyl, aryl-$C_{1-8}$ alkyl, heterocycle-$C_{1-8}$ alkyl, cyclo($C_{3-9}$)alkyl, aryl, or heterocycle, wherein each alkyl, cycloalkyl, aryl, and heterocycle are each optionally substituted with one or more groups as previously defined;

each AA is an amino acid residue sequence independently selected from the group, consisting of alanine, glycine, isoleucine, leucine, methionine, phenylalanine, proline, tryptophan, valine, lysine, lysine protected with acetyl or formyl, arginine, arginine protected with tosyl or nitro groups, histidine, ornithine, ornithine protected with acetyl or formyl, citrulline, and combinations thereof;

each m is an integer independently selected from 1 to 20;

each n, o, p, q, r and t is an integer independently selected from 0 and 1; when o is 0, n and p cannot be 1;

each s is an integer independently selected from 0 to 8;

each u is an integer independently selected from 1 to 8;

$X_1$ and $X_2$ are independently selected from H, deuterium, —X—Z, wherein X and Z are defined as above, or $X_1$ and $X_2$ taken together can form a cyclic ring;

each $Y_1$ is selected from O, S, NH, $NR_4$, N—$[C(O)]_q$—$W_r$—X—Z, wherein $R_4$, W, X, Z, r and q are defined as above;

with a proviso that, when $R_1$ and $R_3$ are both H and s is 0, $R_7$ and $R_8$ together cannot be $=O$ in Formula II;

D is a drug moiety independently selected from the group consisting of doxorubicin, vincristine, monomethyl auristatin E, monomethyl auristatin F, monomethyl dolastatin 10, maytansinoids, and calicheamicin;

M is a radioisotope selected from $^{211}$At, $^{225}$Ac, $^{213}$Bi, $^{60}$Co, $^{125}$I, $^{131}$I, $^{111}$In, $^{177}$Lu, $^{32}$P, $^{223}$Ra, $^{186}$Re, $^{188}$Re, $^{153}$Sm, $^{227}$Th and $^{90}$Y;

SI is a tethering group or self-immolative moiety that, upon a single activation event when internalized by the target cell or on the target cell surface, leads to a spontaneous and rapid release of the fully active drug;

CL is a metal chelating moiety that is able to chelate and hold the radioisotope and prevent it from premature release and off-target cell destruction;

a is an integer selected from 1 to 10;

v and w are integers independently selected from 1 to 10;

x is an integer selected from 0 to 9; provided the sum of w and x does not exceed 10.

Specific, non limiting examples of the Ligand-Linker-Drug conjugate compound include:

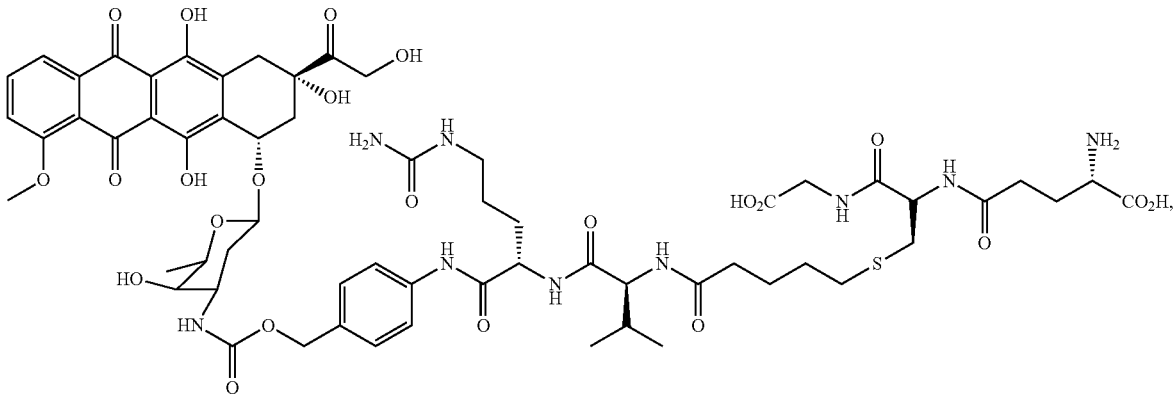

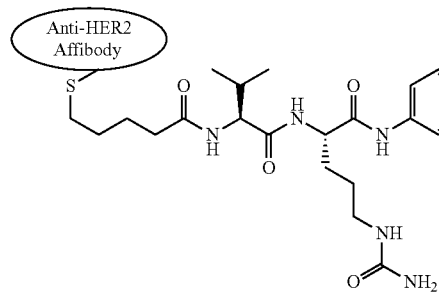

-continued

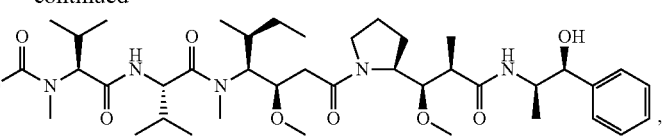

or a pharmaceutically acceptable salt thereof.

Another aspect of the disclosure provides a Linker-Drug conjugate compound of the formulae $$LK-D_y \quad (IV)$$

$$LK\!-\!(SI\!-\!D)_w \atop | \atop D_x \quad (V)$$

$$LK\!-\!(CL\!-\!M)_w \atop | \atop D_x \quad (VI)$$

or a pharmaceutically acceptable salt thereof, wherein
LK is a linker moiety selected from Formula I, II or III

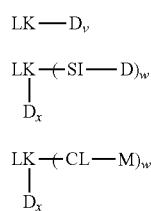 (I)

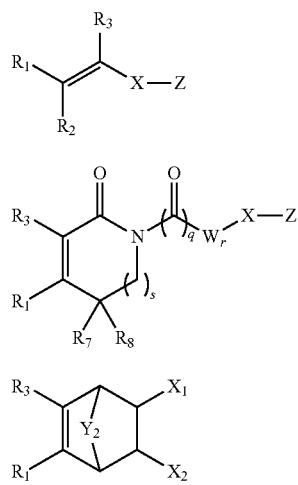

wherein $R_1$, $R_2$ and $R_3$ are independently selected from H, deuterium, halogen, CN, $NO_2$, HC(O), $CO_2H$, $C(O)NH_2$, $S(O)_2OH$, $S(O)_2NH_2$, a straight or branched $C_{1-8}$ alkyl, aryl-$C_{1-8}$ alkyl, heterocycle-$C_{1-8}$ alkyl, cyclo($C_{3-9}$)alkyl, aryl, heterocycle, $R_4C(O)$, $R_4O$, $R_4S$, $R_4S(O)$, $R_4S(O)_2$, $R_4NH$, $R_4R_5N$, $C(Y)OR_4$, $C(Y)SR_4$, $C(Y)NHR_4$, $C(Y)NR_4R_5$, $R_4OC(Y)$, $R_4SC(Y)$, $R_4NHC(Y)$, $R_4R_5NC(Y)$, $R_4OS(O)_2$, H—Y—$(CH_2CH_2O)_m$, $R_4$—Y—$(CH_2CH_2O)_m$, $R_4C(Y)$—O—$(CH_2CH_2O)_m$, $R_4C(Y)$—S—$(CH_2CH_2O)_m$, $R_4C(Y)$—NH—$(CH_2CH_2O)_m$, $R_4C(Y)$—N($R_5$)—$(CH_2CH_2O)_m$, or —X—Z, wherein the aryl comprises phenyl or naphthyl;

the heterocycle comprises a 5 or 6 membered aromatic heterocycle selected from the group consisting of pyridyl, diazinyl, pyrimidinyl, 5-methoxy pyrimidinyl, (1,2,4)triazine-3,5-dione-6-yl, 6-mercaptopyrimidine-4-yl, pyrrolyl, pyrazolyl, imidazolyl, oxazolyl, isoxazolyl, thiazolyl, isothiazolyl, furanyl, and thienyl;

a 3 to 9 membered non-aromatic heterocycle selected from the group consisting of piperazinyl, 4-methyl piperazinyl, pyrrolidinyl, imidazolidinyl, imidazolinyl, thiazolidinyl, thiazolinyl, isothiazolidinyl, isothiazolinyl, pyranyl, and morpholinyl; or a polycyclic heterocycle selected from the group consisting of indolyl, benzthienyl, benzofuranyl, isoindolyl, isobenzothienyl, and isobenzofuranyl;

wherein each alkyl, cycloalkyl, aryl, and heterocycle are each optionally substituted with one or more groups (e.g., 1, 2, or 3 group) which are each independently halogen, CN, $N_3$, $NO_2$, OH, SH, $NH_2$, HONH, HON=, $CO_2H$, $C(O)NH_2$, $S(O)_2OH$, $S(O)_2NH_2$, $C_{1-8}$ alkyl, $R_4O$, $R_4S$, $R_4S(O)$, $R_4S(O)_2$, $R_4NH$, $R_4R_5N$, $R_4ONH$, $R_4ON=$, $R_4C(O)$, $R_4C(Y)O$, $R_4C(Y)S$, $R_4C(Y)NH$, $R_4C(Y)N(R_5)$, $C(Y)OR_4$, $C(Y)SR_4$, $C(Y)NHR_4$, $C(Y)NR_4R_5$, $R_4OC(Y)O$, $R_4OC(Y)S$, $R_4OC(Y)NH$, $R_4OC(Y)NR_5$, $R_4SC(Y)O$, $R_4SC(Y)S$, $R_4SC(Y)NH$, $R_4SC(Y)NR_5$, $R_4NHC(Y)O$, $R_4NHC(Y)S$, $R_4NHC(Y)NH$, $R_4NHC(Y)NR_5$, $R_4R_5NC(Y)O$, $R_4R_5NC(Y)S$, $R_4R_5NC(Y)NH$, $R_4R_5NC(Y)NR_4$, $S(O)_2OR_4$, $S(O)_2SR_4$, $S(O)_2NHR_4$, $S(O)_2NR_4R_5$, H—Y—$(CH_2CH_2O)_m$, $R_4$—Y—$(CH_2CH_2O)_m$, $R_4C(Y)$—O—$(CH_2CH_2O)_m$, $R_4C(Y)$—S—$(CH_2CH_2O)_m$, $R_4C(Y)$—NH—$(CH_2CH_2O)_m$, $R_4C(Y)$—N($R_5$)—$(CH_2CH_2O)_m$, X—$(CH_2CH_2O)_m$, —X—Z, or $R_1$ and $R_2$, $R_1$ and $R_3$ taken together with the carbon atoms to which they are attached form a cyclo($C_{3-9}$)alkyl, aryl, or heterocycle, wherein each alkyl, cycloalkyl, aryl, and heterocycle are each optionally substituted with one or more groups as previously defined;

$R_4$ and $R_5$ above are independently selected from a straight or branched $C_{1-8}$ alkyl, aryl-$C_{1-8}$ alkyl, heterocycle-$C_{1-8}$ alkyl, cyclo($C_{3-9}$)alkyl, aryl, heterocycle, or $R_4$ and $R_5$ taken together with the nitrogen atom to which they are attached form a cyclo($C_{3-9}$)alkyl, aryl, or heterocycle, wherein each alkyl, cycloalkyl, aryl, and heterocycle are each optionally substituted with one or more groups as previously defined;

each Y is independently selected from O, S, NH, $NR_4$, wherein $R_4$ is defined as above;

each Z is selected from OH, SH, NCS, NCO, $NHR_6$, $CONR_4R_5$, $CONHR_6$, $CO_2R_6$, $C(O)SR_6$, $C(O)R_6$, where $R_4$ and $R_5$ are defined as above; $R_6$ is H, $C_{1-8}$ alkyl, cyclo($C_{3-9}$) alkyl, aryl, or heterocycle, wherein each alkyl, cycloalkyl, aryl, and heterocycle are each optionally substituted with one or more groups as previously defined;

R$_7$, R$_8$ are independently selected from H, deuterium, and F; or R$_7$ and R$_8$ can be taken together to form =O and =S;

Y$_2$ is independently selected from CH$_2$, O, S, NH, and NR$_4$; wherein R$_4$ is defined as above;

each X is a spacer independently selected from:

[C(O)]$_n$—W$_o$—[C(O)]$_p$—{Y$_1$—[C(O)]$_q$—W$_r$}$_s$—[C(O)]$_q$-(AA)$_t$-,

[C(O)]$_n$—W$_o$—[C(O)]$_p$—[Y$_1$—(CH$_2$CH$_2$O)$_m$]$_u$—W$_r$—[C(O)]$_q$-(AA)$_t$-,

[C(O)]$_n$—W$_o$—[C(O)]$_p$—[Y$_1$—(CH$_2$CH$_2$O)$_m$]$_u$—[C(O)]$_q$—W$_r$-(AA)$_t$-,

[C(O)]$_n$—W$_o$—[C(O)]$_p$—[Y$_1$—(CH$_2$CH$_2$O)$_m$]$_u$—C(O)—Y$_1$—W$_r$-(AA)$_t$-,

[C(O)]$_n$—W$_o$—[C(O)]$_p$—[Y$_1$—(CH$_2$CH$_2$O)$_m$]$_u$—W$_r$—C(O)—Y$_1$—W$_r$-(AA)$_t$-,

[C(O)]$_n$—W$_o$—[C(O)]$_p$—[Y$_1$—(CH$_2$CH$_2$O)$_m$]$_u$—W$_r$—Y$_1$—[C(O)]$_q$—W$_r$-(AA)$_t$-,

[C(O)]$_n$—W$_o$—[C(O)]$_p$—[Y$_1$—(CH$_2$CH$_2$O)$_m$]$_u$—W$_r$—Y$_1$—C(O)—Y$_1$—W$_r$-(AA)$_t$-,

[C(O)]$_n$—W$_o$—[C(O)]$_p$—[Y$_1$—(CH$_2$CH$_2$O)$_m$]$_u$-(AA)$_t$-[Y$_1$—(CH$_2$CH$_2$O)$_m$]$_u$—W$_r$—,

[C(O)]$_n$—W$_o$—[C(O)]$_p$—{Y$_1$—[C(O)]$_q$—W$_r$}$_s$-(AA)-{Y$_1$—[C(O)]$_q$—W$_r$}$_s$—[Y$_1$—(CH$_2$CH$_2$O)$_m$]$_u$—[C(O)]$_q$—W$_r$-(AA)$_t$-,

[C(O)]$_n$—W$_o$—[C(O)]$_p$—{Y$_1$—[C(O)]$_q$—W$_r$}$_s$-(AA)-C(O)—{Y$_1$—[C(O)]$_q$—W$_r$}$_s$—[Y$_1$—(CH$_2$CH$_2$O)$_m$]$_u$—[C(O)]$_q$—W$_r$-(AA)$_t$-,

[C(O)]$_n$—W$_o$—[C(O)]$_p$—{Y$_1$—[C(O)]$_q$—W$_r$}$_s$-(AA)-{Y$_1$—[C(O)]$_q$—W$_r$}$_s$—C(O)—[Y$_1$—(CH$_2$CH$_2$O)$_m$]$_u$—[C(O)]$_q$—W$_r$-(AA)$_t$-, wherein each W is selected from a straight or branched C$_{1-8}$ alkyl, aryl-C$_{1-8}$ alkyl, heterocycle-C$_{1-8}$ alkyl, cyclo(C$_{3-9}$)alkyl, aryl, or heterocycle, wherein each alkyl, cycloalkyl, aryl, and heterocycle are each optionally substituted with one or more groups as previously defined;

each AA is an amino acid residue sequence independently selected from the group, consisting of alanine, glycine, isoleucine, leucine, methionine, phenylalanine, proline, tryptophan, valine, lysine, lysine protected with acetyl or formyl, arginine, arginine protected with tosyl or nitro groups, histidine, ornithine, ornithine protected with acetyl or formyl, citrulline, and combinations thereof;

each m is an integer independently selected from 1 to 20;

each n, o, p, q, r and t is an integer independently selected from 0 and 1; when o is 0, n and p cannot be 1;

each s is an integer independently selected from 0 to 8;

each u is an integer independently selected from 1 to 8;

X$_1$ and X$_2$ are independently selected from H, deuterium, —X—Z, wherein X and Z are defined as above, or X$_1$ and X$_2$ taken together can form a cyclic ring;

each Y$_1$ is selected from O, S, NH, NR$_4$, N—[C(O)]$_q$—W$_r$—X—Z, wherein R$_4$, W, X, Z, r and q are defined as above;

with a proviso that, when R$_1$ and R$_3$ are both H and s is 0, R$_7$ and R$_8$ together cannot be =O in Formula II;

D is a drug moiety independently selected from doxorubicin, vincristine, monomethyl auristatin E, monomethyl auristatin F, monomethyl dolastatin 10, maytansinoids, and calicheamicin;

M is a radioisotope selected from $^{211}$At, $^{225}$Ac, $^{213}$Bi, $^{60}$Co, $^{125}$I, $^{131}$I, $^{111}$In, $^{177}$Lu, $^{32}$P, $^{223}$Ra, $^{186}$Re, $^{188}$Re, $^{153}$Sm, $^{227}$Th and $^{90}$Y;

SI is a tethering group or self-immolative moiety that, upon a single activation event when internalized by the target cell or on the target cell surface, leads to a spontaneous and rapid release of the fully active drug;

CL is a metal chelating moiety that is able to chelate and hold the radioisotope and prevent it from premature release and off-target cell destruction;

a is an integer selected from 1 to 10;

v and w are integers independently selected from 1 to 10;

x is an integer selected from 0 to 9, provided that the sum of w and x does not exceed 10.

Specific, non limiting examples of the Linker-Drug conjugate compound include:

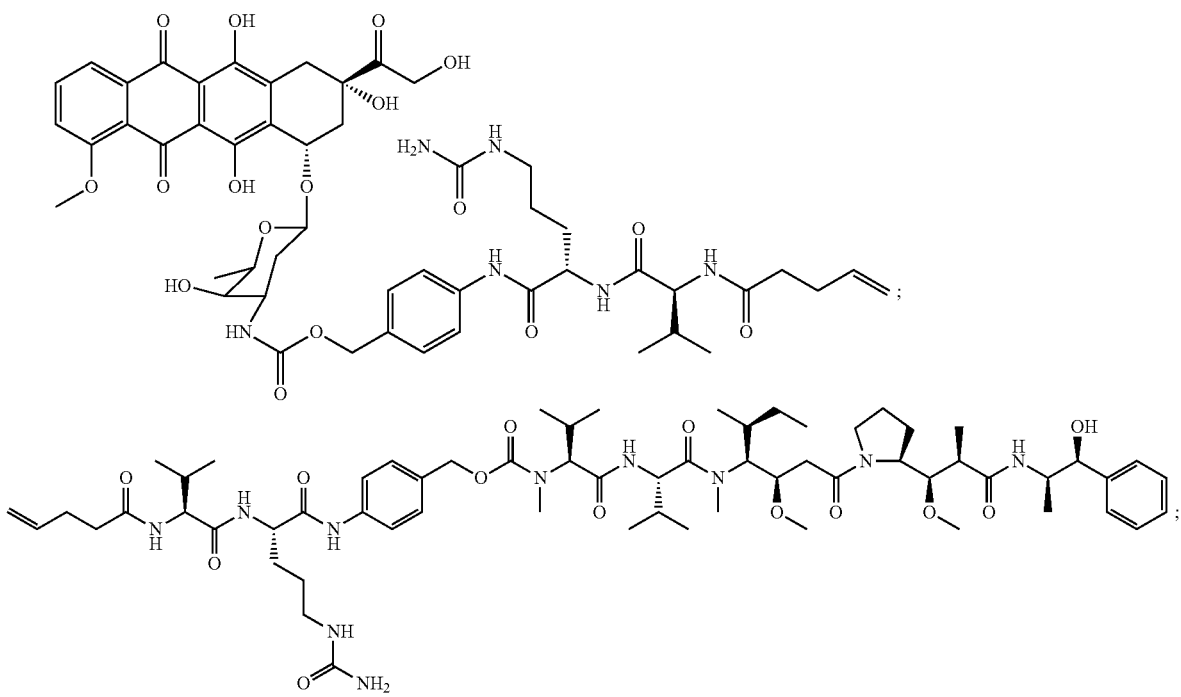

or a pharmaceutically acceptable salt thereof.

In yet another aspect, the present invention provides compositions and methods which may utilize effective amount of Linker-Drug compounds or Ligand-Linker-Drug conjugates, or a pharmaceutically acceptable salt or solvate thereof, represented by the general formulae IV to IX, to target cell population and to treat, prevent or diagnose diseases, such as cancers, autoimmune diseases, inflammatory conditions, central nervous system disorders and infections. Thus, the disclosure provides compositions comprising the compounds of the disclosure and a pharmaceutically acceptable carrier, excipient, or diluent. The disclosure also provides methods of treating or preventing cancer, an autoimmune disease, an inflammatory condition, a central nervous system disorder or an infection in a patient, said method comprising administering to a patient an effective amount of a compound of the disclosure.

The invention will best be understood by reference to the following detailed description of exemplary embodiments, taken in conjunction with the accompanying drawings, figures and schemes. The description below is illustrative and exemplary and is not to be taken as limiting the scope defined by any appended claims.

DETAILED DESCRIPTION OF THE INVENTION

As used in the present specification, scientific and technical terms used in connection with the present invention shall have the meanings that are commonly understood by those of ordinary skill in the art. The language used herein is intended to be given the broadest possible scope and meaning; the phraseology and terminology employed herein is to be understood for the purpose of description and should not be regarded as limiting. The embodiments are meant to be exemplary and not exhaustive. The invention is also capable of other embodiments or of being practiced or carried out in various ways. As such, the following words and phrases are generally intended to have the meanings as set forth below, except to the extent that the context in which they are used indicates otherwise or they are expressly defined to mean something different.

When trade names are used, it is intended to independently include the trade name product formulation, the generic drug and the active pharmaceutical ingredient(s) of the trade name product.

In chemical structures, the symbol "—" means a single bond, "=" means a double bond, "≡" means a triple bond, "⹀" means a single or double bond.

When chemical structures are depicted or described, unless explicitly stated otherwise, all carbons are assumed to have hydrogen substitution to conform to a valence of four. For example, in the structure on the left-hand side of the schematic below there are nine hydrogens implied, as depicted in the right-hand structure. Sometimes a particular atom in a structure is described in textual formula as having a hydrogen or hydrogens as substitution (expressly defined hydrogen), for example, —CH$_2$CH$_2$—. It is understood by one of ordinary skill in the art that the aforementioned descriptive techniques are common in the chemical arts to provide brevity and simplicity to description of otherwise complex structures.

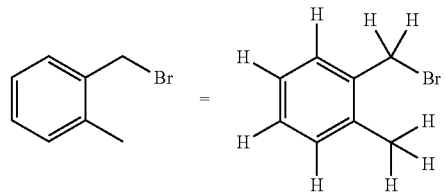

"Alkyl" is intended to include linear, branched, or cyclic hydrocarbon structures and combinations thereof, inclusively. For example, "C$_6$ alkyl" may refer to an n-hexyl, iso-hexyl, cyclobutylethyl, and the like. Lower alkyl refers to alkyl groups of one to six carbon atoms. Examples of lower alkyl groups include methyl, ethyl, propyl, isopropyl, butyl, s-butyl, t-butyl, isobutyl, pentyl, hexyl and the like. Higher alkyl refers to alkyl groups containing more than eight carbon atoms. Exemplary alkyl groups are those of C$_{20}$ or below. Cycloalkyl is a subset of alkyl and includes cyclic hydrocarbon groups of three to thirteen carbon atoms, as further defined below. In this application, alkyl refers to alkanyl, alkenyl, and alkynyl residues (and combinations thereof); it is intended to include cyclohexylmethyl, vinyl, allyl, isoprenyl, and the like. Thus when an alkyl residue having a specific number of carbons is named, all geometric isomers having that number of carbons are intended to be encompassed; thus, for example, either "butyl" or "C$_4$ alkyl" is meant to include n-butyl, sec-butyl, isobutyl, t-butyl, isobutenyl and but-2-ynyl groups; and for example, "propyl" or "C$_3$ alkyl" each include n-propyl, propenyl, and isopropyl. Alkyl also includes unsaturated hydrocarbon groups, such as alkenyl and alkynyl groups each having one or more carbon-carbon double or triple bonds, respectively.

"Alkoxy" or "alkoxyl" refers to the group —O-alkyl, for example, including one to eight carbon atoms of a straight, branched, cyclic configuration, unsaturated chains, and combinations thereof attached to the parent structure through an oxygen atom. Examples include methoxy, ethoxy, propoxy, isopropoxy, cyclopropyloxy, cyclohexyloxy and the like. Lower-alkoxy refers to groups containing one to six carbons.

"Aryl" refers to aromatic six- to fourteen-membered carbocyclic ring, and includes mono-, bicyclic or polycyclic groups, for example, benzene, naphthalene, acenaphthylene, anthracene, indane, tetralin, fluorene and the like. Aryl as substituents includes univalent or polyvalent substituents. As univalent substituents, the aforementioned ring examples are named, phenyl, naphthyl, acenaphthyl, anthracenyl, indanyl, tetralinyl, and fluorenyl. "Polycyclic aryl" as used herein refers to an aryl ring fused to at least a second aryl ring. Examples of polycyclic aryl include, but are not limited to, naphthyl, anthracenyl, acenaphthylenyl, and phenanthrenyl.

When a group is referred to as "arylalkyl", such as "aryl-C$_1$-C$_8$ alkyl", an aryl moiety is attached to a parent structure via an alkylene group. Examples include benzyl, phenethyl, and the like. Both the aryl and the corresponding alkylene portion of a "C$_1$-C$_8$ alkyl" group may be optionally substituted. In some examples, as appreciated by one of ordinary skill in the art, two adjacent groups on an aromatic system may be fused together to form a ring structure. The fused ring structure may contain heteroatoms and may be optionally substituted with one or more groups. It should additionally be noted that saturated carbons of such fused groups (i.e. saturated ring structures) can contain two substitution groups.

"Cycloalkyl" refers to a "cycloalkanyl", "cycloalkenyl", and "cycloalkynyl" groups, where "cycloalkanyl" refers to fully saturated hydrocarbon rings; "cycloalkenyl" refers to non-aromatic hydrocarbon rings containing at least one carbon-carbon double bond; "cycloalkynyl" refers to non-aromatic hydrocarbon rings containing at least one carbon-carbon triple bond. Each cycloalkyl group can be a monocyclic, fused or bridged bicyclic, fused or bridged tricyclic, fused or bridged polycyclic hydrocarbon group comprising 3 to 14 carbon atoms in the cycloalkyl ring, where the cycloalkyl can be saturated or unsaturated with one or more carbon-carbon double and/or triple bonds between consecutive ring atoms. Examples of cycloalkanyl group include, but are not limited to, cyclopropyl, cyclobutyl, cyclopentyl, cyclohexyl, cyclooctyl, decahydronaphthalenyl, bicyclo[2.2.1]heptanyl, adamantyl, and bicyclo[2.2.2]octanyl. Examples of cycloalkenyl group include, but are not limited to, cyclopentenyl, cyclohexenyl, cyclooctenyl, cyclooctadienyl, octahydronaphthalenyl, norbornenyl, and bicyclo[2.2.2]octenyl. Examples of cycloalkynyl group include, but are not limited to, cyclooctynyl and cyclodecynyl.

"Fused-polycyclic" or "fused ring system" refers to a polycyclic ring system that contains bridged or fused rings, that is, where two rings have more than one shared atom in their ring structures. In this application, fused-polycyclics and fused ring systems are not necessarily all aromatic ring systems. Typically, but not necessarily, fused-polycyclics share a vicinal set of atoms, for example naphthalene or 1,2,3,4-tetrahydro-naphthalene. A spiro ring system is not a fused-polycyclic by this definition, but fused polycyclic ring systems of the invention may themselves have spiro rings attached thereto via a single ring atom of the fused-polycyclic.

"Halogen" or "halo" refers to fluorine, chlorine, bromine or iodine. "Haloalkyl" and "haloaryl" refer generically to alkyl and aryl groups that are substituted with one or more halogens, respectively. Thus, "dihaloaryl," "dihaloalkyl," "trihaloaryl," etc., refer to aryl and alkyl substituted with a plurality of halogens, but not necessarily a plurality of the same halogen; thus 4-chloro-3-fluorophenyl is within the scope of dihaloaryl. The phrase "mono- to per-halogenated" when combined with another group refers to groups wherein one hydrogen, more than one hydrogen, or all hydrogens are replaced with a halo. For example, a "mono- to per-halogenated methyl" would encompass groups such as —CH$_2$F, —CHCl$_2$ or —CF$_3$.

"Heterocycle" or "heterocyclyl" refers to a stable three- to fifteen-membered ring substituent that consists of carbon atoms and one to five heteroatoms selected from the group consisting of nitrogen, phosphorus, oxygen and sulfur. A heterocycle includes an aromatic heterocyclyl group. For purposes of this invention, the heterocyclyl substituent may be a monocyclic, bicyclic or tricyclic ring system, which may include fused or bridged ring systems as well as spirocyclic systems; and the nitrogen, phosphorus, carbon or sulfur atoms in the heterocyclyl group may be optionally oxidized to various oxidation states. In a specific example, the group —S(O)$_{0-2}$—, refers to —S— (sulfide), —S(O)— (sulfoxide), and —SO$_2$— (sulfone). For convenience, nitrogens, particularly but not exclusively, those defined as annular aromatic nitrogens, are meant to include their corresponding N-oxide form, although not explicitly defined as such in a particular example. Thus, for a compound of the invention having, for example, a pyridyl ring; the corresponding pyridyl-N-oxide is meant to be included as another compound of the invention. In addition, annular nitrogen atoms may be optionally quaternized; and the ring substituent may be partially or fully saturated or aromatic. Examples of heterocyclyl groups include, but are not limited to, azetidinyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, dioxaphospholanyl, and oxadiazolyl.

Preferred heterocylyls include, but are not limited to, acridinyl, azocinyl, benzimidazolyl, benzofuranyl, benzothiophenyl, benzoxazolyl, benzthiazolyl, benztriazolyl, pyridotriazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5, 2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2, 4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,3,4-triazolyl, and xanthenyl.

"Polycyclic heterocycle" as used herein refers to a heterocycle fused to at least one other aryl or heterocyclyl ring, as defined herein. Examples of bicyclic heterocycles include, but are not limited to, indolyl, benzimidazolyl, benzofuranyl, benzothiophenyl, benzoxazolyl, benzthiazolyl, benztriazolyl, pyridotriazolyl, benzisoxazolyl, benzisothiazolyl, and carbazolyl, When a group is referred to as "heterocyclylalkyl" such as "heterocyclyl-C$_1$-C$_8$ alkyl" a heterocycle moiety is attached to a parent structure via an alkylene group. Examples include pyrid-2-ylmethyl, morpholin-4-ylmethyl, piperidin-1-ylmethyl, and the like. Both the heterocycle and the corresponding alkylene portion of a "C$_1$-C$_6$ alkyl-heterocyclyl" group may be optionally substituted, as defined herein.

"Optional" or "optionally" means that the subsequently described event or circumstance may or may not occur, and that the description includes instances where said event or circumstance occurs and instances in which it does not. One of ordinary skill in the art would understand that with respect to any molecule described as containing one or more optional substituents, only sterically practical and/or synthetically feasible compounds are meant to be included. "Optionally substituted" refers to all subsequent modifiers in a term. So, for example, in the term "optionally substituted aryl-$C_{1-8}$ alkyl," both the "$C_{1-8}$ alkyl" portion and the "aryl" portion of the molecule may or may not be substituted. A list of exemplary optional substitutions is presented below in the definition of "substituted."

"Substituted" alkyl, aryl, and heterocyclyl refer respectively to alkyl, aryl, and heterocyclyl, one or more (for example up to about five, in another example, up to about three) hydrogen atoms are replaced by a substituent independently selected from: alkyl (for example, fluoromethyl), aryl (for example, 4-hydroxyphenyl), arylalkyl (for example, 1-phenyl-ethyl), heterocyclylalkyl (for example, 1-pyridin-3-yl-ethyl), heterocyclyl (for example, 5-chloro-pyridin-3-yl or 1-methyl-piperidin-4-yl), alkoxy, alkylenedioxy (for example methylenedioxy), amino (for example, alkylamino and dialkylamino), amidino, aryloxy (for example, phenoxy), arylalkyloxy (for example, benzyloxy), carboxy (—$CO_2H$), carboalkoxy (that is, acyloxy or —OC(=O)R), carboxyalkyl (that is, esters or —$CO_2R$), carboxamido, benzyloxycarbonylamino (CBZ-amino), cyano, acyl, halogen, hydroxy, nitro, sulfanyl, sulfinyl, sulfonyl, thiol, halogen, hydroxy, oxo, carbamyl, acylamino, and sulfonamido. And each substituent of a substituted group is optionally substituted, but these optional substituents themselves are not further substituted. Thus, an optionally substituted moiety is one that may or may not have one or more substituents, and each of the substituents may or may not have one or more substituents.

Some of the compounds of the invention may have imino, amino, oxo or hydroxy substituents off aromatic heterocyclyl systems. For purposes of this disclosure, it is understood that such imino, amino, oxo or hydroxy substituents may exist in their corresponding tautomeric form, i.e., amino, imino, hydroxy or oxo, respectively.

The compounds of the invention, or their pharmaceutically acceptable salts, may have asymmetric carbon atoms, oxidized sulfur atoms or quaternized nitrogen atoms in their structure.

The compounds of the invention and their pharmaceutically acceptable salts may exist as any and all possible stereoisomers, geometric isomers, enantiomers, diastereomers and anomers. All such single stereoisomers, racemates and mixtures thereof, and geometric isomers are intended to be within the scope of this invention.

Compounds of the invention are named according to systematic application of the nomenclature rules agreed upon by the International Union of Pure and Applied Chemistry (IUPAC), International Union of Biochemistry and Molecular Biology (IUBMB), and the Chemical Abstracts Service (CAS).

The description of the invention herein should be construed in congruity with the laws and principals of chemical bonding. It is assumed that when considering generic descriptions of compounds of the invention for the purpose of constructing a compound, such construction results in the creation of a stable structure. That is, one of ordinary skill in the art would recognize that theoretically some constructs which would not normally be considered as stable compounds (that is, sterically practical and/or synthetically feasible, supra).

When a particular group with its bonding structure is denoted as being bonded to two partners; that is, a divalent group, for example, —$OCH_2$—, then it is understood that either of the two partners may be bound to the particular group at one end, and the other partner is necessarily bound to the other end of the particular group, unless stated explicitly otherwise. Stated another way, divalent groups are not to be construed as limited to the depicted orientation, for example "—$OCH_2$—" is meant to mean not only "—$OCH_2$—" as drawn, but also "—$CH_2O$—."

Methods for the preparation and/or separation and isolation of single stereoisomers from racemic mixtures or non-racemic mixtures of stereoisomers are well known in the art. For example, optically active (R)- and (S)-isomers may be prepared using chiral synthons or chiral reagents, or resolved using conventional techniques. Enantiomers (R- and S-isomers) may be resolved by methods known to one of ordinary skill in the art, for example by: formation of diastereoisomeric salts or complexes which may be separated, for example, by crystallization; via formation of diastereoisomeric derivatives which may be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents or by converting on enantiomer to the other by asymmetric transformation. For a mixture of enantiomers, enriched in a particular enantiomer, the major component enantiomer may be further enriched (with concomitant loss in yield) by recrystallization.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

Furthermore, it is intended that the present invention cover compounds made either using standard organic synthetic techniques, including combinatorial chemistry or by biological methods, such as bacterial digestion, metabolism, enzymatic conversion, and the like.

"Cellular recognition ligand" or "targeting molecule" as used herein will be understood to refer to any antibody, antibody fragment, protein, peptide, polypeptide, RGD-peptide homing ligand, epidermal growth factor, vascular endothelial growth factor, 2-[3(1,3-dicarboxypropyl)-ureido]pentanedioic acid (DUPA) targeting prostate specific membrane antigen (PSMA), lectin, estrogen, polyunsaturated fatty acid (e.g., linoleic acid, linolenic acid, arachidonic acid, eicosapentaenoic acid), carbohydrate, non-peptide, vitamin, steroidal estrogen, biotin, riboflavin, nutrient-transport molecule (such as, but not limited to, transferrin), or any other cell binding molecule or substance thereof having the ability to bind to or reactively associate or complex with an antigen, receptor or other receptive moiety present on a surface of a particular cell so that the ligand can function to target the conjugate to the desired cell. The desired cell may be an infected cell, a bacterial or other type of pathogenic cell, a transformed cell, a tumor cell, a metastatic cell, a cell that produce autoimmune antibodies associated with an autoimmune disease, a cell that engages in modulating immune responses, and the like, wherein the antigen or receptor is uniquely expressed or overexpressed on the surface of the infected cell, bacterial cell, tumor cell, etc., and thus "marks" the cell as being an infected cell, bacterial cell, tumor cell, etc.

The targeting molecule may be a true ligand for the cell surface receptor and bind in a binding groove of the receptor. Also, the targeting molecule may be an antibody or fragment thereof raised against an epitope comprising a portion of the cell surface receptor, and capable of binding to the receptor when it is expressed on the surface of a cell of interest.

"Antibody" is used in the broadest sense and specifically includes intact monoclonal antibodies, polyclonal antibodies, multispecific antibodies (e.g., bispecific antibodies) formed from at least two intact antibodies and antibody fragments comprising preferably the antigen-binding or variable region (e.g., single chain antibodies, linear antibodies, Fv and Fab fragments, F(ab') fragments, F(ab')$_2$ fragments, diabodies). An antibody is a glycoprotein generated by the immune system and also refers to a full-length immunoglobulin molecule, or an immunologically active portion of a full-length immunoglobulin molecule that is capable of recognizing and binding to a specific antigen of a target of interest or part thereof. The immunoglobulin is of human, murine or rabbit origin and can be humanized or chimeric. A humanized antibody comes predominantly from a human but may contain nonhuman portions. A chimeric antibody contains a portion of the heavy and/or light chain that is identical with or homologous to corresponding sequence in antibody derived from a particular species or belonging to a particular antibody class or subclass, while the remainder of chain(s) is identical with or homologous to corresponding sequence in antibody derived from another species or belonging to another antibody class or subclass. Antibodies can raised against tumor associated antigens, infectious diseases or autoimmune disorders.

"Protein", "peptide" and "polypeptide", used interchangeably herein, refer to a polymeric form of amino acids of any length, which can include coded and non-coded amino acids, chemically or biochemically modified or derivatized amino acids, such as those with one or more deuteriums on the side chains or backbones, amino acids in L-form or D-form, or modified peptide backbones. The term includes polypeptide chains modified or derivatized in any manner, including, but not limited to, glycosylation, formylation, cyclization, acetylation, phosphorylation, and the like. The term includes naturally-occurring peptides, synthetic peptides, peptides comprising one or more amino acid analogs and peptides with reversed or retro-inversed peptide bonds. The term includes fusion proteins, including, but not limited to, fusion proteins with a heterologous amino acid sequence, fusions with heterologous and homologous leader sequences, with or without N-terminal methionine residues; immunologically tagged proteins; and the like.

"Patient" for the purposes of the present invention includes humans and other animals, particularly mammals, and other organisms. Thus, the methods are applicable to both human therapy and veterinary applications. In a preferred embodiment the patient is a mammal, and in a most preferred embodiment the patient is human.

"Effective amount" or "therapeutically effective amount" is an amount of a conjugate compound of the invention, to provide, when administered to a patient, treatment for the disease state or disorder being treated or to otherwise provide the desired effect (e.g., induction of an effective immune response, amelioration of a symptom of the disease). The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to their knowledge and to this disclosure. Generally, the dosage of a compound administered to a patient is about 0.01 mg/kg to about 100 mg/kg of the patient's body weight once daily. Typically, the dosage administered to a patient is about 0.1 mg/kg to about 10 mg/kg of the patient's body once weekly. Preferably, the dosage administered to a patient intravenously is about 0.1 mg/kg to about 5 mg/kg of the patient's body every 3 weeks.

"Disorder" as used herein refers to any condition that would benefit from treatment with the conjugate compound of the present invention. This includes chronic and acute disorders or diseases including those pathological conditions that predispose the mammal to the disorder in question.

"Cancer" refers to unregulated and uncontrolled cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinorna, glucagonoma, gastrinoma, carcinoid tumors, vipoma), small bowel (adenocarcinora, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis defomians), meninges (meningioma, meningiosarcoma, gliomatosis), brain (astrocytoma, medulloblastoma, glioma, ependymoma, germinoma [pinealoma], glioblastorna multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles, dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

"Autoimmune disease" herein is a disease or disorder arising from and directed against an individual's own tissues or a co-segregate or manifestation thereof or resulting condition therefrom. Examples of autoimmune diseases or disorders include, but are not limited to, arthritis (rheumatoid arthritis, juvenile rheumatoid arthritis, osteoarthritis, psoriatic arthritis, and ankylosing spondylitis), psoriasis, dermatitis including atopic dermatitis; chronic idiopathic urticaria, polymyositis/dermatomyositis, toxic epidermal necrolysis, systemic scleroderma and sclerosis, responses associated with inflammatory bowel disease (IBD) (Crohn's disease, ulcerative colitis), respiratory distress syndrome, including adult respiratory distress syndrome (ARDS), meningitis, IgE-mediated diseases such as anaphylaxis and allergic rhinitis, encephalitis such as Rasmussen's encephalitis, uveitis, colitis such as microscopic colitis and collagenous colitis, glomerulonephritis (GN) such as membranous GN, idiopathic membranous GN, membranous proliferative GN (MPGN), including Type I and Type II, and rapidly progressive GN, allergic conditions, eczema, asthma, conditions involving infiltration of T cells and chronic inflammatory responses, atherosclerosis, autoimmune myocarditis, leukocyte adhesion deficiency, systemic lupus erythematosus (SLE) such as cutaneous SLE, lupus (including nephritis, cerebritis, pediatric, non-renal, discoid, alopecia), juvenile onset diabetes, multiple sclerosis (MS) such as spino-optical MS, allergic encephalomyelitis, immune responses associated with acute and delayed hypersensitivity mediated by cytokines and T-lymphocytes, tuberculosis, sarcoidosis, granulomatosis including Wegener's granulomatosis, agranulocytosis, vasculitis (including Large Vessel vasculitis (including Polymyalgia Rheumatica and Giant Cell (Takayasu's Arteritis), Medium Vessel vasculitis (including Kawasaki's Disease and Polyarteritis Nodosa), CNS vasculitis, and ANCA-associated vasculitis, such as Churg-Strauss vasculitis or syndrome (CSS), aplastic anemia, Coombs positive anemia, Diamond Blackfan anemia, immune hemolytic anemia including autoimmune hemolytic anemia (AIHA), pernicious anemia, pure red cell aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome, myasthenia gravis, antigen-antibody complex mediated diseases, anti-glomerular basement membrane disease, anti-phospholipid antibody syndrome, allergic neuritis, Bechet disease, Castleman's syndrome, Goodpasture's Syndrome, Lambert-Eaton Myasthenic Syndrome, Reynaud's syndrome, Sjorgen's syndrome, Stevens-Johnson syndrome, solid organ transplant rejection (including pretreatment for high panel reactive antibody titers, IgA deposit in tissues, and rejection arising from renal transplantation, liver transplantation, intestinal transplantation, cardiac transplantation, etc.), graft versus host disease (GVHD), pemphigoid bullous, pemphigus (including vulgaris, foliaceus, and pemphigus mucus-membrane pemphigoid), autoimmune polyendocrinopathies, Reiter's disease, stiff-man syndrome, immune complex nephritis, IgM polyneuropathies or IgM mediated neuropathy, idiopathic thrombocytopenic purpura (ITP), thrombotic throbocytopenic purpura (TTP), thrombocytopenia (as developed by myocardial infarction patients, for example), including autoimmune thrombocytopenia, autoimmune disease of the testis and ovary including autoimmune orchitis and oophoritis, primary hypothyroidism; autoimmune endocrine diseases including autoimmune thyroiditis, chronic thyroiditis (Hashimoto's Thyroiditis), subacute thyroiditis, idiopathic hypothyroidism, Addison's disease, Grave's disease, autoimmune polyglandular syndromes (or polyglandular endocrinopathy syndromes), Type I diabetes also referred to as insulin-dependent diabetes mellitus (IDDM), including pediatric IDDM, and Sheehan's syndrome; autoimmune hepatitis, Lymphoid interstitial pneumonitis (HIV), bronchiolitis obliterans (non-transplant) vs NSIP, Guillain-Barre Syndrome, Berger's Disease (IgA nephropathy), primary biliary cirrhosis, celiac sprue (gluten enteropathy), refractory sprue with co-segregate dermatitis herpetiformis, cryoglobulinemia, amylotrophic lateral sclerosis (ALS; Lou Gehrig's disease), coronary artery disease, autoimmune inner ear disease (AIED), autoimmune hearing loss, opsoclonus myoclonus syndrome (OMS), polychondritis such as refractory polychondritis, pulmonary alveolar proteinosis, amyloidosis, giant cell hepatitis, scleritis, monoclonal gammopathy of uncertain/unknown significance (MGUS), peripheral neuropathy, paraneoplastic syndrome, channelopathies such as epilepsy, migraine, arrhythmia, muscular disorders, deafness, blindness, periodic paralysis, and channelopathies of the CNS; autism, inflammatory myopathy, and focal segmental glomerulosclerosis (FSGS).

"Pharmaceutical agent" or "drug" as used herein refers to a chemical compound or composition capable of inducing a desired therapeutic effect when properly administered to a patient. In one aspect, the pharmaceutical agent is the anti-cancer drug including, but not limited to: Cytotoxic agents: gemcitabine, velcade, revamid, thalamid, lovastatin, 1-methyl-4-phenylpyridinium ion, staurosporine, actinomycin D, dactinomycin, bleomycin A2, bleomycin B2, peplomycin, daunorubicin, doxorubicin (adriamycin), idarubicin, epirubicin, pirarubicin, zorubicin, mtoxantrone, verapamil, thapsigargin. Alkylating agents: cyclophosphamide, ifosfamide, trofosfamide, chlorambucil, melphalan, carmustine (BCNU), lomustine (CCNU), busulfan, treosulfan, decarbazine, cisplatin, carboplatin Plant Alkaloids: vincristine, vinblastine, vindesine, vinorelbine, paclitaxel, docetaxol. DNA Topoisomerase Inhibitors: etoposide, teniposide, topotecan, 9-aminocamptothecin, camptothecin, crisnatol, mitomycin C. Anti-metabolites: methotrexate, trimetrexate, mycophenolic acid, tiazofurin, ribavirin, hydroxyurea, deferoxamine, 5-Fluorouracil, floxuridine, doxifluridine, ratitrexed, cytarabine (ara C), cytosine arabinoside, fludarabine, mercaptopurine, thioguanine.

In one aspect, the term as used herein refers to a substance that inhibits, prevents or diagnoses the function of cells and/or causes destruction of cells and is intended to include a radionuclide (e.g., $^{211}$At, $^{225}$Ac, $^{213}$Bi, $^{60}$Co, $^{125}$I, $^{131}$I, $^{111}$In, $^{177}$Lu, $^{32}$P, $^{223}$Ra, $^{186}$Re, $^{188}$Re, $^{153}$Sm, $^{227}$Th and $^{90}$Y), a pharmaceutical agent, and a toxin such as small molecule toxin or enzymatically active toxin of bacterial, fungal, plant or animal origin (e.g., calicheamicin, maytansinoids, auristatins, dolastatins, pyrrolobenzodiazapines, CC-1065 and duocarmycins), including synthetic analogs and derivatives thereof.

Also included in this term are anti-hormonal agents that act to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, onapristone, Vitamin D3 analogs (EB 1089, CB 1093, KH 1060), vertoporfin (BPD-MA), phthalocyanine, photosensitizer Pc4, demethoxy-hypocrellin A (2BA-2-DMHA); aromatase inhibitors that inhibit the enzyme aromatase, which regulates estrogen production in the adrenal glands, such as, for example, 4(5)-imidazoles, aminoglutethimide, megestrol acetate, exemestane, formestanie, fadrozole, vorozole, letrozole, and anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-α, Raf, H-Ras, and epidermal growth factor receptor (EGF-R); vaccines such as gene therapy vaccines, for example, allovectin vaccine, leuvectin vaccine, and VAXID vaccine.

Further included in this term are EGFR-targeted drugs that bind to EGFR and, optionally, inhibits EGFR activation, as well as kinase inhibitors and anti-angiogenic agents. Examples of such pharmaceutical agents include antibodies and small molecules (e.g., Axitinib, Crizotinib, Dasatinib, Erlotinib, Gefitinib, Imatinib, Lapatinib, Nilotinib, Pazopanib, Pegaptanib, Ruxolitinib, Sorafenib, Sunitinib, Vemurafenib).

In yet another aspect, pharmaceutical agent is immunomodulating molecules such as cytokines and oligodeoxynucleotides containing unmethylated CpG motifs (CpG-ODN). Examples of such pharmaceutical agents include, but are not limited to, interferons (e.g., Interferon-α, Interferon-β and Interferon-γ), interleukins (ILs), colony stimulating factors (CSFs) [e.g., granulocyte-CSF (G-CSF), macrophage-CSF (M-CSF), granulocyte-macrophage-CSF (GM-CSF)], tumor necrosis factors (TNF-α, TNF-β), insulin-like growth factor-I and -II, CpG ODN 1826, CpG ODN 2006, CpG ODN 2216, CpG ODN 2395.

"Treating" or "treatment" as used herein covers the treatment of a disease-state in a human, which disease-state is characterized by abnormal cellular proliferation, disorder and infection and includes at least one of: (i) preventing the disease-state from occurring in a human, in particular, when such human is predisposed to the disease-state but has not yet been diagnosed as having it; (ii) inhibiting the disease-state, i.e., arresting its development; and (iii) relieving the disease-state, i.e., causing regression of the disease-state. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

"Pharmaceutically acceptable salt" include acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.)

In another aspect, the invention provides pharmaceutical compositions comprising compounds according to the first aspect of the invention and a pharmaceutically acceptable carrier, excipient, or diluent. In certain other preferred embodiments, administration may preferably be by the oral route. Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracistemally, rectally, or via urethral, ocular intratumoral, intraventricular, intrathecal, pulmonary and irrigation method, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages.

The compositions will include a conventional pharmaceutical carrier or excipient and a compound of the invention as the/an active agent, and, in addition, may include other medicinal agents, pharmaceutical agents, carriers, adjuvants, etc. Compositions of the invention may be used in combination with anticancer or other agents that are generally administered to a patient being treated for cancer or other disorder. Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylalted hydroxytoluene, etc. The dosage form can be designed as a sustained release or timed release.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), dextrose, mannitol, polyvinylpyrrolidone, gelatin, hydroxycellulose, acacia, suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants. The liquid formulation can be buffered, isotonic solution.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Generally, depending on the intended mode of administration, the pharmaceutically acceptable compositions will contain about 0.01% to about 99.99% by weight of a conjugate(s) of the invention, or a pharmaceutically acceptable salt thereof, and 99.99% to 0.01% by weight of a suitable pharmaceutical excipient. In one example, the composition will be between about 0.5% and about 75% by weight of a conjugate(s) of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state in accordance with the teachings of this invention.

The compounds of the invention, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

In one aspect, the present invention provides linker (LK) compounds that would readily allow conjugation of cellular recognition ligands, such as antibodies, antibody fragments, proteins, peptides, polypeptides, growth factors, lectins, steroidal estrogens, vitamins and nutrient-transport molecules, with drug payload molecules including but not limited to cytotoxic agents, target chemotherapeutic agents, radionuclides, immunomodulating agents. Thus, the linker compounds have the characteristics of reacting with a ligand molecule at one end and with a drug molecule at the other end. The ligand is conjugated with the linker via a reactive sulfhydryl or thiol group (—SH) in the ligand molecule to form a thioether bond. The linker serves as a thiol acceptor. The drug is conjugated to the linker via a functional group selected from primary or secondary amine, hydroxyl, sulfhydryl, carboxyl, aldehyde or ketone via esterification, amidation, reductive amination or aldol reaction.

In one aspect, the thiol acceptor in the linker compound has a double bond, represented by the general formula:

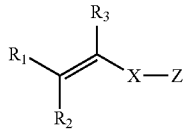

(I)

wherein $R_1$, $R_2$ and $R_3$ are independently selected from H, deuterium, halogen, CN, $NO_2$, HC(O), $CO_2H$, $C(O)NH_2$, $S(O)_2OH$, $S(O)_2NH_2$, a straight or branched $C_{1-8}$ alkyl, aryl-$C_{1-8}$ alkyl, heterocycle-$C_{1-8}$ alkyl, cyclo($C_{3-9}$)alkyl, aryl, heterocycle, $R_4C(O)$, $R_4O$, $R_4S$, $R_4S(O)$, $R_4S(O)_2$, $R_4NH$, $R_4R_5N$, $C(Y)OR_4$, $C(Y)SR_4$, $C(Y)NHR_4$, $C(Y)NR_4R_5$, $R_4OC(Y)$, $R_4SC(Y)$, $R_4NHC(Y)$, $R_4R_5NC(Y)$, $R_4OS(O)_2$, $H-Y-(CH_2CH_2O)_m$, $R_4-Y-(CH_2CH_2O)_m$, $R_4C(Y)-O-(CH_2CH_2O)_m$, $R_4C(Y)-S-(CH_2CH_2O)_m$, $R_4C(Y)-NH-(CH_2CH_2O)_m$, $R_4C(Y)-N(R_5)-(CH_2CH_2O)_m$, or $-X-Z$, wherein the aryl comprises phenyl or a polycyclic aryl group such as naphthyl;

the heterocyle comprises a 5 or 6 membered aromatic heterocycle such as pyridyl, diazinyl, pyrimidinyl, 5-methoxy pyrimidinyl, (1,2,4) triazine-3,5-dione-6-yl, 6-mercaptopyrimidine-4-yl, pyrrolyl, pyrazolyl, imidazolyl, oxazolyl, isoxazolyl, thiazolyl, isothiazolyl, furanyl, or thienyl;

a 3 to 9 membered non-aromatic heterocycle comprising piperazinyl, 4-methyl piperazinyl, pyrrolidinyl, imidazolidinyl, imidazolinyl, thiazolidinyl, thiazolinyl, isothiazolidinyl, isothiazolinyl, pyranyl, or morpholinyl; or a polycyclic heterocycle such as indolyl, benzthienyl, benzofuranyl, isoindolyl, isobenzothienyl, or isobenzofuranyl;

wherein each alkyl, cycloalkyl, aryl, and heterocycle are each optionally substituted with one or more groups (e.g., 1, 2, or 3 group) which are each independently halogen, CN, $N_3$, $NO_2$, OH, SH, $NH_2$, HONH, HON=, $CO_2H$, $C(O)NH_2$, $S(O)_2OH$, $S(O)_2NH_2$, $C_{1-8}$ alkyl, $R_4O$, $R_4S$, $R_4S(O)$, $R_4S(O)_2$, $R_4NH$, $R_4R_5N$, $R_4ONH$, $R_4ON=$, $R_4C(O)$, $R_4C(Y)O$, $R_4C(Y)S$, $R_4C(Y)NH$, $R_4C(Y)N(R_5)$, $C(Y)OR_4$, $C(Y)SR_4$, $C(Y)NHR_4$, $C(Y)NR_4R_5$, $R_4OC(Y)O$, $R_4OC(Y)S$, $R_4OC(Y)NH$, $R_4OC(Y)NR_5$, $R_4SC(Y)O$, $R_4SC(Y)S$, $R_4SC(Y)NH$, $R_4SC(Y)NR_5$, $R_4NHC(Y)O$, $R_4NHC(Y)S$, $R_4NHC(Y)NH$, $R_4NHC(Y)NR_5$, $R_4R_5NC(Y)O$, $R_4R_5NC(Y)S$, $R_4R_5NC(Y)NH$, $R_4R_5NC(Y)NR_4$, $S(O)_2OR_4$, $S(O)_2SR_4$, $S(O)_2NHR_4$, $S(O)_2NR_4R_5$, $H-Y-(CH_2CH_2O)_m$, $R_4-Y-(CH_2CH_2O)_m$, $R_4C(Y)-O-(CH_2CH_2O)_m$, $R_4C(Y)-S-(CH_2CH_2O)_m$, $R_4C(Y)-NH-(CH_2CH_2O)_m$, $R_4C(Y)-N(R_5)-(CH_2CH_2O)_m$, $X-(CH_2CH_2O)_m$, $-X-Z$, or $R_1$ and $R_2$, $R_1$ and $R_3$ taken together with the carbon atoms to which they are attached form a cyclo($C_{3-9}$)alkyl, aryl, or heterocycle, wherein each alkyl, cycloalkyl, aryl, and heterocycle are each optionally substituted with one or more groups as previously defined;

$R_4$ and $R_5$ above are independently selected from a straight or branched $C_{1-8}$ alkyl, aryl-$C_{1-8}$ alkyl, heterocycle-$C_{1-8}$ alkyl, cyclo($C_{3-9}$)alkyl, aryl, heterocycle, or $R_4$ and $R_5$ taken together with the nitrogen atom to which they are attached form a cyclo($C_{3-9}$)alkyl, aryl, or heterocycle, wherein each alkyl, cycloalkyl, aryl, and heterocycle are each optionally substituted with one or more groups as previously defined;

each Y is independently selected from O, S, NH, $NR_4$, wherein $R_4$ is defined as above;

each Z is selected from OH, SH, NCS, NCO, $NHR_6$, $CONR_4R_5$, $CONHR_6$, $CO_2R_6$, $C(O)SR_6$, $C(O)R_6$, where $R_4$ and $R_5$ are defined as above; $R_6$ is H, $C_{1-8}$ alkyl, cyclo($C_{3-9}$) alkyl, aryl, or heterocycle, wherein each alkyl, cycloalkyl, aryl, and heterocycle are each optionally substituted with one or more groups as previously defined;

each m is an integer independently selected from 1 to 20;

each X is a spacer wherein the spacer must be stable in plasma but may be cleavable to release the fully active drug when internalized by the target cell or on the target cell surface, depending on the release mechanism. In one embodiment, in the case of the conjugates with radioisotopes, there is no needs to release the radioactive isotopes and the non-cleavable spacer is preferred. X can be selected independently from $[C(O)]_n-W_o-[C(O)]_p-\{Y_1-[C(O)]_q-W_r\}_s-[C(O)]_q-(AA)_t-$, $[C(O)]_n-W_o-[C(O)]_p-[Y_1-(CH_2CH_2O)_m]_u-W_r-[C(O)]_q-(AA)_t-$, $[C(O)]_n-W_o-[C(O)]_p-[Y_1-(CH_2CH_2O)_m]_u-[C(O)]_q-W_r-(AA)_t-$, $[C(O)]_n-W_o-[C(O)]_p-[Y_1-(CH_2CH_2O)_m]_u-C(O)-Y_1-W_r-(AA)_t-$, $[C(O)]_n-W_o-[C(O)]_p-[Y_1-(CH_2CH_2O)_m]_u-W_r-C(O)-Y_1-W_r-(AA)_t-$, $[C(O)]_n-W_o-[C(O)]_p-[Y_1-(CH_2CH_2O)_m]_u-W_r-Y_1-[C(O)]_q-W_r-(AA)_t-$, $[C(O)]_n-W_o-[C(O)]_p-[Y_1-(CH_2CH_2O)_m]_u-W_r-Y_1-C(O)-Y_1-W_r-(AA)_t-$, $[C(O)]_n-W_o-[C(O)]_p-[Y_1-(CH_2CH_2O)_m]_u-(AA)_t-[Y_1-(CH_2CH_2O)_m]_u-W_r-$, $[C(O)]_n-W_o-[C(O)]_p-\{Y_1-[C(O)]_q-W_r\}_s-(AA)-\{Y_1-[C(O)]_q-W_r\}_s-[Y_1-(CH_2CH_2O)_m]_u-[C(O)]_q-W_r-(AA)_t-$, $[C(O)]_n-W_o-[C(O)]_p-\{Y_1-[C(O)]_q-W_r\}_s-(AA)-C(O)-\{Y_1-[C(O)]_q-W_r\}_s-[Y_1-(CH_2CH_2O)_m]_u-[C(O)]_q-W_r-(AA)_t-$, $[C(O)]_n-W_o-[C(O)]_p-\{Y_1-[C(O)]_q-W_r\}_s-(AA)-\{Y_1-[C(O)]_q-W_r\}_s-C(O)-[Y_1-(CH_2CH_2O)_m]_u-[C(O)]_q-W_r-(AA)_t-$, wherein each W is selected from a straight or branched $C_{1-8}$ alkyl, aryl-$C_{1-8}$ alkyl, heterocycle-$C_{1-8}$ alkyl, cyclo($C_{3-9}$)alkyl, aryl, or heterocycle, wherein each alkyl, cycloalkyl, aryl, and heterocycle are each optionally substituted with one or more groups as previously defined; preferably, W is $(CH_2)_m$, $(CF_2)_m$, phenyl or bis-phenyl, wherein m is defined as above;

each m is defined as above;

each n, o, p, q, r and t is an integer independently selected from 0 and 1; when o is 0, n and p cannot be both 1;

each s is an integer independently selected from 0 to 8;

each u is an integer independently selected from 1 to 8;

each $Y_1$ is selected from O, S, NH, $NR_4$, $N-[C(O)]_q-W_r-X-Z$, wherein $R_4$, W, X, Z, r and q are defined as above;

each AA is an amino acid residue sequence independently selected from the group consisting of alanine, glycine, isoleucine, leucine, methionine, phenylalanine, proline, tryptophan, valine, lysine, lysine protected with acetyl or formyl, arginine, arginine protected with tosyl or nitro groups, histidine, ornithine, ornithine protected with acetyl or formyl, citrulline, and combinations thereof. These amino acid residues (AA) can be in L- or D-form. The amino acid residue sequence, connected either via natural peptide bonds, i.e., CO—NH with the termini shown as $NH_2$-AA-$CO_2H$, or via reversed peptide bonds, i.e., NH—CO with the termini shown as HO₂C-AA-NH₂, is specifically tailored so that it will be selectively cleaved by one or more of enzymes (e.g., cathepsin B) inside the cell or on the cell surface. The amino acid residue chain length preferably ranges from that of a dipeptide to that of a tetrapeptide. The preferred aminoacid sequences include Phe-Lys, Val-Lys, Val-Cit and D-Phe-L-Phe-Lys.

The following are exemplary linker compounds (Formula I) as the thiol acceptor to illustrate further the present invention:

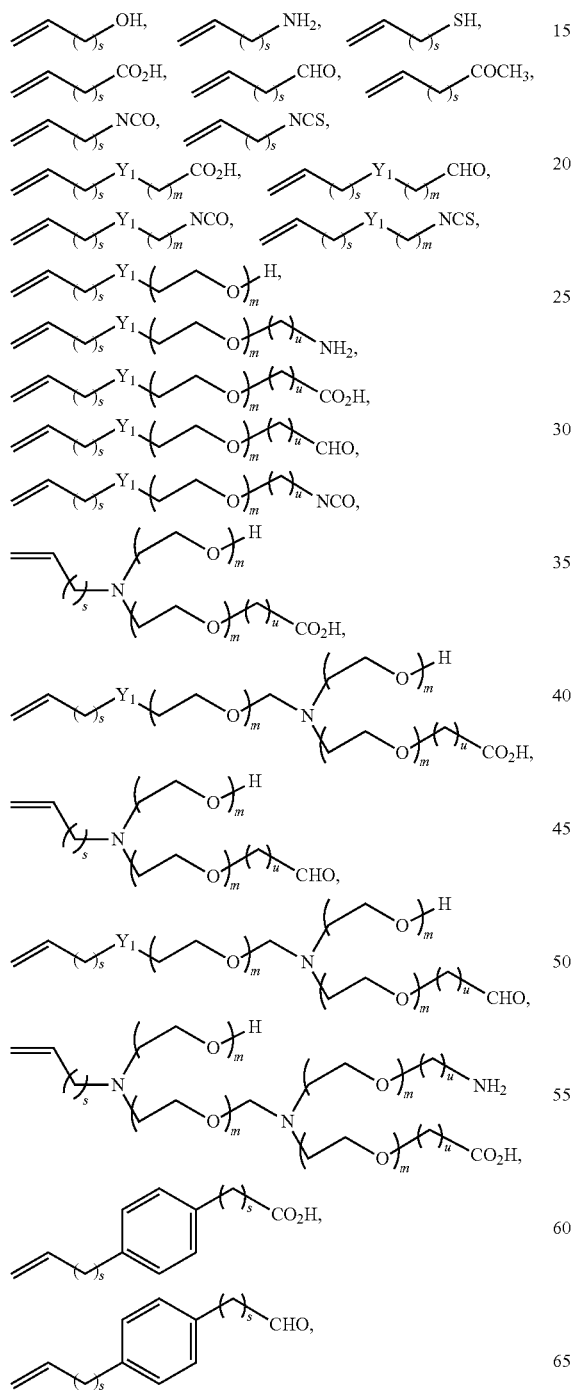

-continued

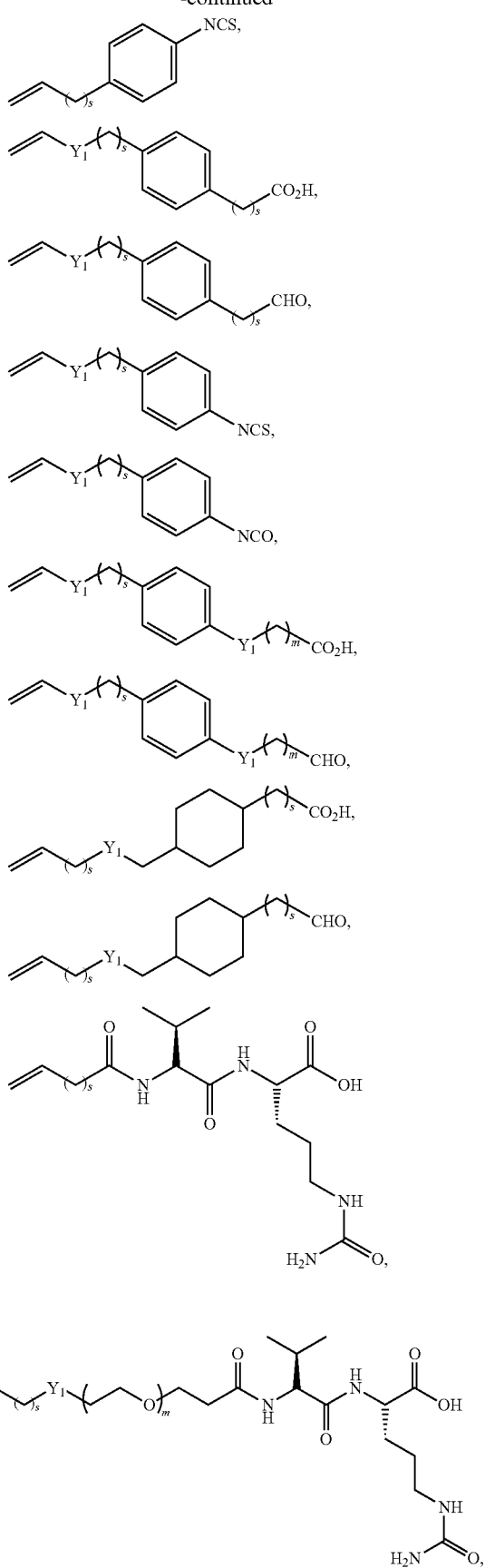

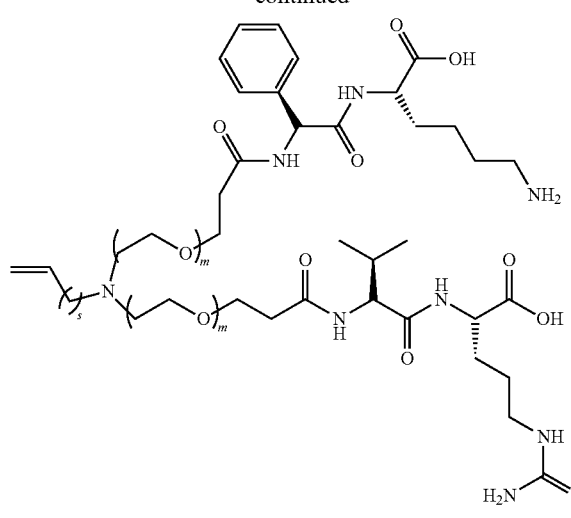

In another aspect, the thiol acceptor in the linker compound has a double bond, represented by the general formula:

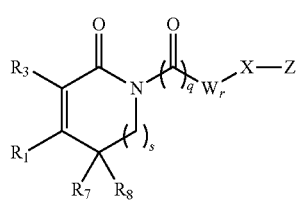
(II)

wherein $R_1$, $R_3$, W, X, Z, q, r and s are defined as above;

$R_7$, $R_8$ are independently selected from H, deuterium, F and $R_7$ and $R_8$ can be together to form =O and =S;

with a proviso that, when $R_1=R_3=$H and s=0, $R_7$ and $R_8$ together cannot be =O.

The following are exemplary linker compounds (Formula II) as the thiol acceptor to illustrate further the present invention:

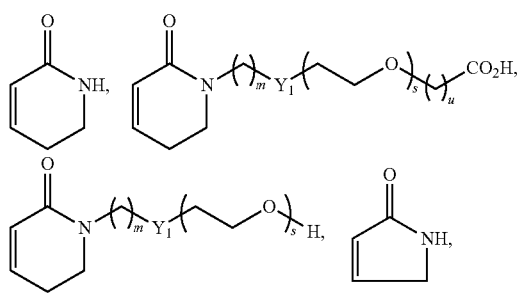

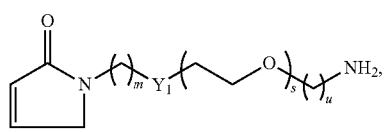

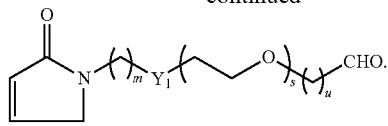

In still another aspect, the thiol acceptor in the linker compound has a double bond, represented by the general formula:

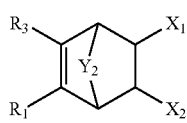
(III)

wherein $R_1$ and $R_3$ are defined as above;

$X_1$ and $X_2$ are independently selected from H, deuterium, —X—Z, wherein X and Z are defined as above, or $X_1$ and $X_2$ taken together can form a cyclic ring;

$Y_2$ is $CH_2$ or $Y_1$, wherein $Y_1$ is defined as above;

The following are exemplary linker compounds (Formula III) as the thiol acceptor to illustrate further the present invention:

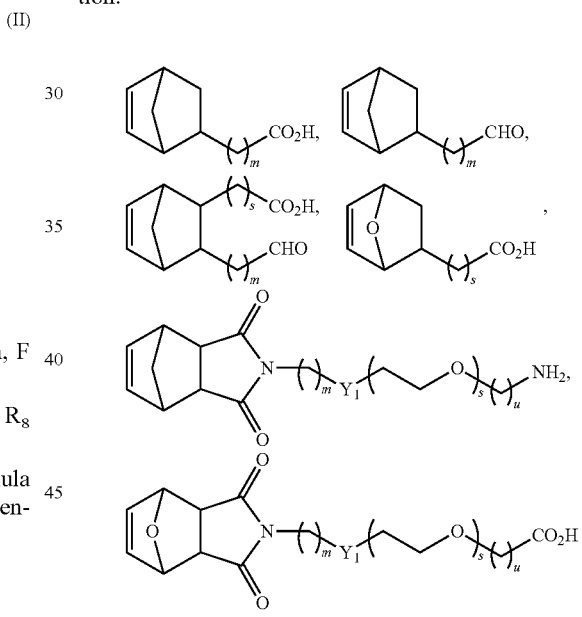

The thiol acceptors (Formula I, II and III) either are commercially available or can be synthesized by conventional methods.

In another aspect, the present invention provides Linker-Drug conjugates or a pharmaceutically acceptable salt or solvate thereof, represented by the general formula:

$$LK-D_v \quad (IV)$$

wherein

LK is a linker moiety selected from Formula I, II or III;

v is an integer selected from 1 to 10;

each D is a drug moiety carrying a chemically reactive functional group which is either natively present or is chemically introduced to provide the site for the conjugation with the LK. The said functional groups can be independently selected from a primary or secondary amine, hydroxyl, sulfhydryl, carboxyl, aldehyde or a ketone. The drug moiety can be independently selected from the group including but not limiting to cytotoxic drugs, target chemotherapeutic agents and immunomodulating agents.

The Linker-Drug conjugate is formed via a covalent bond between the functional group Z in the thiol acceptor, e.g., OH, SH, $NHR_6$, $CONR_4R_5$, $CONHR_6$, $CO_2R_6$, $C(O)SR_6$, $C(O)R_6$, and a functional group in the drug moiety selected from primary or secondary amine, hydroxyl, sulfhydryl, carboxyl, aldehyde or ketone. The conjugation reaction to form the said covalent bond is performed under conventional chemical synthesis conditions, well known to the skilled in the art, such as esterification, amidation, reductive amination or aldol reaction. The said covalent bond must be stable in general circulation, may or may not be enzymatically cleaved within the cell or on the cell surface but preferably be labile to release the fully active drug when internalized by the target cell or on the target cell surface.

In yet another aspect, an additional tethering group or self-immolative (SI) moiety is inserted between a linker and a drug that, upon a single activation event when internalized by the target cell or on the target cell surface, leads to a spontaneous and rapid release of the fully active drug, resulting in conjugates or a pharmaceutically acceptable salt or solvate thereof, represented by the general formula:

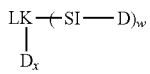
(V)

wherein

LK is a linker moiety selected from Formula I, II or III;

each SI is preferably selected from the following group, or combination thereof: C(O), C(S), C(NH),

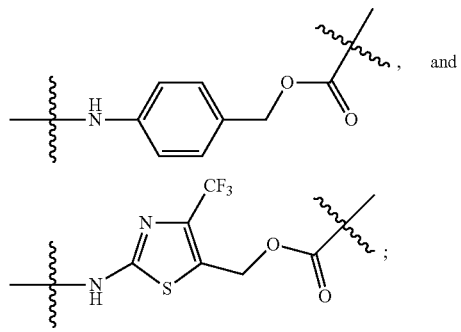

each D is as previously defined;

w is an integer selected from 1 to 10;

x is an integer selected from 0 to 9; preferably, the sum of w and x should not exceed 10.

In further another aspect, a metal chelating (CL) moiety is inserted between a linker and a radionuclide that is able to chelate and hold the radioisotope and prevent it from premature release and off-target cell destruction, resulting in conjugates or a pharmaceutically acceptable salt or solvate thereof, represented by the general formula:

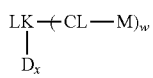
(VI)

wherein

The LK and CL is connected via a covalent bond which is chemically and enzymatically stable in the general circulation and on the target cell surface after administration;

LK is a linker moiety selected from Formula I, II or III;

each M is a radioisotope preferably selected from $^{211}At$, $^{225}Ac$, $^{213}Bi$, $^{60}Co$, $^{125}I$, $^{131}I$, $^{111}In$, $^{177}Lu$, $^{32}P$, $^{223}Ra$, $^{186}Re$, $^{188}Re$, $^{153}Sm$, $^{227}Th$ and $^{90}Y$;

each CL is a metal chelating moiety preferably selected from the following group or combination thereof:

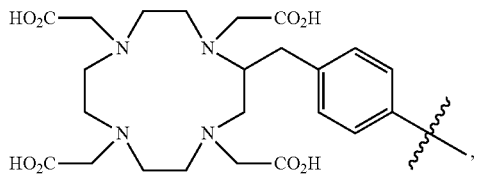

p-Benzyl DOTA

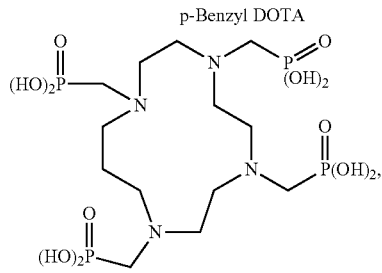

DOTMP

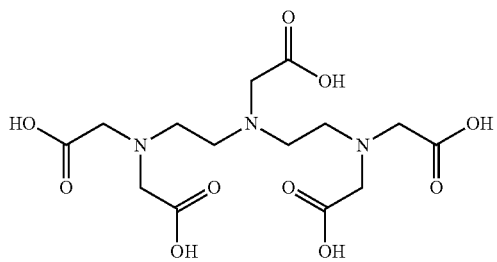

DTAP

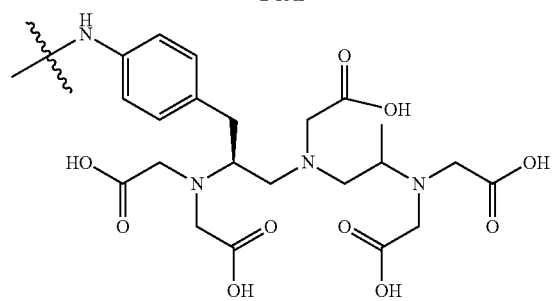

each D, w and x are as previously defined; preferably, the sum of w and x should not exceed 10.

The following are exemplary drug molecules with a chemically reactive functional group to illustrate further the present invention:

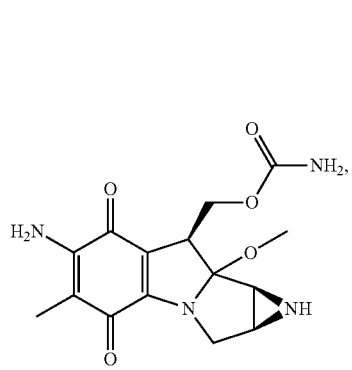
Mitomycin C
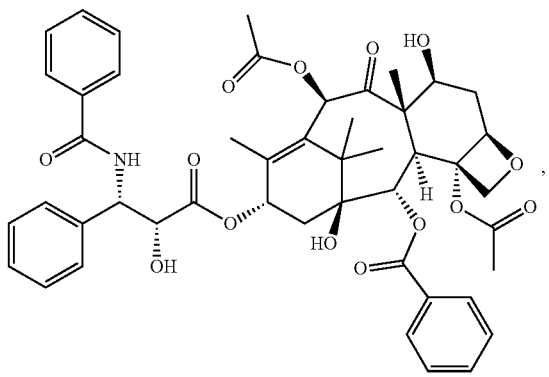
Paclitaxel
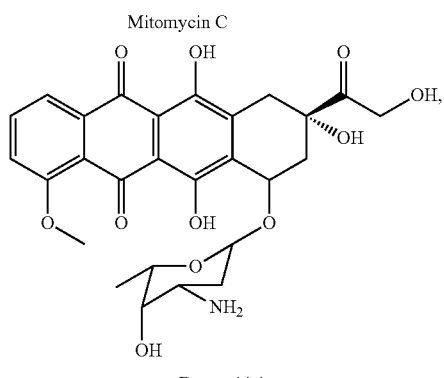
Doxorubicin
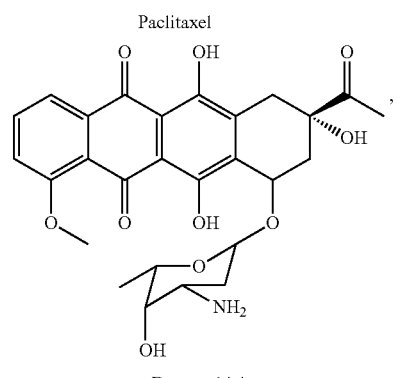
Daunorubicin
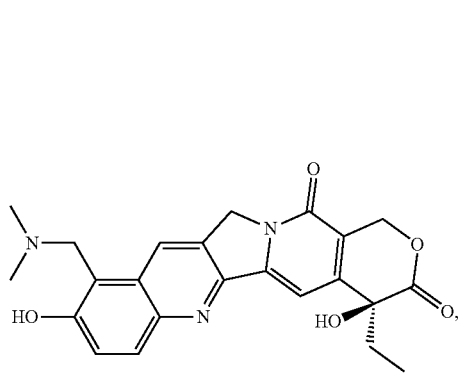
Totptecan
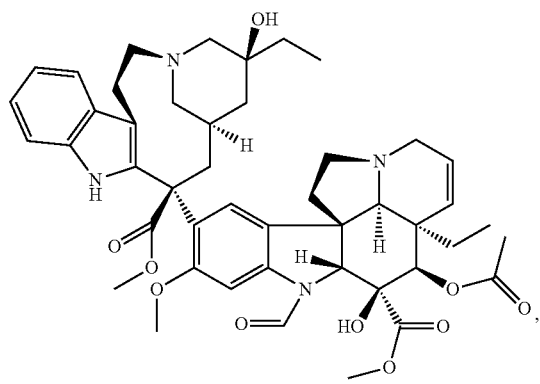
Vincristine
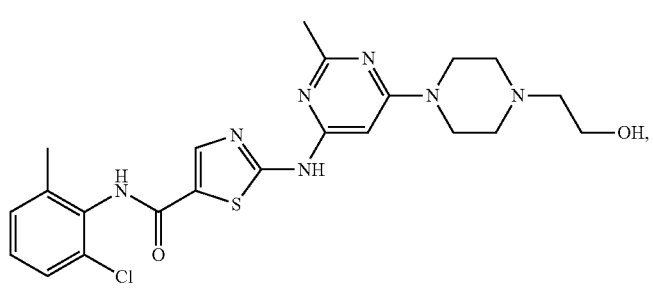
Dasatinib
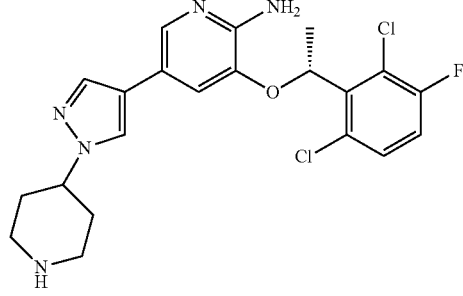
Crizotinib

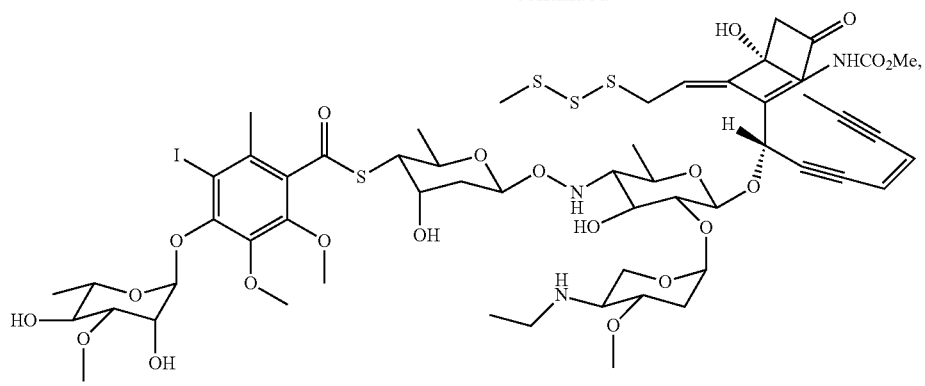
Calicheamicin
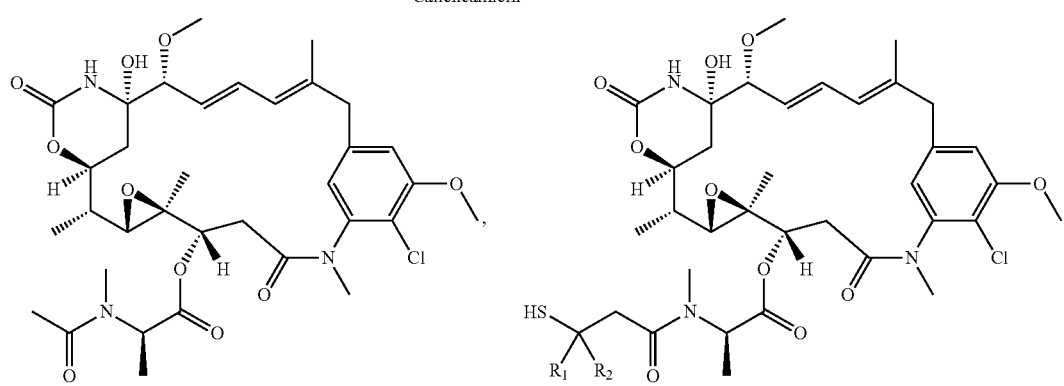
Maytansine
DM1: R1 = R2 = H
DM3: R1 = H, R2 = Me
DM4: R1 = R2 = Me
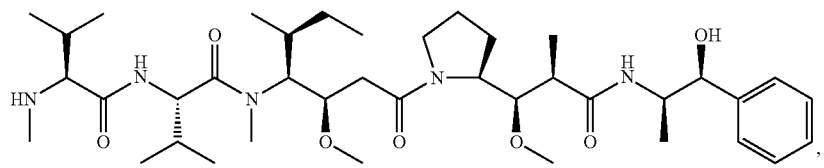
Monomethyl auristatin E (MMAE)
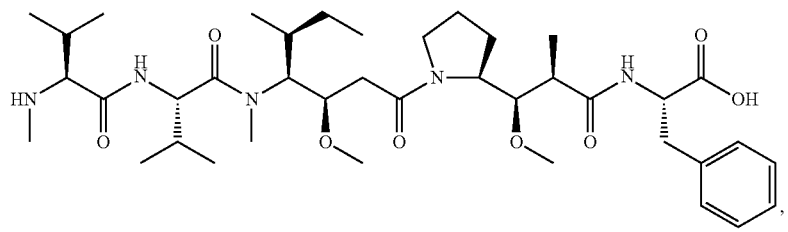
Monomethyl auristatin F (MMAF)
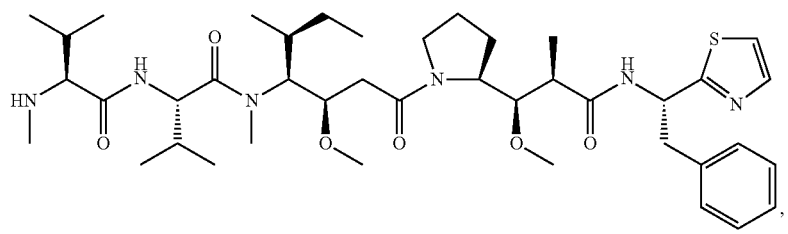
Monomethyl dolastatin 10

-continued
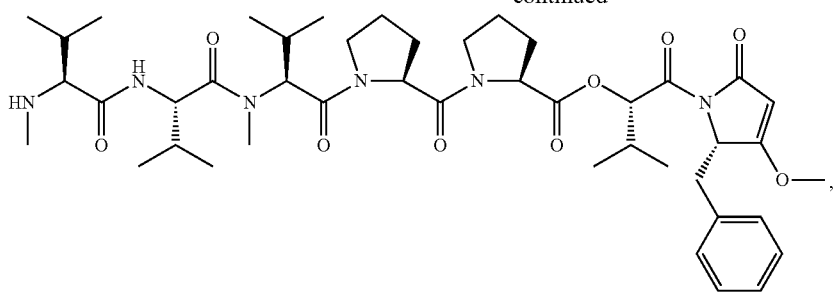
Monomethyl dolastatin 15
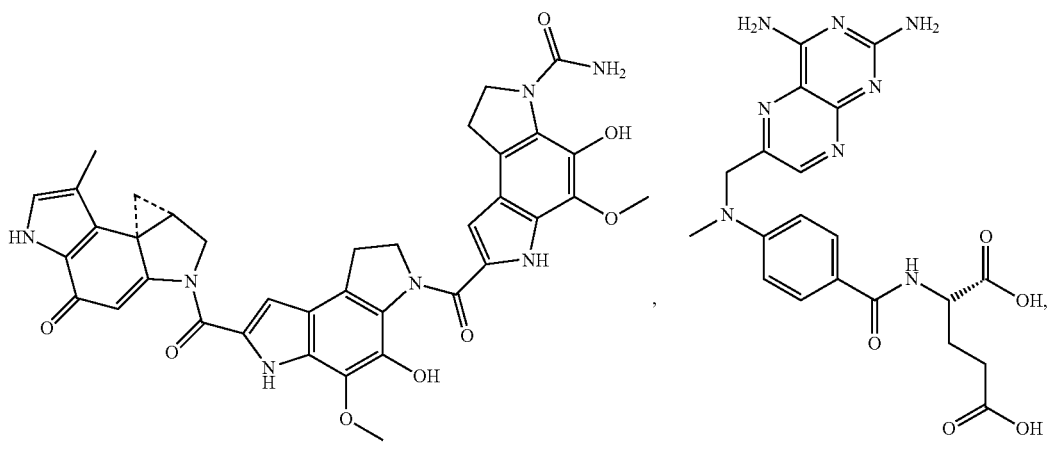
(+)-CC-1065
Methotrexate
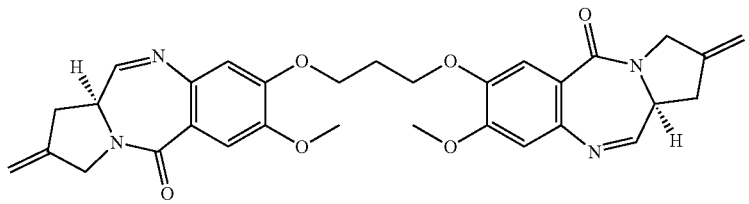
SJG-136
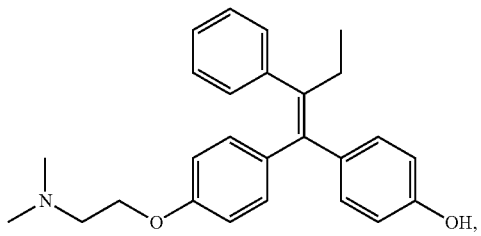
4-Hydroxytamoxifen
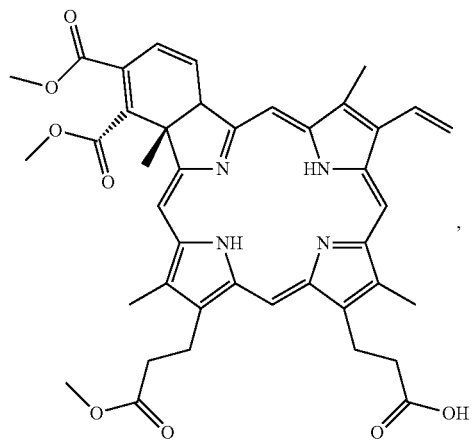
Verteporfin
CpG ODN 1826: 5'-TCC ATG ACG TTC CTG ACG TT-3'

One skilled in the art may make chemical modifications to the drug molecule in order to make reactions of the said drug molecule amenable or more convenient for purposes of preparing conjugates of the invention.

In another aspect, the present invention provides Ligand-Linker-Drug conjugates or a pharmaceutically acceptable salt or solvate thereof, represented by the general formulae:

(VII)

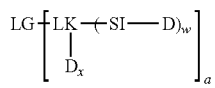
(VIII)

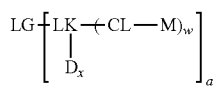
(IX)

wherein

LK is a linker moiety selected from Formula I, II or III and covalently attached to a ligand (LG) through a thioether bond formed between a sulfhydryl or thiol group (—SH) on the LG with the double bond of the LK;

each D, M, SI, CL, v, w and x are as previously defined;

a is an integer selected from 1 to 10 and is preferably 2 to 4;

LG is a ligand moiety having a reactive sulfhydryl or thiol group (—SH), either natively present as cysteine residue or introduced via protein engineering, and capable to bind to or reactively associate or complex with an antigen, receptor or other receptive moiety present on a surface of a particular cell which include, but are not limited to, antibody, antibody fragment, protein, peptide, polypeptide, lectins, non-peptides, carbohydrates, vitamins and nutrient-transport molecules. Preferably, the ligand is selected from abciximab, adalimumab, alemtuzumab, basiliximab, belimumab, bevacizumab, brentuximab, canakinumab, certolizumab, cetuximab, daclizumab, denosumab, eculizumab, efalizumab, gemtuzumab, golimumab, ibritumomab, infliximab, ipilimumab, motavizumab, muronomab-CD3, natalizumab, ofatumumab, omalizumab, palivizumab, panitumumab, raxibacumab, ranibizumab, rituximab, tocilizumab, tositumomab, trastuzumab, ustekinumab, anti-CD30 antibody cAC 10, RGD-peptide homing ligands, 2-[3(1,3-dicarboxypropyl)-ureido]pentanedioic acid (DUPA) targeting prostate specific membrane antigen (PSMA), epidermal growth factor, vascular endothelial growth factor, steroidal estrogens, somatostatin, bombesin, polyunsaturated fatty acids (e.g., linoleic acid, linolenic acid, arachidonic acid, eicosapentaenoic acid), lectins, folate, biotin, riboflavin, hyaluronic acid, transferrin.

The ligand molecule is covalently conjugated via the said —SH group with the thiol acceptor in the linker molecule by the formation of a thioether bond. It is well documented that a thiol group (—SH) can undergo Michael addition or click radical reaction with various carbon-carbon double bonds (enes or thiol acceptors), electron-rich or electron poor, under mild conditions with nearly quantitative yields and regiospecificity (Hoyle et al. *Angew. Chem. Int. Ed.* 2010, 49, 1540-1573). The thiol-ene chemistry is insensitive to ambient oxygen or water, requires only small concentrations of relatively benign catalysts, and has rapid reaction rates with reactions occurring either in bulk or in environmentally benign solvents over a large concentration range. The radical thiol-ene reactions can proceed via either UV irradiation (254 or 365 nm) with or without radical initiator (e.g., AIBN, ACVA, VA-044, diphenyl 2,4,6-trimethylbenzoyl phosphine oxide, 2,2-dimethoxy-2-phenylacetophenone, benzophenone, DL-Camphorquinone, dimethyl phenyl phosphine), thermally sensitive radical initiators without irradiation, or redox initiation without the need for elevated temperatures. Thus, the exceptional versatility and its propensity make the thiol-ene chemistry attractive and applicable to the Ligand-Linker and Ligand-Linker-Drug conjugate formation. However, due to the challenges of achieving the uniform light exposure and requiring light attenuation to uniformly attain bulk radical generation, the viability of photoinitiated radical thiol-ene reactions may be limited for large-scale syntheses. Therefore, Michael addition or thermal and redox initiated radical reactions may have the advantage at large scales.

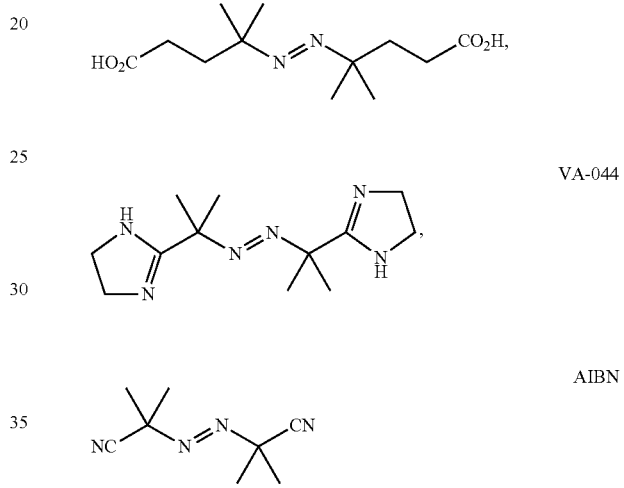

EXPERIMENTAL SECTION

The invention described above is illustrated by the examples shown below without limiting the scope of the invention.

Example 1

Penten-4-al was prepared following the literature procedures with modifications (Marta Rosillo M, et al. *Eur. J. Org. Chem.* 2008, 3917-3927). Thus, to a stirred suspension of pyridinium chlorochromate (38.8 g, 180 mmol) in dry $CH_2Cl_2$ (300 mL) was added all at once 4-penten-1-ol (10.34 g, 120 mmol) at ambient temperature. The stirring was prolonged for 3 h. The reaction mixture was then diluted with ether (400 mL) and decanted. The black gum was triturated again with ether (3×100 mL) and decanted. The combined organic solution was passed through a pad of silica gel. After the volatile organic solvents were distilled off at atmospheric pressure, the residue was distilled with fractions at 98-102° C.

collected to afford penten-4-al (4.6 g, 54.7 mmol, 45% yield) as clear colorless liquid, the chemical structure of which was confirmed by ¹H NMR.

Example 2

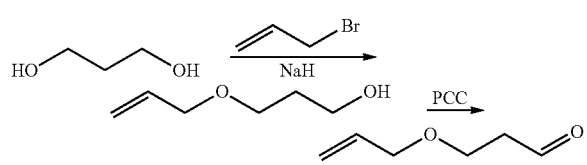

3-Allyloxypropional was prepared in a 2-step process following the literature procedures with modifications (Ting C M, et al. *Org. Lett.* 2011, 13, 1702-1705). Thus, to a stirred solution of 1,3-propanediol (2 g, 26.3 mmol) in THF (40 mL), NaH (60%, 1.05 g, 26.3 mmol) was added in portions. After completion of addition, the mixture was refluxed for 1 h and then cooled to room temperature. A solution of allyl bromide (2.16 mL, 24.9 mmol) in THF (20 mL) was added dropwise and the mixture stirred at room temperature overnight followed by reflux for 6 h. The mixture was cooled to room temperature and extracted with AcOEt (2×50 mL). The organic layers were combined, washed with brine, dried over Na₂SO₄ and concentrated under vacuum. The residue obtained was purified by silica gel column chromatography, eluting with hexane:AcOEt (3:1 to 2:1) to furnish 3-allyloxy-1-proanol (1.0 g, 34.5% yield) as a yellow oil.

Into a solution of 3-allyloxy-1-proanol (1.0 g, 8.6 mmol) in dry CH₂Cl₂ (20 mL) was added pyridinium chlorochromate (1.86 g, 8.6 mmol) and celite (1.86 g) in portions. After completion of addition, the mixture was stirred at room temperature for 3 h, diluted with hexane (20 mL) and passed through celite. The filtrate was concentrated to dryness to yield the desired aldehyde with at least 80% purity as shown by ¹H NMR, which was used directly for the next step.

Example 3

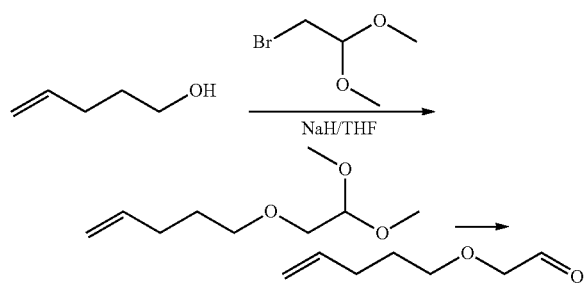

2-(Pent-4-enyloxy)acetaldehyde was prepared in a 2-step process following the literature procedures with modifications (Glaser M, et al. *Bioconjugate Chem.* 2008, 19, 951-957). Thus, to a stirring suspension of sodium hydride (60% in mineral oil, 2.85 g, 71.4 mmol) in THF (40 mL) under nitrogen atmosphere was added through an addition funnel a solution of 4-penten-1-ol (6.15 g, 71.4 mmol) in THF (20 mL) at room temperature. After completion of addition, the mixture was refluxed for 1 h and then cooled to room temperature. A solution of bromoacetaldehyde dimethyl acetal (11.5 g, 68 mmol) in THF (40 mL) was added dropwise at room temperature over a period of 20 min. The reaction mixture was then refluxed for 4 h, cooled to room temperature, and quenched with water (20 mL). The layers were separated and the aqueous layer was extracted with ethyl acetate (2×50 mL). The combined organic solutions were washed with brine (50 mL), dried over Na₂SO₄ and evaporated under vacuum. The crude residue was purified by flash silica gel chromatography eluting with step gradients of 0-10% ethyl acetate in hexane to afford 5-(2,2-dimethoxy-ethoxy)-pent-1-ene (5.5 g, 31.6 mmol, 44% yield).

A mixture of the above prepared acetal (5-(2,2-dimethoxy-ethoxy)-pent-1-ene, 1.0 g, 5.7 mmol) in formic acid (4 mL) and anhydrous pentane (6 mL) was stirred at room temperature for 3 h. The reaction mixture was diluted with CH₂Cl₂ (50 ml), quenched with water (5 mL), and neutralized by adding solid K₂CO₃. The layers were separated and the aqueous layer was extracted with CH₂Cl₂ (2×25 mL). The combined organic solutions were washed with brine (25 mL), dried over Na₂SO₄ and evaporated under vacuum to provide the crude 2-(pent-4-enyloxy)acetaldehyde (0.65 g, 5 mmol, 88% yield) which was 90% pure as shown by ¹H NMR and was used for the next step without further purification.

Example 4

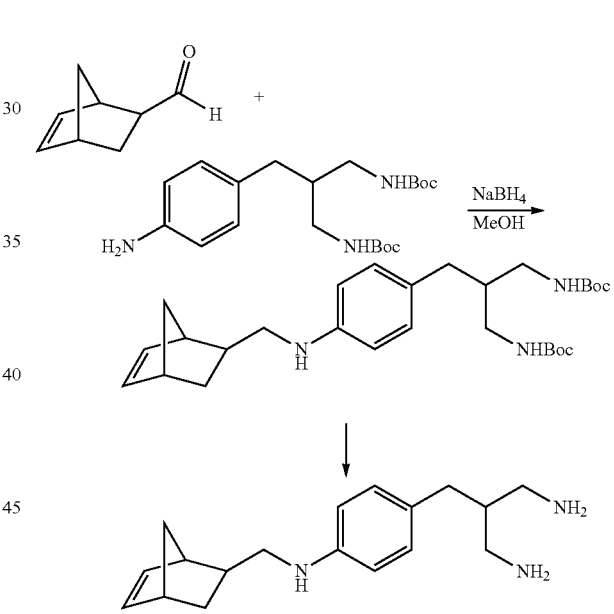

5-Norbornene-2-carboxaldehyde (0.047 g, 0.39 mmol) and the Boc-protected aniline derivative (0.155 g, 0.41 mmol), prepared according to the literature method (Palmer B D, et al. *J Med Chem.* 1990, 33, 3008-3014), were mixed and stirred in MeOH (2 mL) at room temperature under nitrogen atmosphere for 3 h, followed by addition of solid NaBH₄ (0.024 g, 0.63 mmol). The reaction mixture was stirred for 10 min at room temperature, quenched with 1 M NaOH (2 mL) and extracted with ethyl acetate (2×2 mL). The combined organic solutions were washed with brine (2 mL), dried over Na₂SO₄ and evaporated under vacuum to provide the desired product (0.18 g, 0.37 mmol, 95% yield) which was 95% pure as shown by HPLC and was confirmed by LC/MS (m/e 486, M+1).

The Boc-protecting groups were removed by treating with 6N HCl (2 mL) in MeOH (2 mL) at room temperature for 24 h. The solvents were all removed under vacuum at 50° C. and the residue was triturated with MBTE to afford off-white solid (0.13 g, 89% yield, assuming 3HCl salt). LC/MS indicated molecular ion of free base (m/e 286, M+1).

Example 5

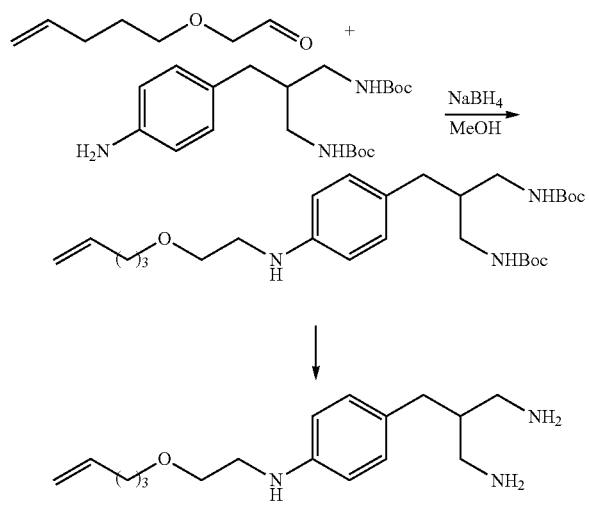

The procedures shown in Example 4 were followed for the reaction between 2-(pent-4-enyloxy)acetaldehyde (0.050 g, 0.39 mmol) and the Boc-protected aniline derivative (0.155 g, 0.41 mmol), followed by the reduction of NaBH₄ (0.024 g, 0.63 mmol), to provide the desired Boc-protected product (0.172 g, 0.35 mmol, 90% yield) which was 95% pure as shown by HPLC and was confirmed by LC/MS (m/e 492, M+1). The Boc-protecting groups were removed by treating with 6N HCl (2 mL) to afford white solid (0.128 g, 91% yield, assuming 3HCl salt). LC/MS indicated molecular ion of free base (m/e 292, M+1).

Example 6

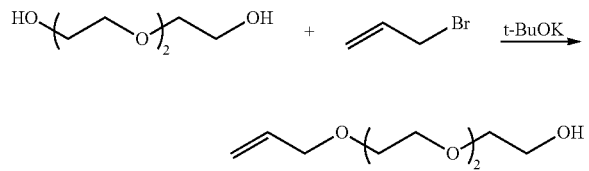

Allyl-triethylene glycol was prepared according to the literature method with modifications (Setz O, et al. *Angew Chem Int Ed Engl.* 1995, 34, 803-805). Thus, the mixture of triethylene glycol (11.83 g, 78.8 mmol), potassium t-butoxide (4.42 g, 39.4 mmol) and potassium iodide (0.65 g, 3.94 mmol) in THF (500 mL) was stirred at room temperature for 0.5 h, into which was added dropwise allyl bromide (4.767 g, 39.4 mmol) in THF (120 mL) over a period of 1.5 h. After continuing to be stirred at room temperature for 36 h, the mixture was filtered through a celite pad. The crude product, obtained after removal of solvents under vacuum, was purified by a silica gel column chromatography eluting with hexane/ethyl acetate (1:1) to afford the product (4.9 g, 25.8 mmol, 65% yield) with chemical structure confirmed by ¹H NMR and MS.

Example 7

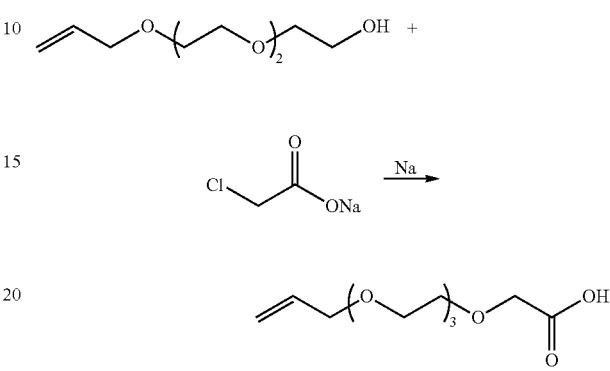

Allyl-triethylene glycolate acetic acid was prepared according to the literature method with modifications (Setz O, et al. *Angew Chem Int Ed Engl.* 1995, 34, 803-805). To the stirred solution of allyl-triethylene glycol (2.0 g, 10.52 mmol) in anhydrous THF (20 mL) was added Na (0.22 g, 9.47 mmol) at room temperature. After completion of addition, the mixture was refluxed till the disappearance of Na. The resulting solution was cooled to room temperature, into which sodium 2-chloroacetate (1.1 g, 9.47 mmol) was added. The mixture was stirred at room temperature overnight, followed by reflux for 3 h. After cooled to room temperature, the solvents were removed under vacuum and the residue was dissolved in water (50 mL). The solution was extracted with CH₂Cl₂ (4×30 mL) to remove impurities and then acidified to pH~7 with concentrated HCl. The aqueous solution was again extracted with CH₂Cl₂ (4×40 mL). The later extracts were combined, dried over Na₂SO₄ and concentrated to dryness to furnish product as a yellow oil (0.5 g, 1.91 mmol, 18% yield) with chemical structure confirmed by ¹H NMR and MS.

Example 8

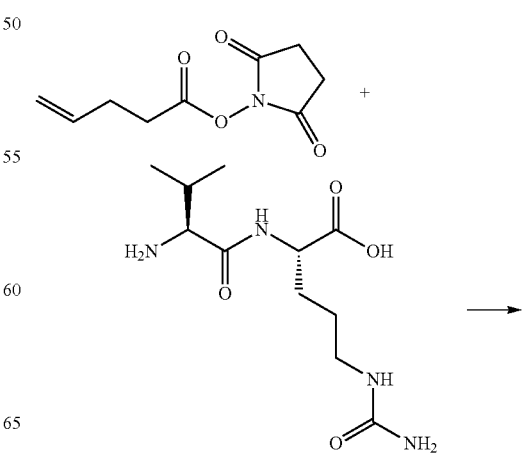

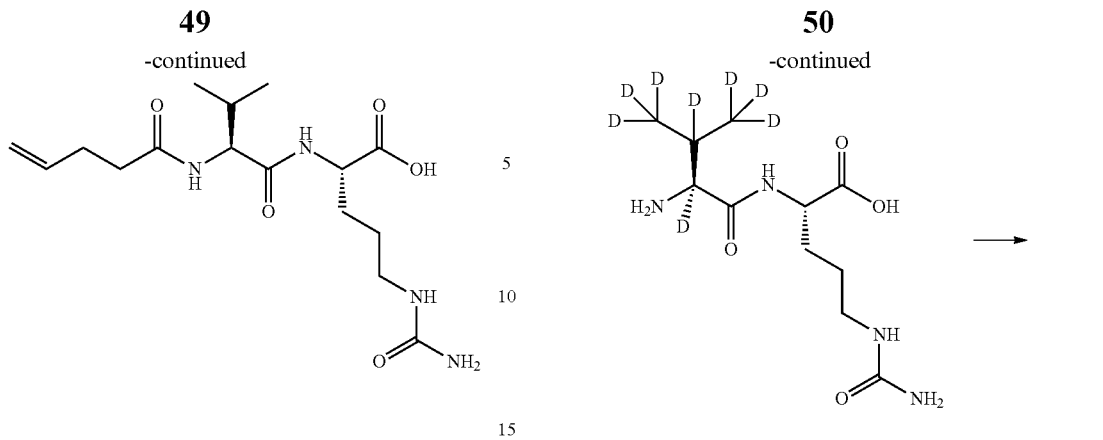

A mixture of N-succinimidyl 4-pentenoic acid ester (0.64 g, 3.25 mmol), prepared from 4-pentenoic acid and N-succinimidyl carbonate via conventional method, valine-citruline dipeptide trifluoroacetic acid salt (1.26 g, 3.25 mmol) which was prepared according to the literature method (Dubowchik G M, et al. *Bioconjugate Chem.* 2002, 13, 855-869), and NaHCO$_3$ (0.95 g, 11.31 mmol) in water (5 mL) and dimethoxyethane (17 mL) was stirred at room temperature overnight. The solvents were removed under vacuum and the residue was suspended in water (100 mL). An off-white solid product (0.8 g, 2.24 mmol, 69% yield) with chemical structure confirmed by $^1$H NMR and MS (m/e 457, M+1).

Example 9

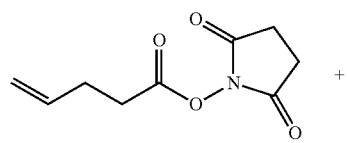

The same procedures shown in Example 7 was employed to prepare the deuterated derivative. Thus, a mixture of N-succinimidyl 4-pentenoic acid ester (0.21 g, 1.06 mmol), (valine-d$_8$)-citruline dipeptide trifluoroacetic acid salt (0.42 g, 1.06 mmol) which was prepared following the same procedures reported for the non-deuterated congener (Dubowchik G M, et al. *Bioconjugate Chem.* 2002, 13, 855-869), and NaHCO$_3$ (0.31 g, 3.69 mmol) in water (2 mL) and dimethoxyethane (6 mL) was stirred at room temperature overnight. The solvents were removed under vacuum and the residue was suspended in water (30 mL). An off-white solid product (0.25 g, 0.68 mmol, 64% yield) with chemical structure confirmed by $^1$H NMR and MS (m/e 388, M+1).

Example 10

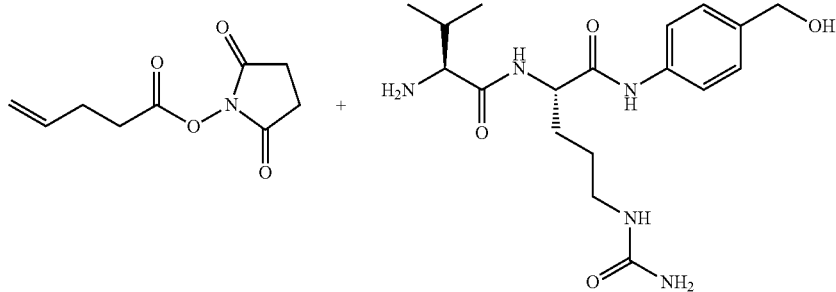

-continued

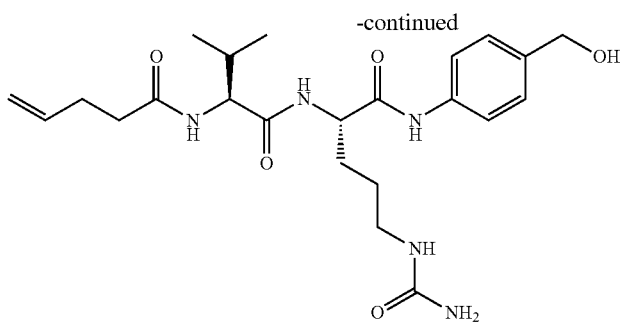

The titled compound was prepared using the same procedures shown in Example 7 from N-succinimidyl 4-pentenoic acid ester (0.64 g, 3.25 mmol), 4-hydroxymethylphenyl valine-citruline amide trifluoroacetic acid salt (1.7 g, 3.25 mmol), prepared according to the literature method (Dubowchik G M, et al. *Bioconjugate Chem.* 2002, 13, 855-869), and $NaHCO_3$ (0.95 g, 11.31 mmol) in water (5 mL) and dimethoxyethane (17 mL) to afford a slightly yellow solid product (1.05 g, 2.24 mmol, 70% yield) with chemical structure confirmed by $^1H$ NMR and MS (m/e 462, M+1).

Example 11

The titled compound was also prepared using the same procedures shown in Example 7 from N-succinimidyl 4-pentenoic acid ester (0.10 g, 0.5 mmol), 4-hydroxymethylphenyl (valine-$d_8$)-citruline amide trifluoroacetic acid salt (0.25 g, 0.5 mmol), prepared following the same procedures reported for the non-deuterated congener (Dubowchik G M, et al. *Bioconjugate Chem.* 2002, 13, 855-869), and $NaHCO_3$ (0.147 g, 1.75 mmol) in water (1 mL) and dimethoxyethane (4 mL) to afford a slightly yellow solid product (0.169 g, 0.36 mmol, 72% yield) with chemical structure confirmed by $^1H$ NMR and MS (m/e 470, M+1).

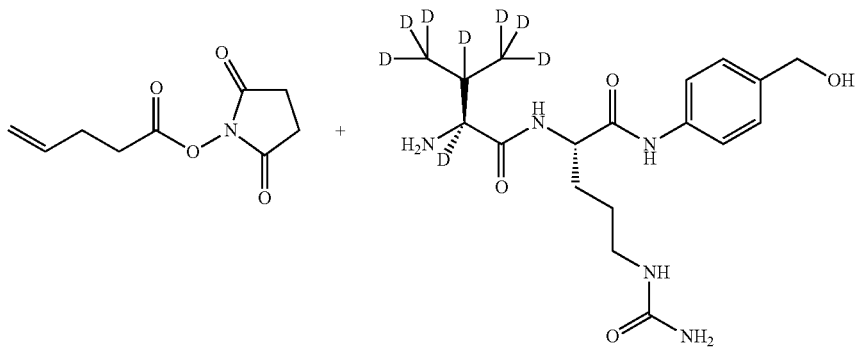

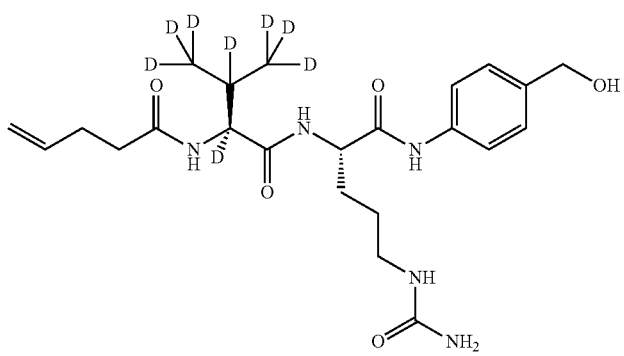

Example 12

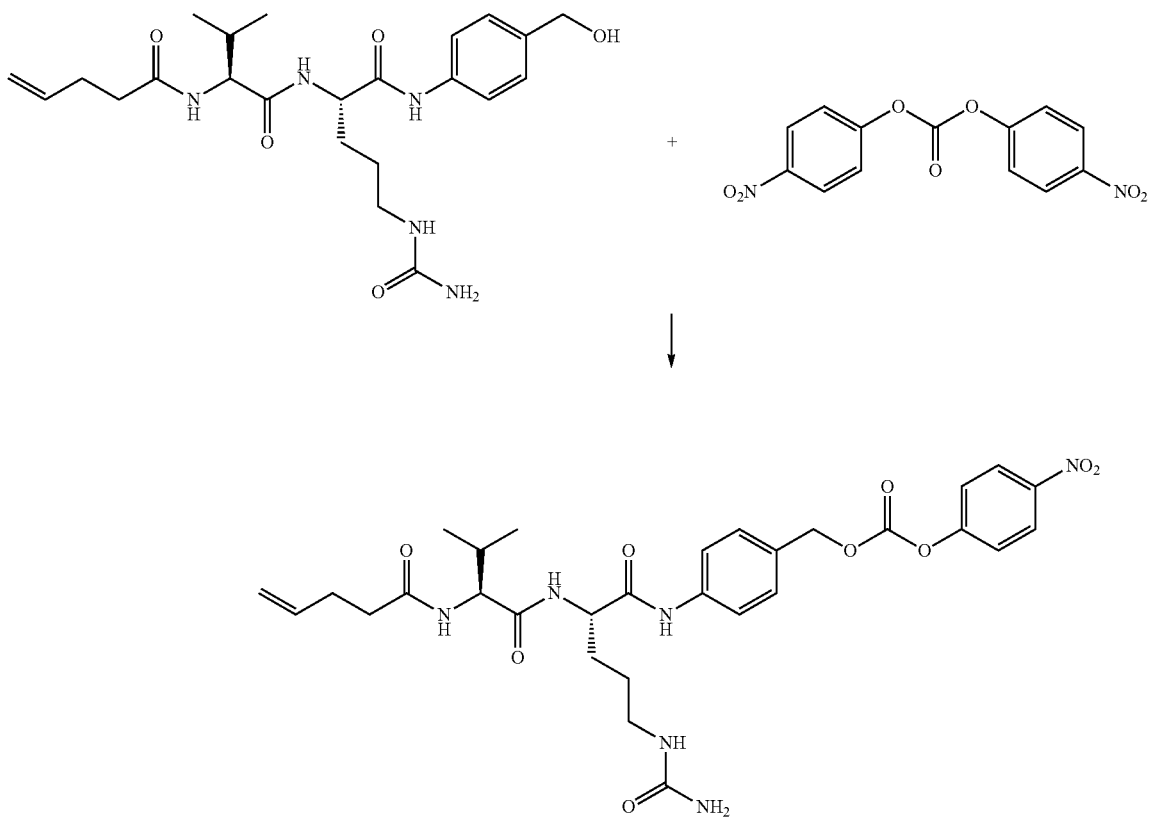 [SMILES: C=CCCC(=O)N[C@H](C(=O)N[C@@H](CCCNC(N)=O)C(=O)Nc1ccc(CO)cc1)C(C)C ; O=C(Oc1ccc([N+](=O)[O-])cc1)Oc1ccc([N+](=O)[O-])cc1 ; C=CCCC(=O)N[C@H](C(=O)N[C@@H](CCCNC(N)=O)C(=O)Nc1ccc(COC(=O)Oc2ccc([N+](=O)[O-])cc2)cc1)C(C)C]

The titled carbonate compound was prepared following the literature procedures with modifications (Dubowchik G M, et al. *Bioconjugate Chem.* 2002, 13, 855-869). Thus, 4-pentenoic amide of Val-Cit-PAB-OH (1.0 g, 2.17 mmol) prepared according to Example 8, bis(4-nitrophenyl) carbonate (1.32 g, 4.34 mmol), and N,N-diisopropylethylamine (DIPEA) (0.42 g, 3.25 mmol) were mixed and stirred in DMF (5 mL) at room temperature overnight. DMF was removed under vacuum and the crude product triturated with Et$_2$O. The solids were collected, washed successively with Et$_2$O (5 mL) and EtOAc (5 mL) and dried under vacuum to afford 1.1 g (1.75 mmol, 81% yield) of a slightly yellow solid product with chemical structure confirmed by $^1$H NMR and MS (m/e 627, M+1).

Example 13

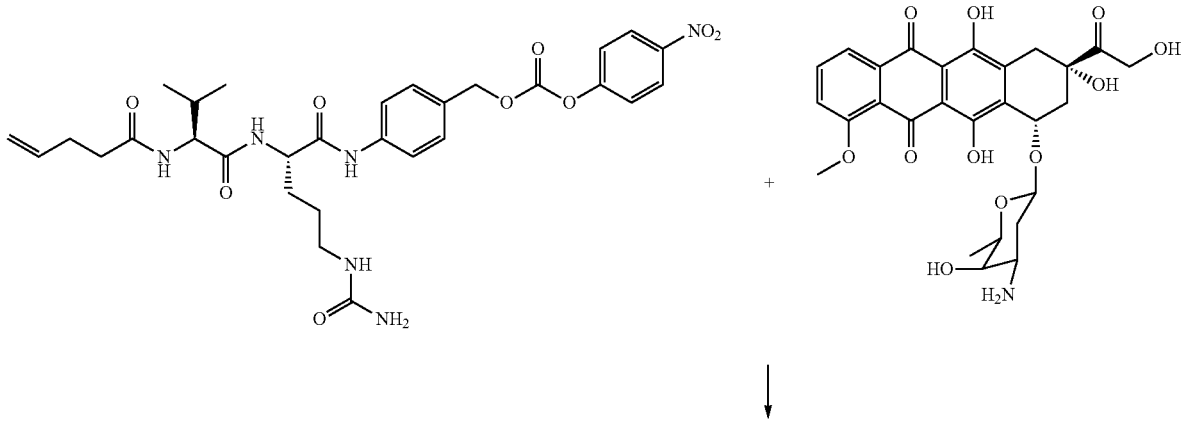

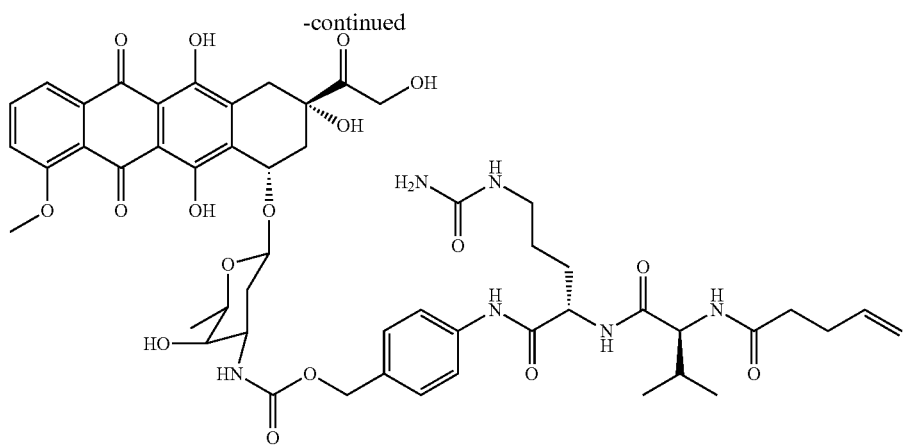

The titled doxorubicin-linker conjugate was prepared following the literature procedures with modifications (Dubowchik G M, et al. *Bioconjugate Chem.* 2002, 13, 855-869). Thus, 4-pentenoic amide of Val-Cit-PABC-PNP (0.200 g, 0.32 mmol), prepared according to Example 9, doxorubicin hydrochloride salt (0.19 g, 0.32 mmol), and N,N-diisopropylethylamine (DIPEA) (0.41 g, 0.32 mmol) were mixed and stirred in 1-methyl-2-pyrrolidinone (NMP) (10 mL) at room temperature in the dark over the weekend. The solution was concentrated under vacuum and the crude product purified by silica gel column chromatography, eluting with step-gradients of $CH_2Cl_2$/MeOH (10:1, 5:1 to 3:1) to furnish 58 mg (0.056 mmol, 17% yield) of a reddish solid product with chemical structure confirmed by $^1$H NMR and MS (m/e 1032, M+1; 1054, M+Na).

Example 14

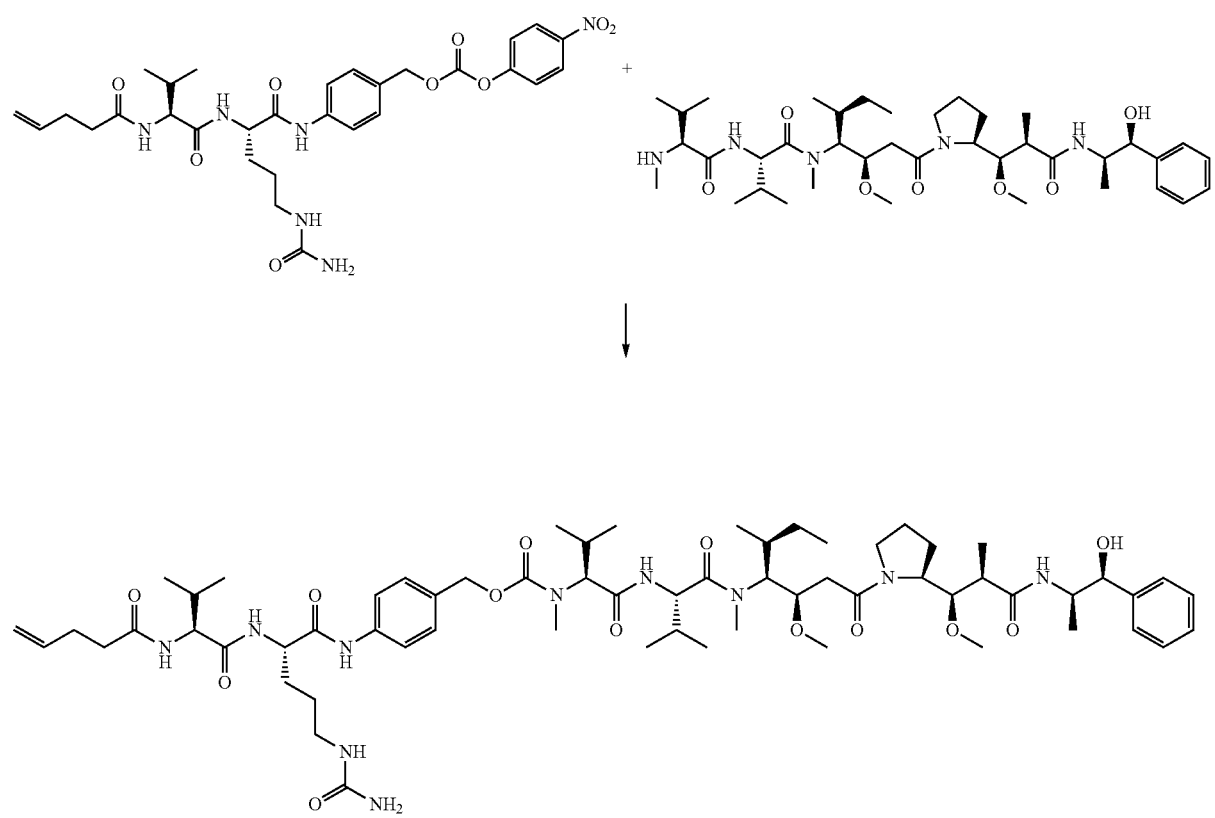

The titled N-monomethyl auristatin E-linker conjugate was prepared following the procedures shown in Example 12 from 4-pentenoic amide of Val-Cit-PABC-PNP (0.1 g, 0.16 mmol), N-monomethyl auristatin E (MMAE) (0.11 g, 0.16 mmol) which was prepared according to the literature method with modifications (Pettit G R, et al. *Anti-Cancer Drug Design* 1998, 13, 243-277), and N,N-diisopropylethylamine (DIPEA) (0.21 g, 0.16 mmol) were mixed and stirred in 1-methyl-2-pyrrolidinone (NMP) (10 mL) at room temperature over the weekend to furnish 48 mg (0.04 mmol, 25% yield) of white solid. MS (m/e): 1206, M+1; 1228, M+Na).

Example 15

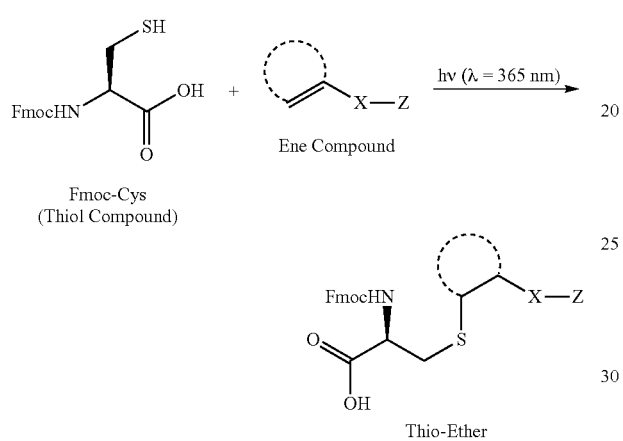

50 μL each of Fmoc-Cys (50 mM in acetonitrile), Ene Compounds (500 mM in pH 4.0 acetate buffer or acetonitrile) and VA-044 (50 mM in pH 4.0 acetate buffer) were added in 350 L of acetate buffer (0.2 M, pH 4.0) in a clear plastic tube at room temperature. The mixture was agitated to achieve a homogeneity and irritated under 365 nm in a Cole Parmer 9818 darkroom UV light box for 2 h. The reaction mixtures were analyzed by HPLC and MS to determine the completeness and product formation, with the results shown in the table below.

| Ene Compounds | Results |
|---|---|
| ⌇⌇⌇OH (allyl alcohol) | 1 Thio-ether Product/Fmoc-Cys Ratio = 66:34<br>Thio-ether Product Retention Time: 39.7 min<br>MS m/e: 402 (M + 1) |
| ⌇⌇⌇O⌇⌇OH | 2 Thio-ether Product/Fmoc-Cys Ratio = 75:25<br>Thio-ether Product Retention Time: 41.1 min<br>MS m/e: 446 (M + 1) |
| ⌇⌇O⌇⌇OH | 3 Thio-ether Product/Fmoc-Cys Ratio = 100:0<br>Thio-ether Product Retention Time: 39.5 min<br>MS m/e: 432 (M + 1) |
| ⌇⌇⌇⌇OH | 4 Thio-ether Product/Fmoc-Cys Ratio = 100:0<br>Thio-ether Product Retention Time: 43.7 min<br>MS m/e: 430 (M + 1) |
| norbornene-CH2-OH | 5 Thio-ether Product/Fmoc-Cys Ratio = 100:0<br>Thio-ether Product Retention Time: 45.2, 45.7, 46.3, 49.4, 50.8 and 52.9 min, respectively<br>MS m/e: 468 (M + 1) |
| norbornene-lactone | 6 Thio-ether Product/Fmoc-Cys Ratio = 100:0<br>Thio-ether Product Retention Time: 40.8 and 41.1 min<br>MS m/e: 508 (M + 1) |
| norbornene-lactone isomer | 7 Thio-ether Product/Fmoc-Cys Ratio = 100:0<br>Thio-ether Product Retention Time: 42.7 and 43.0 min<br>MS m/e: 508 (M + 1) |
| epoxy-norbornene-lactone | 8 Thio-ether Product/Fmoc-Cys Ratio = 100:0<br>Thio-ether Product Retention Time: 36.77 and 37.21 min<br>MS m/e: 510 (M + 1) |
| acrylic acid | 9 Thio-ether Product/Fmoc-Cys Ratio = Not Determined; majority of Fmoc-Cys remained unreacted<br>Thio-ether Product Retention Time: Not Determined<br>MS m/e: Not Determined |

Therefore, the reactivity of ene compounds in the VA-044 initiated Thio-Ene click reaction is in this order: 3~4~5~6~7~8>1~2>9, consistent with literature reported (Northrop B H, Coffey, R N. *J Am Chem Soc.* 2012, 134, 13804-13817). Generally speaking, electron-rich ene compounds were very good substrates for the Thio-Ene click reaction, but electron poor ene compound 9 was not.

Example 16

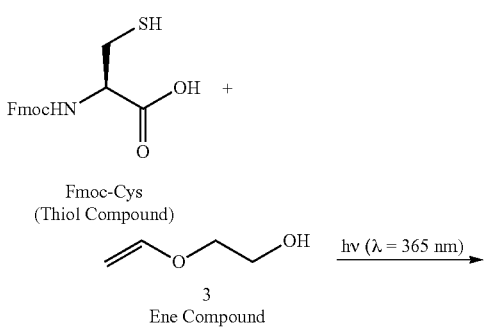

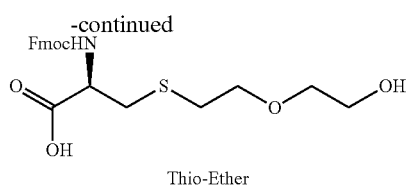

Thio-Ether

Effect of the concentration of ene compound was investigated following the procedures described in Example 14. Thus, 50 μL of Fmoc-Cys (50 mM in acetonitrile), various amount of Ene Compound 3 (500 mM in pH 4.0 acetate buffer) and 50 μL of VA-044 (50 mM in pH 4.0 acetate buffer) were added in 350 μL of acetate buffer (0.2 M, pH 4.0) in a clear plastic tube at room temperature. The homogenous solution was irritated under 365 nm. The reaction mixtures were monitored and analyzed by HPLC and MS to determine the completeness and product formation, with the results shown in the table below.

| Entry | Fmoc-Cys:3 Ratio | Time (minutes) | Results |
|---|---|---|---|
| 1 | 1:1 | 30 | Thio-ether Product/Fmoc-Cys Ratio = 25:75 |
|  |  |  | Thio-ether Product Retention Time: 39.7 min |
|  |  |  | MS m/e: 432 (M + 1) |
| 2 |  | 60 | Thio-ether Product/Fmoc-Cys Ratio = 30:70 |
| 3 |  | 90 | Thio-ether Product/Fmoc-Cys Ratio = 50:50 |
| 4 |  | 120 | Thio-ether Product/Fmoc-Cys Ratio = 67:33 |
| 5 |  | 240 | Thio-ether Product/Fmoc-Cys Ratio = 80:20 |
| 6 | 1:2 | 30 | Thio-ether Product/Fmoc-Cys Ratio = 40:60 |
| 7 |  | 60 | Thio-ether Product/Fmoc-Cys Ratio = 88:12 |
| 8 |  | 90 | Thio-ether Product/Fmoc-Cys Ratio = 95:5 |
| 9 |  | 120 | Thio-ether Product/Fmoc-Cys Ratio = 100:0 |
| 10 | 1:5 | 30 | Thio-ether Product/Fmoc-Cys Ratio = 94:6 |
| 11 |  | 60 | Thio-ether Product/Fmoc-Cys Ratio = 100:0 |
| 12 | 1:10 | 10 | Thio-ether Product/Fmoc-Cys Ratio = 89:11 |
| 13 |  | 20 | Thio-ether Product/Fmoc-Cys Ratio = 100:0 |

Therefore, complete conversion of the thiol compound was significantly shortened with the increase in the ratio of ene compound used.

Effect of the light wavelengths was investigated following the procedures described in Example 14. Thus, 50 μL each of Fmoc-Cys (50 mM in acetonitrile), Ene Compounds (500 mM in pH 4.0 acetate buffer) and VA-044 (50 mM in pH 4.0 acetate buffer) were added in 350 μL of acetate buffer (0.2 M, pH 4.0) in a clear plastic tube at room temperature. The homogenous solution was irritated under different light sources for 2 h or heated at 50° C. for 2 h. The reaction mixtures were analyzed by HPLC and MS to determine the completeness and product formation, with the results shown in the table below.

| Entry | Light Source (wave length) | Results |
|---|---|---|
| 1 | UV (365 nm) | Thio-ether Product/Fmoc-Cys Ratio = 60:40 |
|  |  | Thio-ether Product Retention Time: 53.1 min |
|  |  | MS m/e: 592 (M + 1) |
| 2 | UV (254 nm) | Thio-ether Product/Fmoc-Cys Ratio = 20:80 |
| 3 | White Light | No reaction |
| 4 | Heating at 50° C. | Thio-ether Product/Fmoc-Cys Ratio = 34:66 |

Irradiation under the UV light with wavelength at 365 nm yielded the highest conversion when VA-044 was used as the initiator.

Example 18

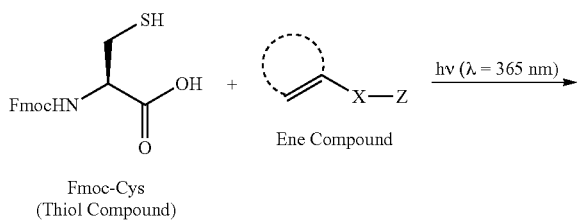

Fmoc-Cys
(Thiol Compound)

Ene Compound

Example 17

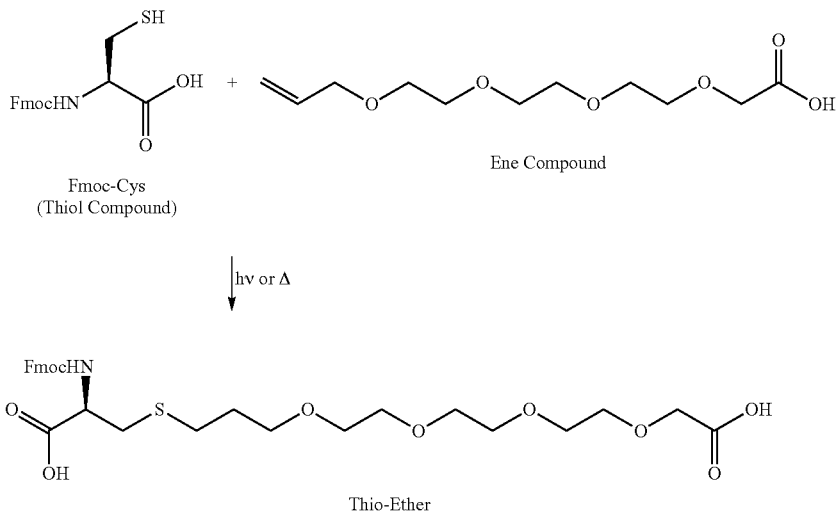

Fmoc-Cys
(Thiol Compound)

Ene Compound hv or Δ

Thio-Ether

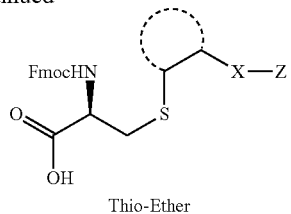

Thio-Ether

Effect of the initiators was investigated following the procedures described in Example 14. Thus, 50 μL each of Fmoc-Cys (50 mM in acetonitrile), Ene Compounds (500 mM in pH 4.0 acetate buffer) and different initiator (50 mM in pH 4.0 acetate buffer) were added in 350 μL of acetate buffer (0.2 M, pH 4.0) in a clear plastic tube at room temperature. The homogenous solution was irritated under 365 nm for 2 h. The reaction mixtures were analyzed by HPLC and MS to determine the completeness and product formation, with the results shown in the table below.

| Entry | Ene | Initiators | Results |
| --- | --- | --- | --- |
| 1 | allyl alcohol (CH₂=CHCH₂OH) | AIBN | No reaction detected |
| 2 | | AIBN (bis-imidazoline analog) | 70% of Fmoc-Cys converted to the desired thio-ether product detected at 39.7 min with MS m/e: 402 (M + 1) |
| 3 | | Benzophenone | All Fmoc-Cys converted to afford a complex mixture of products without the desired thio-ether |
| 4 | | DMPA (DPAP) | All Fmoc-Cys converted with the desired thio-ether product detected at 39.7 min along with 3 minor by-products |
| 5 | | PhPMe₂ DMPP | 50% of Fmoc-Cys converted with no formation of the desired product |
| 6 | acrylic acid (CH₂=CHCOOH) | AIBN | No reaction |
| 7 | | AIBN (bis-imidazoline analog) | <5% of Fmoc-Cys reacted with the desired thio-ether product undetected |

-continued

| Entry | Ene | Initiators | Results |
|---|---|---|---|
| 8 | | Benzophenone | 10% of Fmoc-Cys converted with the desired thio-ether product undetected |
| 9 | | (dimethoxy benzoin) | All Fmoc-Cys converted to furnish the desired thio-ether product along with two equal amounts of by-product with retention times at 33.0 and 37.9, respectively |
| 10 | | PhPMe$_2$ DMPP | 10% of Fmoc-Cys converted with the desired thio-ether product detected |

As can be seen, for both allyl alcohol and acrylic acid, DMPA (DPAP) was a better initiator than VA-044. The products formed from acrylic acid/DMPA were a bit complicated. DMPP initiated the photoreaction of acylic acid to form a single product with the molecular ion corresponding to the desired thio-ether product; but the rate deemed too slow.

Example 19

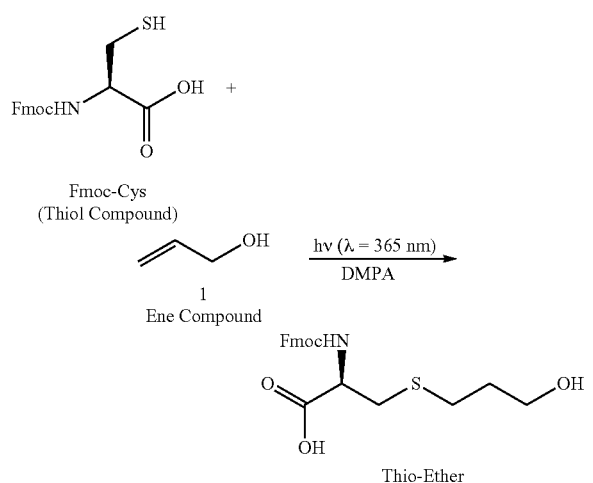

Due to limited solubility of initiator DMPA in aqueous media, effects of solvents and concentrations of ene compound were investigated, following the procedures described in Example 14. Thus, 50 μL of Fmoc-Cys (50 mM in acetonitrile), various volumes of Ene Compound 1 (500 mM in acetonitrile) and 50 μL of DMPA (50 mM in acetonitrile) were added in 350 μL of acetate buffer (0.2 M, pH 4.0) or 350 μL of acetonitrile in a clear plastic tube at room temperature. The homogenous solution was irritated under 365 nm. The reaction mixtures were monitored and analyzed by HPLC and MS to determine the completeness and product formation, with the results shown in the table below.

| Entry | Fmoc-Cys/Ene | Time (minutes) | Results |
|---|---|---|---|
| 1 | 1:10 | 15 | Thio-ether Product/Fmoc-Cys Ratio = 75:25 Thio-ether Product Retention Time: 39.7 min MS m/e: 402 (M + 1) |
| 2 | | 30 | Thio-ether Product/Fmoc-Cys Ratio = 90:10 |
| 3 | | 60 | Thio-ether Product/Fmoc-Cys Ratio = 100:0 |
| 4 | 1:5 | 30 | Thio-ether Product/Fmoc-Cys Ratio = 70:30 |
| 5 | | 60 | Thio-ether Product/Fmoc-Cys Ratio = 100:0 |
| 6 | 1:2 | 30 | Thio-ether Product/Fmoc-Cys Ratio = 45:55 |
| 7 | | 60 | Thio-ether Product/Fmoc-Cys Ratio = 100:0 |
| 8 | 1:1 | 30 | Thio-ether Product/Fmoc-Cys Ratio = 20:80 |
| 9 | | 60 | Thio-ether Product/Fmoc-Cys Ratio = 85:15 |
| 10 | | 120 | Thio-ether Product/Fmoc-Cys Ratio = 100:0 |
| 11* | 1:10 | 120 | Thio-ether Product/Fmoc-Cys Ratio = 25:75 |

The DMAP initiated click Thiol-Ene reactions in acetate buffer/acetonitrile (7:3) appeared to be less concentration-dependent when compared to VA-044 initiated reaction in acetate buffer/acetonitrile (9:1) as shown in Example 14. At all ratios tested except for the 1:1 ratio, the reaction was completed within 1 h. The DMAP initiated click Thiol-Ene reaction was much slower in acetonitrile than in aqueous solutions.

Example 20

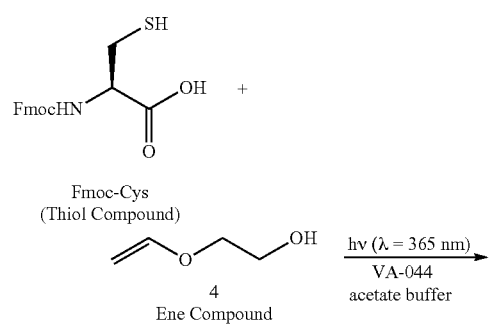

-continued

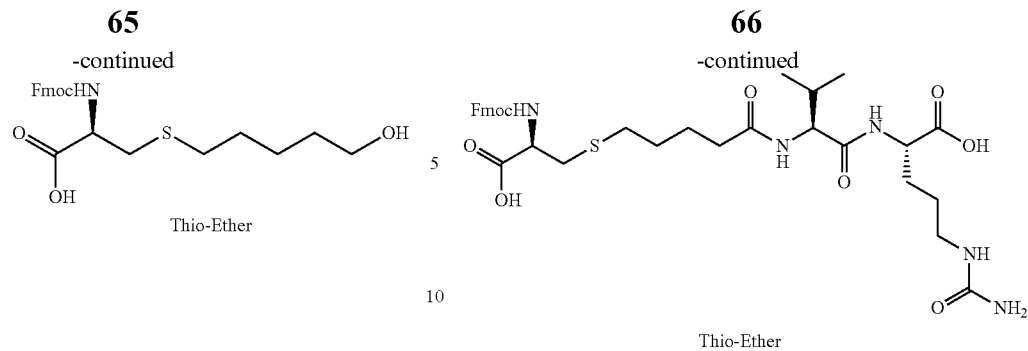

Thio-Ether

To further confirm the structure of thio-ether product, a click Thiol-Ene reaction was scaled up to isolate the thio-ether formed. Thus, 5 mL of 0.5 M 4-penten-1-ol (in acetate buffer), 5 mL of 0.05 M VA-044 (in acetate buffer), 5 mL of 0.05 M Fmoc-Cys (in acetonitrile) and 35 mL of acetate buffer (0.2 M, pH 4.0) were mixed in a glass bottle and irradiated under 365 nm for 4 h, whereupon the HPLC indicated the complete conversion of Fmoc-Cys. The reaction mixture was then extracted with AcOEt, dried over $Na_2SO_4$ and concentrated to provide the crude product which was purified by silica gel column chromatography, eluting with $CH_2Cl_2$/MeOH (5:1 to 3:1) to afford an oil (35 mg). $^1$H-NMR ($CDCl_3$, 300 MHz): δ (ppm) 7.87 (d, 2 H), 7.70 (d, 2H), 7.39 (t, 2 H), 7.29 (t, 2H), 7.02 (d, 1H), 4.34-4.16 (m, 3 H), 4.00-3.89 (m, 1 H), 3.32 (t, 2H), 2.95 (dd, 1H), 2.71 (dd, 1H), 2.50-2.4 (m, 2 H), 1.5-1.24 (m, 6 H). MS (m/e): 445 (M+1).

Example 21

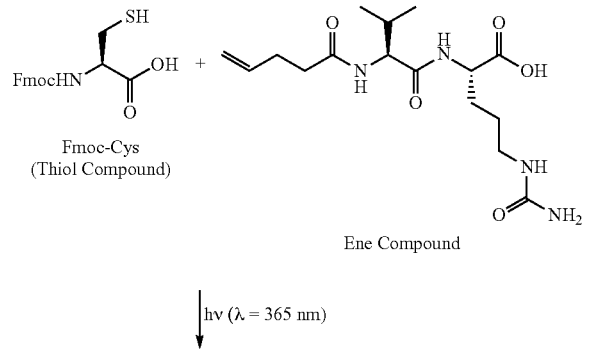

The thio-ether compound was prepared according to the procedures shown in Example 14 from 50 μL each of Fmoc-Cys (50 mM in acetonitrile), Ene Compounds (500 mM in pH 4.0 acetate buffer or acetonitrile) and VA-044 (50 mM in pH 4.0 acetate buffer) in 350 μL of acetate buffer (0.2 M, pH 4.0) under 365 nm irradiation 2 h. MS (m/e): 700 (M+1), 722 (M+Na).

Example 22

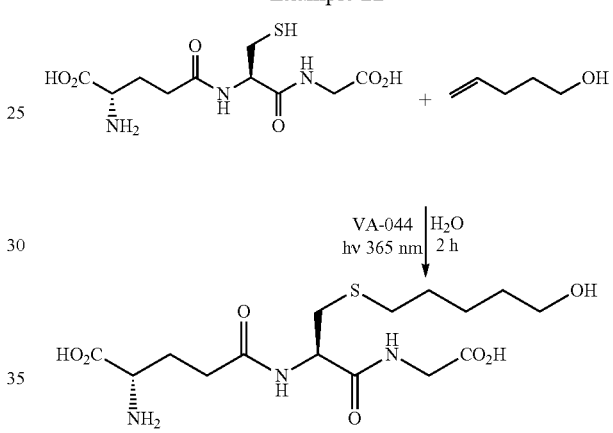

Glutathione (76.8 mg, 0.25 mmol), 4-penten-1-ol (215.3 mg, 2.5 mmol) and VA-044 (80.8 mg, 0.32 mmol) were mixed in 50 mL of water and irradiated at 365 nm for 3 h. The reaction mixture was extracted with AcOEt (20 mL×3). The aqueous layer was concentrated under vacuum at 80° C. to afford a 175 mg of solid residue, which was triturated with i-PrOH. The precipitates were collected and dried to afford 100 mg product (quantitative yield). MS (m/e): 394 (M+1).

The same reaction proceeded to completion in a 1:2 mixture of acetate buffer (0.2 M, pH 4.0) and DMF as shown by HPLC.

Example 23

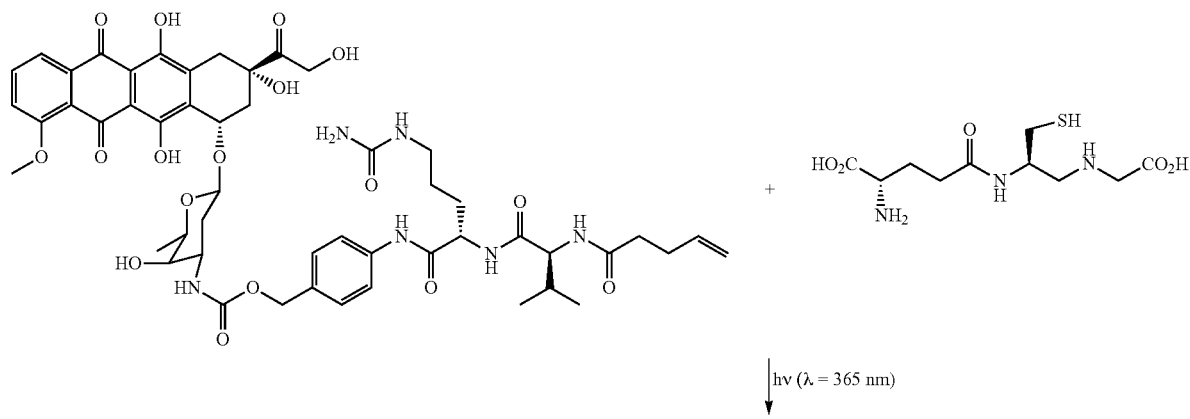

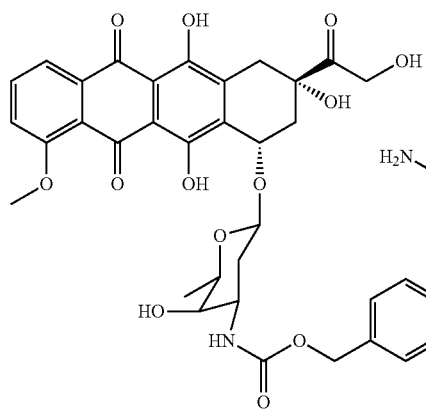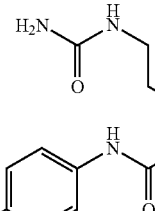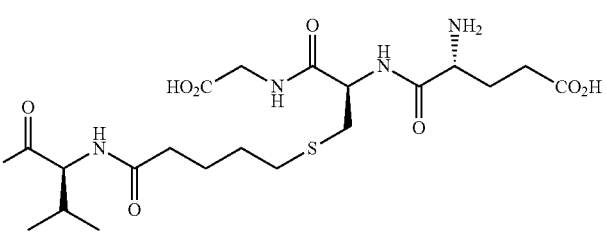

The glutathione-doxorubicin conjugate was prepared following the procedures shown in Example 21 from glutathione (14.9 mg, 48 μmol), doxorubicin-linker conjugate (5 mg, 4.8 μmol) and VA-044 (3.1 mg, 9.6 μmol) in 0.2 mL of acetate buffer (0.2 M, pH 4.0) and 0.4 mL DMF at room temperature under 365 nm irradiation overnight to afford the titled product (5 mg, 3.7 μmol, 77% yield). MS (m/e): 1338 (M+1), 1360 (M+Na).

Example 24

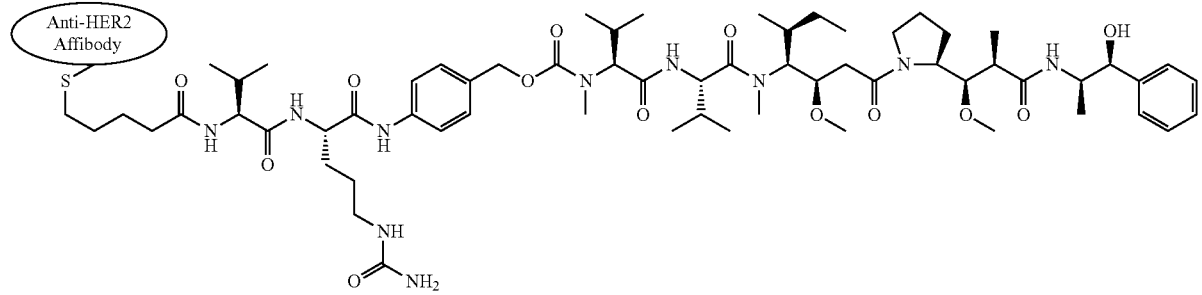 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCCCSC)C(C)C)cc1)C(C)C]

The Anti-HER2 Affibody-MMAE conjugate was prepared according to the procedures shown in Example 21 from Anti-HER2 Affibody (Affibody AB, Sweden, 100 μg) and 4-pentenoyl-Val-Cit-PABC-MMAE (5 mg) in PBS.

Example 25

Hydrolysis kinetics of conjugates was evaluated under different pH conditions. Thus, conjugate prepared in Example 23 was dissolved at an approximately 10 mg/mL of concentration in either acetate buffer (0.2 M, pH 4.0) or phosphate buffer (0.2 M, pH 7.0). The solutions were incubated at 37° C. and samples were taken at timed intervals and analyzed by reverse phase HPLC for the release of doxorubicin. The results were expressed as percents of total doxorubicin released and half-lives for the appearance of doxorubicin were calculated.

Example 26

In vitro cytotoxicity assays were performed following the conventional MTS cell viability method. Thus, cells were plated, the evening before treatment, for each treatment on 96-well plates ($1\times10^4$ cells/well) in 100 μL volume per well. Compound solutions were prepared by diluting each test compound in DMSO (10 mM) with the appropriate cell growth media for each individual cell line. Cells were treated by aspirating plating media from each well and adding 80 μL of each test solution in serial dilutions to the adherent cells. All treatments were performed in triplicate. Growth media (80 μL) was added to 3 blank wells (no cells) to measure background from the growth media. Growth media alone (no DMSO or test compound) was added to 3 wells containing cells to measure the baseline MTS activity. Vehicle (DMSO) control in serial dilutions, added to cells, was also included to monitor basal toxicity from DMSO. Cells were incubated at 37° C. for 72 h, or 120 h for the OVCAR cell lines. MTS reagent (per 96-well plate) were prepared by combining 2 mL of MTS working solution (Cell Titer Aqueous Non-Radioactive Cell Proliferation Assay, Promega), 100 μL of 0.92 mg/mL phenazine methosulfate/Dulbecco's PBS and 2.1 mL growth media. MTS reagent (40 μL) was added to each well and incubated at 37° C. for 1.5 to 4 h. Plates were gently shaken by hand until solution in each well appeared homogenous. Absorbances at 490 nm were measured on a Wallac Victor II plate reader at multiple time points following the addition of MTS reagent for each plate. Triplicate absorbance (490 nm) measurements were averaged following background (no cell) subtraction for each drug concentration. Percent Cell Viability was calculated for each drug concentration using the following equation:

{[Absorbance (analog treated)]/[Absorbance (DMSO treated)]}×100%

Percent viability (y-axis) was plotted against drug concentration (x-axis) and the resulting graph was used to determine the 50% inhibitory concentration ($IC_{50}$) for each drug.

What is claimed is:

1. A method of preparing a Ligand-Linker-Drug conjugate compound,
the method comprising
(a) coupling a linker (LK) compound selected from Formula I, II or III

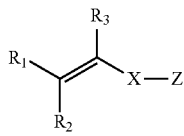
(I)

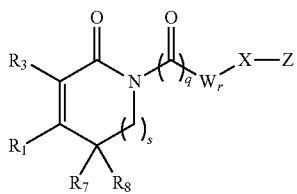
(II)

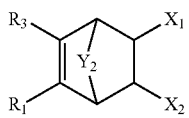
(III)

wherein $R_1$, $R_2$ and $R_3$ are independently selected from H, deuterium, halogen, CN, $NO_2$, HC(O), $CO_2H$, $C(O)NH_2$, $S(O)_2OH$, $S(O)_2NH_2$, a straight or branched $C_{1-8}$ alkyl, aryl-$C_{1-8}$ alkyl, heterocycle-$C_{1-8}$ alkyl, cyclo($C_{3-9}$)alkyl, aryl, heterocycle, $R_4C(O)$, $R_4O$, $R_4S$, $R_4S(O)$, $R_4S(O)_2$, $R_4NH$, $R_4R_5N$, $C(Y)OR_4$, $C(Y)SR_4$, $C(Y)NHR_4$, $C(Y)NR_4R_5$, $R_4OC(Y)$, $R_4SC(Y)$, $R_4NHC(Y)$, $R_4R_5NC(Y)$, $R_4OS(O)_2$, H—Y—$(CH_2CH_2O)_m$, $R_4$—Y—$(CH_2CH_2O)_m$, $R_4C(Y)$—O—$(CH_2CH_2O)_m$, $R_4C(Y)$—S—$(CH_2CH_2O)_m$, $R_4C(Y)$—NH—$(CH_2CH_2O)_m$, $R_4C(Y)$—N($R_5$)—$(CH_2CH_2O)_m$, or —X—Z, wherein the aryl comprises phenyl or naphthyl;
the heterocycle comprises
a 5 or 6 membered aromatic heterocycle selected from the group consisting of pyridyl, diazinyl, pyrimidinyl, 5-methoxy pyrimidinyl, (1,2,4)triazine-3,5-dione-6-yl, 6-mercaptopyrimidine-4-yl, pyrrolyl, pyrazolyl, imidazolyl, oxazolyl, isoxazolyl, thiazolyl, isothiazolyl, furanyl, and thienyl
a 3 to 9 membered non-aromatic heterocycle selected from the group consisting of piperazinyl, 4-methyl piperazinyl, pyrrolidinyl, imidazolidinyl, imidazolinyl, thiazolidinyl, thiazolinyl, isothiazolidinyl, isothiazolinyl, pyranyl, and morpholinyl; or
a polycyclic heterocycle selected from the group consisting of indolyl, benzthienyl, benzofuranyl, isoindolyl, isobenzothienyl, and isobenzofuranyl;

wherein each alkyl, cycloalkyl, aryl, and heterocycle are each optionally substituted with one or more groups (e.g., 1, 2, or 3 group) which are each independently halogen, CN, $N_3$, $NO_2$, OH, SH, $NH_2$, HONH, HON=, $CO_2H$, $C(O)NH_2$, $S(O)_2OH$, $S(O)_2NH_2$, $C_{1-8}$ alkyl, $R_4O$, $R_4S$, $R_4S(O)$, $R_4S(O)_2$, $R_4NH$, $R_4R_5N$, $R_4ONH$, $R_4ON=$, $R_4C(O)$, $R_4C(Y)O$, $R_4C(Y)S$, $R_4C(Y)NH$, $R_4C(Y)N(R_5)$, $C(Y)OR_4$, $C(Y)SR_4$, $C(Y)NHR_4$, $C(Y)NR_4R_5$, $R_4OC(Y)O$, $R_4OC(Y)S$, $R_4OC(Y)NH$, $R_4OC(Y)NR_5$, $R_4SC(Y)O$, $R_4SC(Y)S$, $R_4SC(Y)NH$, $R_4SC(Y)NR_5$, $R_4NHC(Y)O$, $R_4NHC(Y)S$, $R_4NHC(Y)NH$, $R_4NHC(Y)NR_5$, $R_4R_5NC(Y)O$, $R_4R_5NC(Y)S$, $R_4R_5NC(Y)NH$, $R_4R_5NC(Y)NR_5$, $S(O)_2OR_4$, $S(O)_2SR_4$, $S(O)_2NHR_4$, $S(O)_2NR_4R_5$, H—Y—$(CH_2CH_2O)_m$, $R_4$—Y—$(CH_2CH_2O)_m$, $R_4C(Y)$—O—$(CH_2CH_2O)_m$, $R_4C(Y)$—S—$(CH_2CH_2O)_m$, $R_4C(Y)$—NH—$(CH_2CH_2O)_m$, $R_4C(Y)$—N($R_5$)—$(CH_2CH_2O)_m$, X—$(CH_2CH_2O)_m$, —X—Z, or $R_1$ and $R_2$, $R_1$ and $R_3$ taken together with the carbon atoms to which they are attached form a cyclo($C_{3-9}$) alkyl, aryl, or heterocycle, wherein each alkyl, cycloalkyl, aryl, and heterocycle are each optionally substituted with one or more groups as previously defined;

$R_4$ and $R_5$ above are independently selected from a straight or branched $C_{1-8}$ alkyl, aryl-$C_{1-8}$ alkyl, heterocycle-$C_{1-8}$ alkyl, cyclo($C_{3-9}$)alkyl, aryl, heterocycle, or $R_4$ and $R_5$ taken together with the nitrogen atom to which they are attached form a cyclo($C_{3-9}$) alkyl, aryl, or heterocycle, wherein each alkyl, cycloalkyl, aryl, and heterocycle are each optionally substituted with one or more groups as previously defined;

each Y is independently selected from O, S, NH, $NR_4$, wherein $R_4$ is defined as above;

each Z is selected from OH, SH, NCS, NCO, $NHR_6$, $CONR_4R_5$, $CONHR_6$, $CO_2R_6$, $C(O)SR_6$, $C(O)R_6$, where $R_4$ and $R_5$ are defined as above; $R_6$ is H, $C_{1-8}$ alkyl, cyclo($C_{3-9}$)alkyl, aryl, or heterocycle, wherein each alkyl, cycloalkyl, aryl, and heterocycle are each optionally substituted with one or more groups as previously defined;

$R_7$, $R_8$ are independently selected from H, deuterium, and F; or $R_7$ and $R_8$ can be taken together to form =O and =S;

$Y_2$ is independently selected from $CH_2$, O, S, NH, and $NR_4$; wherein $R_4$ is defined as above;

each X is a spacer independently selected from:

$[C(O)]_n$—$W_o$—$[C(O)]_p$—$\{Y_1$—$[C(O)]_q$—$W_r\}_s$—$[C(O)]_q$-$(AA)_t$-, $[C(O)]_n$—$W_o$—$[C(O)]_p$—$[Y_1$—$(CH_2CH_2O)_m]_u$—$W_r$—$[C(O)]_q$-$(AA)_t$-, $[C(O)]_n$—$W_o$—$[C(O)]_p$—$[Y_1$—$(CH_2CH_2O)_m]_u$—$[C(O)]_q$—$W_r$-$(AA)_t$-, $[C(O)]_n$—$W_o$—$[C(O)]_p$—$[Y_1$—$(CH_2CH_2O)_m]_u$—C(O)—$Y_1$—$W_r$-$(AA)_t$-, $[C(O)]_n$—$W_o$—$[C(O)]_p$—$[Y_1$—$(CH_2CH_2O)_m]_u$—$W_r$—C(O)—$Y_1$—$W_r$-$(AA)_t$-, $[C(O)]_n$—$W_o$—$[C(O)]_p$—$[Y_1$—$(CH_2CH_2O)_m]_u$—$W_r$—$Y_1$—$[C(O)]_q$—$W_r$-$(AA)_t$-, $[C(O)]_n$—$W_o$—$[C(O)]_p$—$[Y_1$—$(CH_2CH_2O)_m]_u$—$W_r$—$Y_1$—C(O)—$Y_1$—$W_r$-$(AA)_t$-, $[C(O)]_n$—$W_o$—$[C(O)]_p$—$[Y_1$—$(CH_2CH_2O)_m]_u$-$(AA)_t$-$[Y_1$—$(CH_2CH_2O)_m]_u$—$W_r$—, $[C(O)]_n$—$W_o$—$[C(O)]_p$—$\{Y_1$—$[C(O)]_q$—$W_r\}_s$-$(AA)$-$\{Y_1$—$[C(O)]_q$—$W_r\}_s$—$[Y_1$—$(CH_2CH_2O)_m]_u$—$[C(O)]_q$—$W_r$-$(AA)_t$-, $[C(O)]_n$—$W_o$—$[C(O)]_p$—$\{Y_1$—$[C(O)]_q$—$W_r\}_s$-$(AA)$-C(O)—$\{Y_1$—$[C(O)]_q$—$W_r\}_s$—$[Y_1$—$(CH_2CH_2O)_m]_u$—$[C(O)]_q$—$W_r$-$(AA)_t$-, $[C(O)]_n$—$W_o$—$[C(O)]_p$—$\{Y_1$—$[C(O)]_q$—$W_r\}_s$-$(AA)$-$\{Y_1$—$[C(O)]_q$—$W_r\}_s$—C(O)—$[Y_1$—$(CH_2CH_2O)_m]_u$—$[C(O)]_q$—$W_r$-$(AA)_t$-, wherein each W is selected from a straight or branched $C_{1-8}$ alkyl, aryl-$C_{1-8}$ alkyl, heterocycle-$C_{1-8}$ alkyl, cyclo($C_{3-9}$)

alkyl, aryl, or heterocycle, wherein each alkyl, cycloalkyl, aryl, and heterocycle are each optionally substituted with one or more groups as previously defined;

each AA is an amino acid residue sequence independently selected from the group, consisting of alanine, glycine, isoleucine, leucine, methionine, phenylalanine, proline, tryptophan, valine, lysine, lysine protected with acetyl or formyl, arginine, arginine protected with tosyl or nitro groups, histidine, ornithine, ornithine protected with acetyl or formyl, citrulline, and combinations thereof;

each m is an integer independently selected from 1 to 20;
each n, o, p, q, r and t is an integer independently selected from 0 and 1; when o is 0, n and p cannot be 1;
each s is an integer independently selected from 0 to 8;
each u is an integer independently selected from 1 to 8;
$X_1$ and $X_2$ are independently selected from H, deuterium, —X—Z, wherein X and Z are defined as above, or $X_1$ and $X_2$ taken together can form a cyclic ring;
each $Y_1$ is selected from O, S, NH, $NR_4$, N—$[C(O)]_q$—$W_r$—X—Z, wherein $R_4$, W, X, Z, r and q are defined as above;

with a proviso that, when $R_1$ and $R_3$ are both H and s is 0, $R_7$ and $R_8$ together cannot be =O in Formula II;

with a drug (D) payload via group Z of the LK and a functional group of D to form a Linker-Drug conjugate compound selected from the formulae

(IV)

or (V)

(VI)

wherein
LK is a linker moiety selected from Formula I, II or III;
D is a drug moiety independently selected from the group selected from doxorubicin, vincristine, monomethyl auristatin E, monomethyl auristatin F, monomethyl dolastatin 10, maytansinoids, and calicheamicin;
M is a radioisotope selected from $^{211}$At, $^{225}$Ac, $^{213}$Bi, $^{60}$Co, $^{125}$I, $^{131}$I, $^{111}$In, $^{177}$Lu, $^{32}$P, $^{223}$Ra, $^{186}$Re, $^{188}$Re, $^{153}$Sm, $^{227}$Th and $^{90}$Y;
SI is a tethering group or self-immolative moiety that, upon a single activation event when internalized by the target cell or on the target cell surface, leads to a spontaneous and rapid release of the fully active drug;
CL is a metal chelating moiety that is able to chelate and hold the radioisotope and prevent it from premature release and off-target cell destruction;
a is an integer selected from 1 to 10;
v and w are integers independently selected from 1 to 10;
x is an integer selected from 0 to 9; provided that the sum of w and x does not exceed 10;
and
(b) reacting a sulfhydryl or thiol group (—SH) on the ligand (LG) moiety with the double bond on the Linker-Drug conjugate compound selected from Formula IV, V or VI to form a Ligand-Linker-Drug conjugate compound selected from the formulae

(VII)

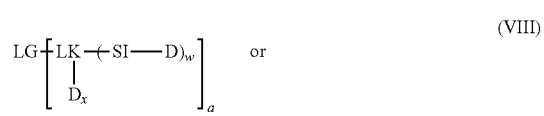

or (VIII)

(IX)

wherein
D, SI, CL M, a, v, w and x are defined above;

LK is a linker moiety selected from Formula I, II or III and covalently attached to a ligand (LG) through a thioether bond formed between a sulfhydryl or thiol group (—SH) on the LG with the double bond of the LK; and LG is selected from abciximab, adalimumab, alemtuzumab, basiliximab, belimumab, bevacizumab, brentuximab, canakinumab, certolizumab, cetuximab, daclizumab, denosumab, eculizumab, efalizumab, gemtuzumab, golimumab, ipilimumab, ibritumomab, infliximab, motavizumab, muronomab-CD3, natalizumab, ofatumumab, omalizumab, palivizumab, panitumumab, raxibacumab, ranibizumab, rituximab, tocilizumab, tositumomab, trastuzumab, ustekinumab, anti-CD30 antibody cAC10, RGD-peptide homing ligands, 2-[3(1,3-dicarboxypropyl)-ureido] pentanedioic acid (DUPA) targeting prostate specific membrane antigen (PSMA), epidermal growth factor, vascular endothelial growth factor, steroidal estrogens, somatostatin, bombesin, polyunsaturated fatty acids, lectins, folate, biotin, riboflavin, hyaluronic acid, and transferrin.

2. A method of claim 1, wherein each X is a spacer.

3. A method of claim 1, wherein each X is non-cleavable spacer when the conjugates contains radioisotopes.

4. A method of claim 1, step (a), wherein the said Linker-Drug conjugate compound of Formula IV, V or VI is formed between the functional group Z present in a linker compound of Formula I, II or III and a functional group, either natively present or chemically introduced, in the drug moiety selected from primary or secondary amine, hydroxyl, sulfhydryl, carboxyl, aldehyde or ketone via a covalent bond by esterification, amidation, reductive amination or aldol reaction.

5. A method of claim 1, wherein step (b) proceeds either under UV irradiation at wavelength of 254 or 365 nm, or via thermal reaction, in the presence of initiator selected from the group consisting of diphenyl 2,4,6-trimethylbenzoyl phosphine oxide, 2,2-dimethoxy-2-phenylacetophenone, benzophenone, DL-Camphorquinone, dimethyl phenyl phosphine,

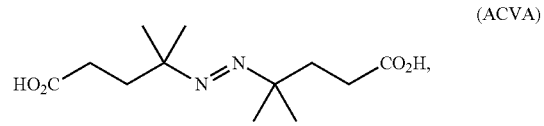

(ACVA)

-continued
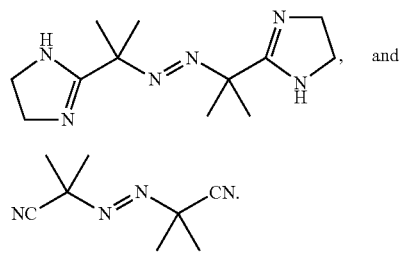
(VA-044)
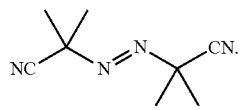
(AIBN)
* * * * *